United States Patent
Li et al.

(10) Patent No.: US 10,500,165 B2
(45) Date of Patent: Dec. 10, 2019

(54) PURIFIED THERAPEUTIC NANOPARTICLES AND PREPARATION METHODS THEREOF

(71) Applicant: CSPC ZHONGQI PHARMACEUTICAL TECHNOLOGY (SHIJIAZHUANG) CO., LTD., Shijiazhuang (CN)

(72) Inventors: Chunlei Li, Shijiazhuang (CN); Yanhui Li, Shijiazhuang (CN); Min Liang, Shijiazhuang (CN); Caixia Wang, Shijiazhuang (CN); Yajuan Wang, Shijiazhuang (CN); Shixia Wang, Shijiazhuang (CN); Dongjian Chen, Shijiazhuang (CN); Yongfeng Li, Shijiazhuang (CN)

(73) Assignee: CSPC ZHONGQI PHARMACEUTICAL TECHNOLOGY (SHIJIAZHUANG) CO., LTD.

( * ) Notice: Subject to any disclaimer, the term of this patent is extended or adjusted under 35 U.S.C. 154(b) by 0 days.

(21) Appl. No.: 14/790,646

(22) Filed: Jul. 2, 2015

(65) Prior Publication Data

US 2016/0000726 A1 Jan. 7, 2016

Related U.S. Application Data

(63) Continuation-in-part of application No. PCT/CN2014/091277, filed on Nov. 17, 2014.

(30) Foreign Application Priority Data

Jul. 3, 2014 (CN) .......................... 2014 1 0314042

(51) Int. Cl.
| | | |
|---|---|---|
| A61K 9/51 | (2006.01) | |
| B82Y 5/00 | (2011.01) | |
| A61K 31/337 | (2006.01) | |

(52) U.S. Cl.
CPC .......... A61K 9/5169 (2013.01); A61K 31/337 (2013.01); B82Y 5/00 (2013.01)

(58) Field of Classification Search
CPC ....... A61K 9/5169; A61K 31/337; B82Y 5/00
See application file for complete search history.

(56) References Cited

U.S. PATENT DOCUMENTS

| | | |
|---|---|---|
| 5,059,699 A | 10/1991 | Kingston et al. |
| 5,439,686 A | 8/1995 | Desai et al. |
| 5,498,421 A | 3/1996 | Grinstaff et al. |
| 5,916,596 A | 6/1999 | Desai et al. |
| 6,096,331 A | 8/2000 | Desai et al. |
| 6,506,405 B1 | 1/2003 | Desai et al. |
| 6,515,017 B1 | 2/2003 | Li et al. |
| 6,537,579 B1 | 3/2003 | Desai et al. |
| 6,749,868 B1 | 6/2004 | Desai et al. |
| 6,753,006 B1 | 6/2004 | Desai et al. |
| 7,758,891 B2 | 7/2010 | Desai et al. |
| RE41,884 E | 10/2010 | De Garavilla et al. |
| 7,820,788 B2 | 10/2010 | Desai et al. |
| 7,923,536 B2 | 4/2011 | Desai et al. |
| 8,034,375 B2 | 10/2011 | Desai et al. |
| 8,138,229 B2 | 3/2012 | Desai et al. |
| 8,268,348 B2 | 9/2012 | Desai et al. |
| 8,314,156 B2 | 11/2012 | Desai et al. |
| 2005/0004002 A1* | 1/2005 | Desai ................... A61K 9/0019 514/15.2 |
| 2007/0129448 A1 | 6/2007 | Desai et al. |
| 2007/0166388 A1* | 7/2007 | Desai ................... A61K 9/0019 424/489 |
| 2008/0095857 A1 | 4/2008 | Balthasar et al. |
| 2012/0283205 A1 | 11/2012 | Desai et al. |
| 2013/0244952 A1 | 9/2013 | Desai et al. |
| 2013/0266659 A1 | 10/2013 | Desai et al. |
| 2014/0039069 A1 | 2/2014 | Desai et al. |
| 2014/0039070 A1 | 2/2014 | Desai et al. |

FOREIGN PATENT DOCUMENTS

| | | | |
|---|---|---|---|
| CN | 1237901 A | 12/1999 | |
| CN | 1736489 A | 2/2006 | |
| CN | 102908321 A | * 2/2013 | ............... A61K 9/19 |
| CN | 102908321 A | 2/2013 | |
| CN | 102988996 | * 3/2013 | |
| CN | 102988996 A | 3/2013 | |
| CN | 103221042 A | 7/2013 | |
| RU | 2119482 C1 | 9/1998 | |
| RU | 2388463 C2 | 5/2010 | |
| WO | 92/12132 A1 | 7/1992 | |
| WO | WO 00/71079 A2 | 11/2000 | |
| WO | 2011/057709 A1 | 5/2011 | |
| WO | 2011/153010 A1 | 12/2011 | |
| WO | WO2011/153010 | * 12/2011 | |

OTHER PUBLICATIONS

Langer et al., Optimization of the preparation process for human serum albumin (HAS) nanoparticles, International Journal of Pharmaceutics 257 (2003) 169-180.*

Chapter 17 of Excipient Development for Pharmaceutical, Biotechnology, and Drug Delivery Systems, Edited by Katdare and Chaubal, 2006, 42pp, Taylor & Francis Group, LLC.*

(Continued)

*Primary Examiner* — Karlheinz R. Skowronek
*Assistant Examiner* — Joseph Fischer
(74) *Attorney, Agent, or Firm* — Seed IP Law Group LLP

(57) ABSTRACT

Purified therapeutic nanoparticles are provided herein. Such nanoparticles comprise an active pharmaceutical ingredient and human serum albumin, wherein the weight ratio of human serum albumin to the active ingredient in the therapeutic nanoparticles is from 0.01:1 to 1:1, and wherein the nanoparticles are substantially free of free human serum albumin that is not incorporated in the nanoparticles. The present disclosure also provides pharmaceutical compositions that comprise the purified therapeutic nanoparticles and are also substantially free of free human serum albumin. Methods for preparing and using the purified therapeutic nanoparticles and compositions thereof are also provided.

28 Claims, 8 Drawing Sheets

(56) References Cited

OTHER PUBLICATIONS

Chaubal, Human Serum Albumin as a Pharmaceutical Excipient, Drug Development and Delivery, vol. 5, No. 9, Sep. 2005.*
Of Irache and Espuelas, Chapter 7 Albumin Nanoparticles, in Nanotechnologies for the Life Sciences vol. 2 Biological and Pharmaceutical Nanomaterials. Edited by Challa S. S. R. Kumar.*
Lundqvist et al., Nanoparticle size and surface properties determine the protein corona with possible implications for biological impacts, PNAS Sep. 23, 2008 vol. 105 No. 38 pp. 14265-14270.*
Kufleitner et al., Adsorption of obidoxime onto human serum albumin nanoparticles: Drug loading, particle size and drug release, JI Microencapsulation, 2010; 27(6): 506-513.*
Elzoghby et al.,Review: Albumin-based nanoparticles as potential controlled release drug delivery systems, JI. Controlled Rel., 157 (2012) 168-182.*
Irache and Espuelas, Chapter 7 Albumin Nanoparticles, in Nanotechnologies for the Life Sciences vol. 2 Biological and Pharmaceutical Nanomaterials. Edited by Challa S. S. R. Kumar, Feb. 2006.*
Zhang et al., Preparation of the albumin nanoparticle system loaded with both paclitaxel and sorafenib and its evaluation in vitro and in vivo, Journal of Microencapsulation, 28:6, 528-536, Jun. 2011.*
Xu et al., Bioconjug Chem. May 18, 2011; 22(5): 870-878.*
In re Chapman, 357 F.2d 418, 148 USPQ 711 (CCPA 1966), 8 pages.*
Ding et al., published online Nov. 28, 2013, then as Aaps PharmSciTech, vol. 15, No. 1, Feb. 2014 (Year: 2013).*
Google Machine translation into English of CN 102988996, inventors Wang et al., published in Chinese Mar. 27, 2013 (provided in Feb. 11, 2019 IDS, provided, 11 pages) (Year: 2013).*
von Storp et al., Journal of Microencapsulation, 2012; 29(2): 138-146 (Year: 2012).*
Abraxane® for Injectable Suspension (paclitaxel protein-bound particles for injectable suspension) (albumin-bound), Prescribing Information, (24 Pages), (Jul. 2015).
Mathew et al., "Synthesis and Evaluation of Some Water-Soluble Prodrugs and Derivatives of Taxol with Antitumor Activity," *J. Med. Chem.* 35:145-151 (1992).
Ranade et al., "A multicenter phase II randomized study of Cremophor-free polymeric nanoparticle formulation of paclitaxel in women with locally advanced and/or metastatic breast cancer after failure of anthracycline," *Asia-Pacific Journal of Clinical Oncology* 9:176-181 (2013).
Extended European Search Report, dated Jun. 14, 2017, for European Application No. 15815596.0-1468 / 3164114, 10 pages.
Ibrahim et al., "Albumin-bound nanoparticies of practically water-insoluble antimalarial lead greatly enhance its efficacy," *International Journal of Pharmaceutics* 464:214-224, 2014.
Li et al., "Direct comparison of two albumin-based paclitaxel-loaded nanoparticle formulations: Is the crosslinked version more advantageous?" *International Journal of Pharmaceutics* 468:15-25, 2014.
Stollenwerk et al., "Albumin-based nanoparticles as magnetic resonance contrast agents: I, Concept, first synthesis and characterisation," *Histochem Cell Biol* 133:375-404, 2010.
Japanese Office Action for corresponding Japanese Patent Application No. 2016-575327, dated Jan. 17, 2019 (with translation).
Russian Office Action for corresponding RU Patent Application No. 2017101992, dated Feb. 22, 2019 (with English translation).
Office Action corresponding to related Russian Application No. 2017101992, with English translation, 7 pp., dated Jun. 27, 2019. 2 3 4 5 6.

* cited by examiner

PURIFIED THERAPEUTIC NANOPARTICLES AND PREPARATION METHODS THEREOF

TECHNICAL FIELD

The present disclosure relates to the pharmaceutical field, and more particularly, to nanoparticles comprising human serum albumin and a hydrophobic drug, and the preparation method thereof, and even more particularly, to albumin nanoparticles comprising specific physical properties and the preparation method thereof.

BACKGROUND

As an anticancer drug, paclitaxel acts as a microtubule inhibitor in mitosis, and plays an important role in polymerization and stabilization of intracellular microtubule. At the stage of mitosis, paclitaxel disables the separation of microtubules, so that cells are blocked between G2 and M phase. As a result, the fast-dividing tumor cells are arrested at the phase of mitosis by paclitaxel, leading to the death of the cells due to hindered replication. Paclitaxel has important clinical activity to various cancers (for example, breast cancer, ovarian cancer, lung cancer, and bladder cancer, etc.).

Due to poor water-solubility, however, the application of paclitaxel in human body is limited. In order to make paclitaxel suitable for intravenous injection, Bristol-Myers Squibb (BMS) has developed TAXOL®, in which a surfactant polyoxyethylene castor oil (CREMOPHOR® EL) and anhydrous alcohol are added together as co-solvent to enhance the solubility of paclitaxel. Taxol has significant activity to ovarian cancer, breast cancer, lung cancer, esophagus cancer, and head and neck cancer. However, it has been demonstrated that Taxol may induce therapy-related toxicity, and significant acute and accumulative toxicity, such as myelosuppression, febrile neutropenia and hypersensitivity etc. These side effects are related to the surfactant polyoxyethylene castor oil used (Anantbhushan et al., Asia Pac J Clin Oncol. 2013; 9:176-181). Based on clinical research reports and post-marketing safety data, an overall incidence of hypersensitivity induced by Taxol is about 39%. At present, antihistamines and steroids are administrated to patients ahead of time to alleviate the side effects due to the surfactant, when Taxol is used.

In order to improve the water solubility of paclitaxel, structure modifications are also conducted by researchers using functional groups which may provide higher water solubility, for example, sulfonate derivatives (Kingston et al., U.S. Pat. No. 5,059,699 (1991)), and amino-acid ester derivatives (Mathew et al., J. Med. Chem. 35:145-151 (1992)). They exhibit obvious biological activities after modification. However, these modifications may induce undesired side effects or reduce the pharmaceutical efficiency besides the increase of cost of the pharmaceutical formulations.

To avoid adverse effects of CREMOPHOR® EL in paclitaxel formulations, another drug delivery system that does not contain any emulsifying agent or surfactant was developed. Such a system is in the form of micro-particles or nanoparticles and contains albumin, a portion of which forms complexes with paclitaxel. However, this system still has many disadvantages. For example, the formulation requires a large amount of human serum albumin (HSA), which may cause allergy. HSA is still obtained from human blood, and has potential safety risks due to possible contaminations during blood collection and storage. In addition, HSA is relatively expensive and may be in shortage in certain regions.

SUMMARY

The present disclosure provides purified therapeutic nanoparticles, compositions comprising such nanoparticles, methods of preparing such nanoparticles or compositions, and methods of using such nanoparticles or compositions.

In one aspect, the present disclosure provides purified therapeutic nanoparticles that comprise an active ingredient and human serum albumin, wherein the weight ratio of human serum albumin (HSA) to the active ingredient in the therapeutic nanoparticles is selected from 0.01:1, 0.02:1, 0.04:1, 0.05:1, 0.06:1, 0.07:1, 0.08:1, 0.09:1, 0.10:1, 0.11:1, 0.12:1, 0.13:1, 0.14:1, 0.15:1, 0.16:1, 0.17:1, 0.18:1, 0.19:1, 0.2:1, 0.21:1, 0.22:1, 0.23:1, 0.24:1, 0.25:1, 0.26:1, 0.27:1, 0.28:1, 0.29:1, 0.3:1, 0.31:1, 0.32:1, 0.33:1, 0.34:1, 0.35:1, 0.36:1, 0.37:1, 0.38:1, 0.39:1, 0.4:1, 0.41:1, 0.42:1, 0.43:1, 0.44:1, 0.45:1, 0.46:1, 0.47:1, 0.48:1, 0.49:1, 0.5:1, 0.51:1, 0.52:1, 0.53:1, 0.54:1, 0.55:1, 0.56:1, 0.57:1, 0.58:1, 0.59:1, 0.6:1, 0.65:1, 0.70:1, 0.75:1, 0.8:1, 0.85:1, 0.9:1, 0.95:1, 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1 or the range between any two ratios above, and wherein the therapeutic nanoparticles are substantially free of free HSA that is not incorporated in the nanoparticles.

In certain embodiments, the weight ratio of human serum albumin to the active ingredient is selected from 0.03:1, 0.04:1, 0.05:1, 0.06:1, 0.07:1, 0.08:1, 0.09:1, 0.10:1, 0.11:1, 0.12:1, 0.13:1, 0.14:1, 0.15:1, 0.16:1, 0.17:1, 0.18:1, 0.19:1, 0.2:1, 0.21:1, 0.22:1, 0.23:1, 0.24:1, 0.25:1, 0.26:1, 0.27:1, 0.28:1, 0.29:1, 0.3:1, 0.31:1, 0.32:1, 0.33:1, 0.34:1, 0.35:1, 0.36:1, 0.37:1, 0.38:1, 0.39:1, 0.4:1, 0.41:1, 0.42:1, 0.43:1, 0.44:1, 0.45:1, 0.46:1, 0.47:1, 0.48:1, 0.49:1, 0.5:1, 0.6:1, 0.7:1, 0.8:1, 0.9:1, or the range between any two ratios above.

In certain embodiments, the nanoparticles contain at most 5% free HSA (by weight).

In certain embodiments, the active ingredient has the properties of being insoluble or slightly soluble in water, but soluble or free soluble in an organic solvent.

In certain embodiments, the active ingredient is selected from taxanes, macrolides, camptothecins anthracycline antibiotics, colchicine, thiocolchicine dimer, amiodardone, liothyronine, cyclosporine, exemestane, flutamide, fulvestrant, romidepsin, semustine, and ibuprofen.

In certain embodiments, the active ingredient is a taxane, such as paclitaxel or docetaxel.

In certain embodiments, the organic solvent is a pure solvent having low water-solubility and low boiling point or its mixture with small molecular alcohols.

In certain embodiments, the active ingredient is encapsulated inside human serum albumin.

In certain embodiments, the average particle size of the therapeutic nanoparticles is selected from: 30, 40, 50, 60, 70, 80, 90, 100, 110, 120, 121, 122, 123, 124, 125, 126, 127, 128, 129, 130, 131, 132, 133, 134, 135, 136, 137, 138, 140, 141, 142, 143, 144, 145, 146, 147, 148, 149, 150, 151, 152, 153, 154, 155, 156, 157, 158, 159, 160, 165, 170, 175, 180, 185, 190, 195, 200 nm, or the range between any two numerical values above.

In another aspect, the present disclosure provides purified therapeutic nanoparticles that comprise an active ingredient and human serum albumin, wherein the active ingredient is encapsulated inside human serum albumin; the weight ratio of human serum albumin to the active ingredient is from 0.03:1 to 0.7:1; the average particle size of the therapeutic nanoparticles is from 50 nm to 190 nm; and the nanoparticles are substantially free of free HSA that is not incorporated in the nanoparticles.

In another aspect, the present disclosure provides a pharmaceutical composition, comprising the purified therapeutic nanoparticles provided herein, wherein the composition is substantially free of free HSA that is not incorporated in the nanoparticles.

In certain embodiments, the pharmaceutical composition is in the form of liquid or lyophilized powder.

In certain embodiments where the pharmaceutical composition is in the form of lyophilized powder, it comprises one or more lyophilization excipients, such as mannitol, sucrose, lactose, maltose, trehalose, dextran, or a mixture thereof.

In certain embodiments, the pharmaceutical composition contains at most 5% free HSA (by weight).

In another aspect, the present disclosure provides a method for preparing the purified therapeutic nanoparticles provided herein. The method comprises:

1) dissolving the active ingredient in organic solvent to form an oil phase, and dissolving human serum albumin in water to form an aqueous phase;

2) forming an oil-in-water emulsion using the oil phase and aqueous phase above;

3) removing the organic solvent in the emulsion to obtain a suspension containing the therapeutic nanoparticles; and 4) removing free HSA that is not incorporated in the nanoparticles from the suspension to obtain purified therapeutic nanoparticles.

In certain embodiments, the organic solvent is selected from one or more of chloroform and ethanol.

In certain embodiments, the method further comprises: between steps 3) and 4), a step of dialyzing the suspension of step 3) with an aqueous solution to remove remaining organic solvent from the suspension.

In certain embodiments, the aqueous solution is water.

In certain embodiments, said separating in step 4) is conducted using a method selected from: centrifugation, dialysis, and exclusion chromatography.

In a related aspect, the present disclosure provides method for preparing the pharmaceutical composition provided herein, comprising:

1) dissolving the active ingredient in organic solvent to form an oil phase, and dissolving human serum albumin in water to form an aqueous phase;

2) forming an oil-in-water emulsion using the oil phase and aqueous phase above;

3) removing the organic solvent in the emulsion to obtain a suspension containing the therapeutic nanoparticles;

4) removing free HSA that is not incorporated in the nanoparticles to obtain purified therapeutic nanoparticles;

5) re-suspending the purified therapeutic nanoparticles in an excipient-containing solution; and 6) optionally lyophilizing the re-suspension of the purified therapeutic nanoparticles to obtain the pharmaceutical composition.

In certain embodiments, the method further comprises: between steps 3) and 4), a step of dialyzing the suspension of step 3) with an aqueous solution to remove remaining organic solvent from the suspension.

In certain embodiments, the aqueous solution is water.

In another related aspect, the present disclosure provides a method for preparing the pharmaceutical composition provided herein, comprising:

1) dissolving the active ingredient in organic solvent to form an oil phase, and dissolving human serum albumin in water to form an aqueous phase;

2) forming an oil-in-water emulsion using the oil phase and aqueous phase above;

3) removing the organic solvent in the emulsion to obtain a suspension containing the therapeutic nanoparticles;

4) dialyzing the suspension obtained after removal of the organic solvent by an excipient-containing solution to remove free HSA that is not incorporated in the nanoparticles; and 5) optionally lyophilizing the dialyzed suspension to obtain the pharmaceutical composition.

In certain embodiments, the method further comprises: between steps 3) and 4), a step of dialyzing the suspension of step 3) with an aqueous solution to remove remaining organic solvent from the suspension.

In certain embodiments, the aqueous solution is water.

In another aspect, the present disclosure provides a method for treating cancer, comprising: administrating a therapeutically effective amount of the pharmaceutical composition provided herein to a subject in need thereof.

In another aspect, the present disclosure provides a pharmaceutical composition, comprising the therapeutic nanoparticles provided herein, wherein the composition further comprises HSA as a lyophilization excipient.

DETAILED DESCRIPTION

Figure 1:
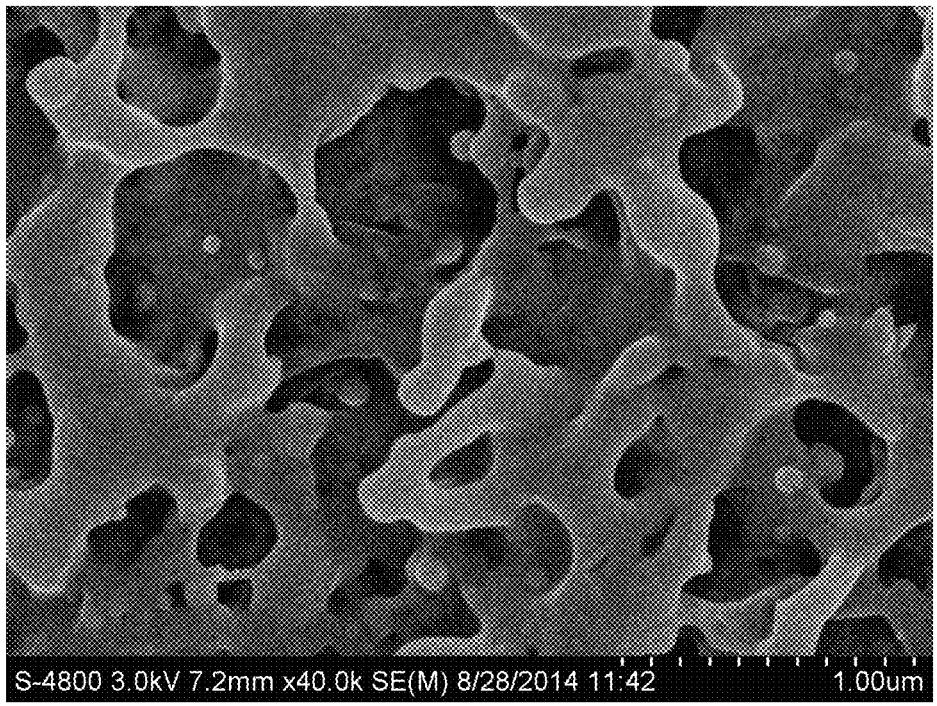
FIG. 1. Scanning electron microscopic image of the sample of Example 5.

The present disclosure provides purified HSA-containing therapeutic nanoparticles, compositions comprising such nanoparticles and methods of preparing or using such nanoparticles and compositions.

The purified therapeutic nanoparticles or the compositions that comprising such nanoparticles have one or more of the following superior properties:

(1) Compared with previously known compositions that comprise HSA-containing nanoparticles, the purified therapeutic nanoparticles or compositions thereof reduce allergic reactions in subjects to which the nanoparticles or compositions are administered (see e.g., Examples 25, 27, and 61). While not wishing to be bound by any hypothesis, it is proposed that the reduction in allergic reactions may be resulted from the reduced amount of HSA polymers in the purified nanoparticles or compositions thereof. It was discovered by the present inventors that during the preparation of nanoparticles, a portion of HSA monomers formed HSA polymers, causing more severe allergic reactions (see e.g., Examples 32 and 60). Purification of nanoparticles from the initial preparation eliminates most free HSA that is not incorporated into nanoparticles, including free HSA polymers.

(2) Compared with previously known compositions that comprise HSA-containing nanoparticles, certain compositions comprising purified therapeutic nanoparticles provided herein are more stable (see e.g., Examples 62 and 63). This is unexpected in view of the significant reduction in the ratio of HSA to active ingredients in the purified nanoparticles and compositions of the present disclosure and in view of the belief in the art that a large amount of HSA is important or required for stabilizing compositions that comprise nanoparticles.

(3) While maintaining in vitro release profiles, maximum tolerated doses, pharmacokinetic properties, and effectiveness in animal studies (see e.g., Examples 22 and 26-31), purified therapeutic nanoparticles or compositions thereof provided herein are easier to be delivered to or taken up by human target cells (e.g., human tumor cells and human vascular endothelial cells) and achieved better desirable effects in those cells (see e.g., Examples 58 and 59).

Unless otherwise defined, all scientific terms used herein have the same meaning as commonly understood by one of ordinary skills in the art to which this disclosure belongs.

Although the number ranges and approximate parameter values are given in a broad range of the present disclosure, all numbers in the specific examples are described as precise as possible. However, certain error exists in any numerical values essentially, which may be resulted from the standard deviation during the measurement for each of them. Additionally, it should be understood that all ranges disclosed herein encompass any and all possible sub-ranges contained therein. For example, it should be understood that the range "from 1 to 10" described herein encompasses any and all possible sub-ranges between the minimum 1 and the maximum 10 (including the endpoints); i.e., all sub-ranges started from the minimum 1 or more, e.g., 1 to 6.1, and all sub-ranges ended at the maximum 10 or less, e.g., 5.5 to 10. Additionally, it should be understood that any reference referred as "incorporated herein" is incorporated in its entirety.

Additionally, it should be noted that unless otherwise clearly and explicitly stated, the singular form includes the plural referent, as used in the present disclosure. The term "or" and the term "and/or" are used interchangeably, unless otherwise clearly indicated in the context.

The term "nanoparticle" used herein refers to the particle with at least one dimension (for example, 1, 2, or 3 dimensions) in nano-scale, for example, at the level of about 1 nm, about 10 nm, or about 100 nm.

The term "about" means more or less than 10% of a particular value. For example, "about 50 nm" refers to 45 nm to 55 nm.

The term "therapeutic nanoparticle" used herein refers to the nanoparticles that can be used for the treatment or prevention of diseases, wherein the diseases, for example cancers, are preferably selected from liver cancer, prostatic cancer and lung cancer.

The term "human serum albumin monomer" or "HSA monomer" used herein refers to the water soluble globulin composed of 585 amino acids and the approximate molecular weight is around 66,000 Daltons. It is the most abundant protein in human blood plasma. The retention time for human serum albumin monomer is the longest in size exclusion chromatography and count for the majority in normal human albumin products. HSA has multiple hydrophobic binding sites which can bind a diverse set of drugs, especially neutral and negatively charged hydrophobic compounds.

The term "human serum albumin polymer" or "HSA polymer" used herein refers to the sum of polymers polymerized by human serum albumin monomer, including dimer, trimer and polymer. The retention time for human serum albumin polymer in size exclusion chromatography is shorter than HSA monomers. HSA polymers are present in only a small amount (typically<5%) in human albumin products.

HSA is accumulated in various growing tumors and is used as a source of energy and amino acids uptake by tumor cells. gp60 (albondin) is hyper-expressed in the endothelium of blood vessels and binds HSA to carry it into the underlying tissue by transcytosis. gp60 is not expressed in tissue cells and it is not involved in the HSA transport in tissue cells. SPARC (secreted protein, acidic and rich in cysteine), has the homologous amino acids sequences with gp60 and can bind HSA and gp60 antibodies. SPARC is over-expressed in multiple tumor types and many studies manifest that SPARC correlates with the tissue cellular uptake of HSA. There are researches suggest that HSA-bound drugs also cross the endothelial barrier to the tumor tissue and internalize in tumor cells via Gp60-SPARC transmembrane transport pathway.

The term "substantially pure nanoparticles" or "purified nanoparticles" used herein refers to nanoparticles composed of human serum albumin and an active ingredient where less than 10% HSA (e.g., less than 9%, less than 8%, less than 7%, less than 6%, less than 5%, less than 4%, less than 3%, less than 2%, less than 1%, less than 0.5%, or less than 0.1%) is free HSA.

Similarly, the term "substantially free of free human serum albumin" or "substantially free of free HSA" used herein refers to having less than 10% free HSA (e.g., less than 9%, less than 8%, less than 7%, less than 6%, less than 5%, less than 4%, less than 3%, less than 2%, less than 1%, less than 0.5%, or less than 0.1%) [78] The term "free human serum albumin" or "free HSA" used herein refers to HSA is not incorporated in nanoparticles. The amount of free HSA in nanoparticles or compositions thereof may be measured by methods known in the art or a method provided in the present disclosure, such as in Examples 11 and 17-19.

The term "active ingredient" used herein refers to the active pharmaceutical ingredient. Particularly, the active ingredient refers to any substance or entity that can play a therapeutic role (for example, the treatment, prevention, alleviation or suppression of any disease and/or disorder).

The term "dialysis fold" used herein refers to the volume ratio of dialysate consumed to a sample solution in a dialysis process where the volume of the sample solution is kept constant.

The term "lyophilization excipient" used herein refers to compounds added to a pharmaceutical composition that comprises purified therapeutic nanoparticles to maintain such nanoparticle during the freeze-drying process.

The terms, "treat" and "treatment," refer to medical management of a disease, disorder, or condition of a subject (i.e., patient) (see, e.g., Stedman's Medical Dictionary). "Treating cancer" refers to reducing the number of symptoms of cancer, decreasing the severity of one or more symptoms, or delaying cancer progression.

A "therapeutically effective dose" of a specific therapeutic agent refers to that amount of the agent sufficient to result in reducing the severity of, eliminating, or delaying the onset or reoccurrence of one or more symptoms of cancer in a statistically significant manner.

In one aspect, the present disclosure provides purified therapeutic nanoparticles that comprise an active ingredient and HSA.

In some embodiments, the weight ratio of human serum albumin to the active ingredient in the therapeutic nanoparticles is selected from the group consisting of 0.01:1, 0.02:1, 0.04:1, 0.05:1, 0.06:1, 0.07:1, 0.08:1, 0.09:1, 0.10:1, 0.11:1, 0.12:1, 0.13:1, 0.14:1, 0.15:1, 0.16:1, 0.17:1, 0.18:1, 0.19:1, 0.2:1, 0.21:1, 0.22:1, 0.23:1, 0.24:1, 0.25:1, 0.26:1, 0.27:1, 0.28:1, 0.29:1, 0.3:1, 0.31:1, 0.32:1, 0.33:1, 0.34:1, 0.35:1, 0.36:1, 0.37:1, 0.38:1, 0.39:1, 0.4:1, 0.41:1, 0.42:1, 0.43:1, 0.44:1, 0.45:1, 0.46:1, 0.47:1, 0.48:1, 0.49:1, 0.5:1, 0.51:1, 0.52:1, 0.53:1, 0.54:1, 0.55:1, 0.56:1, 0.57:1, 0.58:1, 0.59:1, 0.6:1, 0.65:1, 0.70:1, 0.75:1, 0.8:1, 0.85:1, 0.9:1, 0.95:1, 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1 or the range between any two ratios above.

In some specific embodiments, the weight ratio of human serum albumin to the active ingredient is selected from the group consisting of 0.03:1, 0.04:1, 0.05:1, 0.06:1, 0.07:1, 0.08:1, 0.09:1, 0.10:1, 0.11:1, 0.12:1, 0.13:1, 0.14:1, 0.15:1, 0.16:1, 0.17:1, 0.18:1, 0.19:1, 0.2:1, 0.21:1, 0.22:1, 0.23:1, 0.24:1, 0.25:1, 0.26:1, 0.27:1, 0.28:1, 0.29:1, 0.3:1, 0.31:1, 0.32:1, 0.33:1, 0.34:1, 0.35:1, 0.36:1, 0.37:1, 0.38:1, 0.39:1, 0.4:1, 0.41:1, 0.42:1, 0.43:1, 0.44:1, 0.45:1, 0.46:1, 0.47:1, 0.48:1, 0.49:1, 0.5:1, 0.6:1, 0.7:1, 0.8:1, 0.9:1 or the range between any two ratios above, for example, 0.03:1 to 0.19:1, or 0.21:1 to 0.9:1.

More particularly, in certain embodiments, the weight ratio of human serum albumin to the active ingredient is 0.043:1, 0.071:1, 0.13:1, 0.15:1, 0.16:1, 0.17:1, 0.18:1, 0.24:1, or 0.57:1, or the range between any two ratios above, for example, 0.043:1 to 0.071:1, 0.043:1 to 0.13:1, 0.043:1 to, 0.043:1 to 0.15:1, 0.043:1 to 0.16:1, 0.043:1 to 0.17:1, 0.043:1 to 0.18:1, 0.043:1 to 0.24:1, 0.043:1 to 0.57:1, 0.071:1 to 0.13:1, 0.071:1 to 0.15:1, 0.071:1 to 0.16:1, 0.071:1 to 0.17:1, 0.071:1 to 0.18:1, 0.071:1 to 0.24:1, 0.071:1 to 0.57:1, 0.13:1 to 0.15:1, 0.13:1 to 0.16:1, 0.13:1 to 0.17:1, 0.13:1 to 0.18:1, 0.13:1 to 0.24:1, 0.13:1 to 0.57:1, 0.15:1 to 0.16:1, 0.15:1 to 0.17:1, 0.15:1 to 0.18:1, 0.15:1 to 0.24:1, 0.15:1 to 0.57:1, 0.16:1 to 0.17:1, 0.16:1 to 0.18:1, 0.16:1 to 0.24:1, 0.16:1 to 0.57:1, 0.17:1 to 0.18:1, 0.17:1 to 0.24:1, 0.17:1 to 0.57:1, 0.18:1 to 0.24:1, 0.18:1 to 0.57:1 or 0.24:1 to 0.57:1.

In some embodiments, the active ingredient suitable for encapsulation inside human serum albumin are insoluble or slightly soluble in water, and soluble or freely soluble in an organic solvent. The organic solvent may be a pure solvent with low water solubility (i.e., water solubility less than 6%) and low boiling point (i.e., boiling point lower than 80° C.) or its mixture of the above-described pure solvent with small molecular alcohols including ethanol, tert-butanol, isopropanol, etc. The specific organic solvents include but are not limit to chloroform, dichloromethane, etc.

The active ingredient suitable for the present disclosure is taxanes, including but not limited to, paclitaxel, docetaxel, cabazitaxel, hydrophobic derivatives of docetaxel (e.g., 2'-O-hexanoyldocetaxel, and 2'-benzoyldocetaxel); or macrolides, including but not limited to rapamycin and its derivatives (e.g., temsirolimus and everolimus), epothilone B and its derivatives, tanespimycin and its derivatives; or camptothecins, including but not limited to 10-hydroxy camptothecin, SN-38 and its derivatives; or anthracycline antibiotics, including but not limited to aclacinomycin and pirarubicin; or other active ingredients including colchicine and its derivatives, thiocolchicine dimer, amiodardone, liothyronine, cyclosporine, exemestane, flutamide, fulvestrant, romidepsin, semustine, ibuprofen, cyclosporine, propofol, vinblastine, etc. In some embodiments, the active ingredient is selected from one or more of paclitaxel and docetaxel. In particular embodiments, the active ingredient is paclitaxel. In some other embodiments, the active ingredient is selected from docetaxel, rapamycin and its derivatives, exemestane, flutamide, fulvestrant, etc.

In certain embodiments, the active ingredient includes but is not limited to: chemotherapeutics, radiotherapeutic agents, immunotherapeutic agents, and thermally therapeutic agents etc. For example, aminoglutethimide, azathioprine, bleomycin sulphate, busulfan, carmustine, chlorambucil, cisplatin, cyclophosphamide, cyclosporine, dacarbazine, dactinomycin, daunorubicin, amycin, paclitaxel, etoposide, fluorouracil, interferon-α, lomustine, mercaptopurine, methoptrexate, mitotane, procarbazine hydrochloride, thioguanine, vinblastine sulfate and vincristine sulfate.

In some embodiments, the average particle size of the therapeutic nanoparticles is selected from 30, 50, 70, 120, 121, 122, 123, 124, 125, 126, 127, 128, 129, 130, 131, 132, 133, 134, 135, 136, 137, 138, 140, 141, 142, 143, 144, 145, 146, 147, 148, 149, 150, 151, 152, 153, 154, 155, 156, 157, 158, 159, 160, 165, 170, 175, 180, 185, 190, 195, 200 nm, or the range between any two numerical values above. It should be understood by the skilled person in the art that the particle size can be determined using any appropriate method that exists or will appear in the future, which includes but is not limited to settling method, sieve method, microscopic observation or laser particle sizer. It also should be understood that when the therapeutic nanoparticles disclosed in the present disclosure comprise multiple particles, not all therapeutic nanoparticles should have the same particle size, and they will also be encompassed in the scope of the present disclosure, as long as their average particle size (i.e., the average particle diameter) falls in the above range. In some specific embodiments, the particle size is determined by a laser particle sizer; and the average particle size of the therapeutic nanoparticles is selected from 50, 60, 70, 80, 90, 100, 110, 120, 125, 126, 127, 128, 129, 130, 131, 132, 133, 134, 135, 136, 137, 138, 140, 141, 142, 143, 144, 145, 146, 147, 148, 149, 150, 151, 152, 153, 154, 155, 156, 157, 158, 159, 160 nm, or the range between any two numerical values above.

In some aspects, the particle sizes of the nanoparticles are in a specific range, for example, from 30 nm to 200 nm, preferably, from 50 to 190 nm. Preferably, the particle size is substantially uniform.

In one specific embodiment, purified therapeutic nanoparticles are provided, which comprise paclitaxel and human serum albumin, wherein paclitaxel is encapsulated in human serum albumin; and the weight ratio of human serum albumin to paclitaxel is 0.043:1, and the average particle size of the therapeutic nanoparticles is 140 nm.

In another specific embodiment, purified therapeutic nanoparticles are provided, which comprise paclitaxel and human serum albumin, wherein paclitaxel is encapsulated in human serum albumin; and the weight ratio of human serum albumin to paclitaxel is 0.071:1, and the average particle size of the therapeutic nanoparticles is 134 nm.

In another specific embodiment, purified therapeutic nanoparticles are provided, which comprise paclitaxel and human serum albumin, wherein paclitaxel is encapsulated in human serum albumin; and the weight ratio of human serum albumin to paclitaxel is 0.13:1, and the average particle size of the therapeutic nanoparticles is 125 nm.

In another specific embodiment, purified therapeutic nanoparticles are provided, which comprise paclitaxel and human serum albumin, wherein paclitaxel is encapsulated in human serum albumin; and the weight ratio of human serum albumin to paclitaxel is 0.15:1, and the average particle size of the therapeutic nanoparticles is 136 nm.

In another specific embodiment, purified therapeutic nanoparticles are provided, which comprise paclitaxel and human serum albumin, wherein paclitaxel is encapsulated in human serum albumin; and the weight ratio of human serum albumin to paclitaxel is 0.16:1, and the average particle size of the therapeutic nanoparticles is 133 nm.

In another specific embodiment, purified therapeutic nanoparticles are provided, which comprise paclitaxel and human serum albumin, wherein paclitaxel is encapsulated in human serum albumin; and the weight ratio of human serum albumin to paclitaxel is 0.17:1, and the average particle size of the therapeutic nanoparticles is 136 nm.

In another specific embodiment, purified therapeutic nanoparticles are provided, which comprise paclitaxel and human serum albumin, wherein paclitaxel is encapsulated in human serum albumin; and the weight ratio of human serum albumin to paclitaxel is 0.18:1, and the average particle size of the therapeutic nanoparticles is 138 nm.

In another specific embodiment, purified therapeutic nanoparticles are provided, which comprise paclitaxel and human serum albumin, wherein paclitaxel is encapsulated in human serum albumin; and the weight ratio of human serum albumin to paclitaxel is 0.24:1, and the average particle size of the therapeutic nanoparticles is 141 nm.

In another specific embodiment, purified therapeutic nanoparticles are provided, which comprise paclitaxel and human serum albumin, wherein paclitaxel is encapsulated in human serum albumin; and the weight ratio of human serum albumin to paclitaxel is 0.57:1, and the average particle size of the therapeutic nanoparticles is 145 nm.

In another specific embodiment, purified therapeutic nanoparticles are provided, which comprise docetaxel and human serum albumin, wherein docetaxel is encapsulated in human serum albumin; and the weight ratio of human serum albumin to docetaxel is 0.1:1, and the particle size of the therapeutic nanoparticles is in the range from 110 nm to 150 nm.

Purified therapeutic nanoparticles of the present disclosure are substantially free of free HSA. In certain embodiments, purified therapeutic nanoparticles contain at most 8%, 7%, 6%, 5%, 4%, 3%, 2%, 1%, 0.5% or 0.1% free HSA by weight (i.e., at most 8%, 7%, 6%, 5%, 4%, 3%, 2%, 1%, 0.5% or 0.1% of total HSA in the purified therapeutic nanoparticles is free HSA that does not bind an active ingredient and is not incorporated into nanoparticles.

In certain embodiments, purified therapeutic nanoparticles consist essentially of an active ingredient and HSA where substantially all of the HSA (i.e., more than 90%, 91%, 92%, 93%, 94%, 95%, 96%, 97%, 98%, 99%, 99.5%, or 99.9% of HSA) are bound to the active ingredient.

In certain embodiments, purified therapeutic nanoparticles comprise a minimum amount (e.g. less than 0.05, 0.04, 0.03, 0.02, or 0.01 mg/ml, or less than 5, 1, 0.5, 0.1, 0.05, or 0.01 µg/ml) of one or more organic solvents used in preparing such nanoparticles.

In certain embodiments, purified therapeutic nanoparticles do not comprise any surfactants.

In certain embodiments, purified nanoparticles provided herein have a relatively high zeta potential, such as from −20 to −45 or from −25 to −40.

In another aspect, the present disclosure provides a pharmaceutical composition that comprises purified therapeutic nanoparticles provided herein and is substantially free of free HSA that is not incorporated in the nanoparticles. In certain embodiments, the pharmaceutical composition comprises less than 10%, 9%, 8%, 7%, 6%, 5%, 4%, 3%, 2%, 1%, 0.5%, or 0.1% free HSA.

In some embodiments, the pharmaceutical composition is provided in the form of liquid, including but not limited to, the form suitable for injection to a subject. In one specific embodiment, the pharmaceutical composition is prepared into an injection.

In some other embodiments, the pharmaceutical composition is provided in the form of solid, including, but not limited to, dry powder or lyophilized powder.

In certain specific embodiments, the nanoparticle or the pharmaceutical composition of the present disclosure is free of deferoxamine or the salt thereof, for example, deferoxamine mesylate.

In certain specific embodiments, the purified nanoparticles or the pharmaceutical compositions of the present disclosure are free of additional stabilizer.

When provided in a liquid form, the pharmaceutical composition comprises the therapeutic nanoparticles of the present disclosure and a pharmaceutically acceptable carrier. The therapeutic nanoparticles are suspended in the pharmaceutically acceptable carrier. The pharmaceutically acceptable carrier includes but is not limited to a buffer solution, a preservative agent, water for injection, normal saline, and an isotonic solution. In some specific embodiments, the concentration of the active ingredient of therapeutic nanoparticles is 1-10 mg/ml (e.g., 5 mg/ml) in the pharmaceutical composition in a liquid form.

When provided in a solid form, the pharmaceutical composition comprises, consists essentially of, or consists of: the therapeutic nanoparticles of the present disclosure and a lyophilization excipient. In some specific embodiments, the lyophilization excipient is selected from one or more of mannitol, sucrose, lactose, maltose, trehalose, and dextran. In certain specific embodiments, the therapeutic nanoparticles are suspended in a solution of lyophilization excipient with the concentration from 5% to 10%, and subsequently the solution is lyophilized to obtain a pharmaceutical composition in a form of lyophilized powder. In particular embodiments, the solution of lyophilization excipient is selected from one or more of 5% mannitol solution, 10% sucrose solution, 5% dextran solution, 10% lactose solution, 10% trehalose solution, and 10% maltose solution. In some specific embodiments, the content of the therapeutic nanoparticles in the pharmaceutical composition in a solid form is from 4.8% to 10% by weight.

The method for preparing purified therapeutic nanoparticles of the present disclosure is also provided, comprising: (1) preparing a suspension containing therapeutic nanoparticles by mixing an active ingredient with human serum albumin, and (2) purifying nanoparticles from the suspension to obtain substantially pure therapeutic nanoparticles.

In another aspect, the present disclosure also provides therapeutic nanoparticles obtained by the method provided herein.

In another aspect, a method for preparing purified therapeutic nanoparticles is provided. The method comprises:

1) dissolving the active ingredient in organic solvent to form an oil phase, and dissolving human serum albumin in water to form an aqueous phase;

2) forming an oil-in-water emulsion using the oil phase and aqueous phase;

3) removing the organic solvent in the emulsion to obtain a suspension containing the therapeutic nanoparticles;

4) removing free HSA that is not incorporated in the nanoparticles from the suspension to obtain purified therapeutic nanoparticles.

Appropriate organic solvent(s) can be selected by the skilled person based on the properties of the active ingredient. In some specific embodiments, the suitable organic solvent is chloroform, ethanol or a mixture of chloroform and ethanol when the active ingredient is taxanes. More particularly, the suitable organic solvent is a mixture of chloroform and ethanol when the active ingredient is paclitaxel or docetaxel. In some specific embodiments, the volume ratio between chloroform and ethanol is in the range from 1:1 to 20:1, and for example, it is selected from 1:1, 4:1, 9:1 and 11:1. In some specific embodiments, the concentration of human serum albumin in the aqueous phase is in the range from 2% to 10% (w/v); for example, it is selected from 2%, 4%, 5% and 10%. In some embodiments, the ratio between the active ingredient and the organic solvent in the oil phase is in the range from 0.3-7.5 g/15-20 ml. In some specific embodiments, the ratio between the active ingredient and the organic solvent in the oil phase is selected from: 0.3 g/15 ml, 0.6 g/15 ml, 1 g/20 ml, 1.25 g/15 ml, 1.8 g/15 ml, 2 g/15 ml, 2.5 g/15 ml, 3 g/20 ml, 3 g/15 ml, 5 g/15 ml, 7.5 g/15 ml, or the range between any two numerical values above.

When an oil-in-water emulsion is formed with the oil phase and the aqueous phase, the volume ratio between the two phases is selected from 1:10 to 1:100. In some embodiments, the mixing ratio of the oil phase and the aqueous phase is 3:100 or 1:25. An oil-in-water emulsion is formed using the method known in the art, which includes, but not limited to, homogenization. In particular embodiments, the mixture of the oil phase and the aqueous phase is emulsified using a high shear disperser, and subsequently, it is homogenized using a high pressure homogenizer, so as to obtain an oil-in-water emulsion. In particular embodiments, the mixture of the oil phase and the aqueous phase is emulsified for 2-10 min using a high shear disperser, and subsequently, it is homogenized using a high pressure homogenizer under the pressure of 10000-20000 psi, so as to obtain an oil-in-water emulsion.

The organic solvent can be removed from the emulsion using any appropriate method. In some embodiments, the organic solvent is removed from the emulsion using rotary vacuum evaporation. In particular embodiments, the organic solvent is removed from the emulsion using a rotary evaporator at 40° C. under the pressure of 40 mbar. After removal of the organic solvent, the resulting suspension comprises the therapeutic nanoparticles of the present disclosure. However, excessive albumin, which does not participate in the formation of the nanoparticle, is also contained in the suspension.

Excessive free albumin is further removed from the suspension to obtain purified therapeutic nanoparticles of the present disclosure that are substantially free of free HSA. In some embodiments, this is conducted using centrifugation, dialysis, or exclusion chromatography. In particular embodiments, the suspension can be directly used for removing free HSA after removal of the organic solvent. Alternatively, it can be stored for further use.

Since intravenous infusion is the desirable administration route for the therapeutic nanoparticles of the present disclosure, the product must be sterile. Heat sterilizing is not applicable in the present disclosure, since both the nanoparticles and human serum albumin are sensitive to temperature. Thus feasible sterilization methods include aseptic production or sterilization filtration. In such cases, after removal of the organic solvent, the suspension is sterilized by passing through a filter, and subsequently, it is lyophilized to obtain a solid. The solid obtained is re-suspended in sodium chloride solution. In some embodiments, the solid is re-suspended in 0.9% sodium chloride solution to reach a paclitaxel concentration of about 5 mg/ml.

When the therapeutic nanoparticles are purified using centrifugation, removal of free HSA is performed at 21000×g for 60 min or at equivalent conditions.

When the therapeutic nanoparticles are purified by dialysis, the nanoparticle-containing suspension obtained in step 3) is dialyzed using an ultrafiltration membrane to remove free HSA. In particular embodiments, the nanoparticle liquid obtained according to the method of the present disclosure is dialyzed in equal volume of 5% mannitol solution using a regenerated cellulose ultrafiltration membrane with the cutoff molecular weight of 300K, and the dialysis fold is 5.

When therapeutic nanoparticles are purified using exclusion chromatography, therapeutic nanoparticles are separated from free HSA using an exclusion chromatographic column. In particular embodiments, nanoparticle-containing suspension obtained in step 3) is applied onto a sepharose column, and the eluting peak corresponding to therapeutic nanoparticles is collected.

In certain embodiments, the method further comprises between steps 3) and 4) a step of dialyzing the suspension of step 3) with an aqueous solution (e.g., water or 5% mannitol solution, 10% sucrose solution, 5% dextran solution, 10% lactose solution, 10% trehalose solution, and 10% maltose solution, etc) to remove the remaining organic solvent from the suspension. For example, the suspension may be dialyzed in water or an aqueous solution using an ultrafiltration membrane that allows the organic solvent to pass but not HSA or nanoparticles (e.g., a cellulose ultrafiltration membrane with a cutoff molecular weight of 30K). While not wishing to be bound by any theory, the removal or reduction of the remaining organic solvent prior to removal of free HSA from the nanoparticle-containing suspension may improve stability of purified nanoparticles or compositions thereof.

In another aspect, a method for preparing a pharmaceutical composition comprising the therapeutic nanoparticles is also provided. The method comprises:

1) dissolving the active ingredient in organic solvent to form an oil phase, and dissolving human serum albumin in water to form an aqueous phase;

2) forming an oil-in-water emulsion using the oil phase and aqueous phase;

3) removing the organic solvent in the emulsion to obtain a suspension containing the therapeutic nanoparticles;

4) removing free HSA that is not incorporated in the nanoparticles to obtain purified therapeutic nanoparticles;

5) re-suspending the purified therapeutic nanoparticles in a pharmaceutically acceptable carrier-containing solution to obtain the pharmaceutical composition; and 6) optionally lyophilizing the re-suspension of the purified therapeutic nanoparticles where the pharmaceutical composition is in the form of solid.

Steps 1) and 4) of this method are the same as described with respect to the method of preparing purified therapeutic nanoparticles. In addition, in certain embodiments, the method comprises between steps 3) and 4) a step of dialyzing the suspension of step 3) with an aqueous solution to remove the remaining organic solvent from the suspension also as described with respect to the method of preparing purified therapeutic nanoparticles.

In some embodiments, the pharmaceutically acceptable carrier-containing solution is the solution containing lyophilization excipient. In some specific embodiments, the lyophilization excipient is selected from one or more of mannitol, sucrose, lactose, maltose, trehalose, and dextran. In some other specific embodiments, the lyophilization excipient is HSA. In specific embodiments, the therapeutic nanoparticles are suspended in a solution of lyophilization excipient at the concentration from 5% to 10%.

Optionally, the pharmaceutical composition is prepared into lyophilized powder after lyophilization. In particular embodiments, the solution of lyophilization excipient is selected from one or more of 5% mannitol solution, 10% sucrose solution, 5% dextran solution, 10% lactose solution, 10% trehalose solution, 10% maltose solution, and 10% human serum albumin solution.

In some specific embodiments, the content of the therapeutic nanoparticles in the pharmaceutical composition in liquid form is from 0.1% to 30%, and preferably, from 0.2% to 10%, and more preferably, from 0.5% to 5%, for example, 1%. In some specific embodiments, the content of the active ingredient (for example, paclitaxel) in the pharmaceutical composition in liquid form of the present disclosure is from 0.1 to 100 mg/ml, and preferably, from 0.5 to 50 mg/ml, and more preferably, from 1 to 20 mg/ml, for example, 5 mg/ml.

In certain embodiments, the content of the therapeutic nanoparticles in the pharmaceutical composition in solid form is from 0.1% to 80% by weight, and preferably, from 0.5% to 50%, and more preferably, from 1% to 30%, for example, from 2% to 10%.

In some specific embodiments, the content of the active pharmaceutical ingredient (for example, paclitaxel) in the pharmaceutical composition in liquid form is from 0.1% to 80% by weight, and preferably, from 0.5% to 50%, and more preferably, from 1% to 30%, for example, from 2% to 10%.

Alternatively, the pharmaceutical composition of the present disclosure can be prepared using another procedure of dialysis. The method comprises:

1) dissolving the active ingredient in organic solvent to form an oil phase, and dissolving human serum albumin in water to form a aqueous phase;

2) forming an oil-in-water emulsion using the oil phase and aqueous phase above;

3) removing the organic solvent in the emulsion to obtain a suspension containing the therapeutic nanoparticles;

4) dialyzing the suspension obtained after removal of the organic solvent by a pharmaceutically acceptable carrier-containing solution to remove free HSA that is not incorporated in the nanoparticles; and 5) optionally lyophilizing the dialyzed suspension when the pharmaceutical composition is prepared in the form of solid.

Steps 1) and 4) of this method are the same as described with respect to the method of preparing purified therapeutic nanoparticles when dialysis is used to remove free HSA. In addition, in certain embodiments, the method comprises between steps 3) and 4) a step of dialyzing the suspension of step 3) with an aqueous solution to remove the remaining organic solvent from the suspension also as described with respect to the method of preparing purified therapeutic nanoparticles.

In some embodiments, a pharmaceutically acceptable carrier-containing solution is used as the dialysate, which is the lyophilization excipient-containing solution. In some specific embodiments, the lyophilization excipient is selected from one or more of mannitol, sucrose, lactose, maltose, trehalose, and dextran.

In specific embodiments, the therapeutic nanoparticles are suspended in a solution of lyophilization excipient with the concentration from 5% to 10%. Optionally, the pharmaceutical composition is prepared into lyophilized powder after lyophilization. In particular embodiments, the solution of lyophilization excipient is selected from one or more of 5% mannitol solution, 10% sucrose solution, 5% dextran solution, 10% lactose solution, 10% trehalose solution, 10% maltose solution, and 10% human serum albumin solution. In some embodiments, dialysis is performed using an ultrafiltration membrane with cutoff molecular weight of 300 k.

In another aspect, the present disclosure provides methods for using the purified therapeutic nanoparticles or compositions thereof. Because the present purified nanoparticles or compositions are effective means for delivering various active ingredients, they may be used for treating any diseases or disorders that are responsive to the active ingredients. For example, the purified therapeutic nanoparticles or compositions thereof may be used in treating cancer, such as liver cancer, prostatic cancer and lung cancer. Additional diseases or disorders that may be treated include breast cancer, multiple myeloma, transplant rejection, colon cancer, lymphoma, fever, etc.

In a particular aspect, the present disclosure provides a method for treating cancer that comprises administering a therapeutically effective amount of a pharmaceutical composition provided herein to a subject in need thereof. In specific embodiments, the subject is a mammal, including but not limited to human, canine, mouse, and rat.

A therapeutically effective amount of a pharmaceutical composition may be determined or adjusted depending on various factors including the specific therapeutic agents or pharmaceutical compositions, the routes of administration, the subject's condition, that is, stage of the disease, severity of symptoms caused by the disease, general health status, as well as age, gender, and weight, and other factors apparent to a person skilled in the medical art. Similarly, the dose of the therapeutic for treating a disease or disorder may be determined according to parameters understood by a person skilled in the medical art. Optimal doses may generally be determined using experimental models and/or clinical trials.

The pharmaceutical composition may be administered via through any suitable routes, for example, oral, nasal, intracutaneous, subcutaneous, intramuscular or intravenous administration.

In another aspect, a pharmaceutical kit is also provided in the present disclosure, which comprises purified therapeutic nanoparticles or a pharmaceutical composition thereof provided herein. If required, the pharmaceutical kit also comprises instruction, package, and a container holding the therapeutic nanoparticles or the pharmaceutical composition.

EXAMPLES

The Examples below were intended to better illustrate the therapeutic nanoparticles and the pharmaceutical composition disclosed herein, and not to limit any aspect of the present disclosure.

Example 1

3 g paclitaxel (CAS: 33069-62-4, Yunnan Hande Bio-Tech Co., Ltd) was dissolved into 20 ml chloroform/ethanol (9:1, v/v), and added into 500 ml human serum albumin solution (5% w/v) (CAS: 70024-90-7, Guangdong Shuanglin Biopharmaceutical. Co., Ltd.). The mixture was emulsified for 2 min using a high shear disperser (Model F22E, Fluko Co., Ltd., Shanghai) to obtain a primary emulsion. The primary emulsion was then homogenized using a high pressure homogenizer (Model M110-EH30K, MFIC Company, USA) under pressure of 10000-20000 psi to obtain a nano-emulsion. Subsequently, the nano-emulsion was transferred to a rotatory evaporator (Model R-210, Buchi Company, Switzerland) to remove the organic solvent in the solution by vacuum evaporation at 40 mbar and at 40° C. in a water-bath. The paclitaxel-albumin nanoparticles were thus generated with an average diameter of 136 nm, and the suspension was translucent.

The suspension can be smoothly filtered through a 0.22 µm sterile filter (Sartorius AG, Germany). There was no significant variation of the particle size after filtration, and no significant change was observed after storage for 48 h at room temperature. The suspension was aliquoted and lyophilized for 24 h in a lyophilizer (Model LD-855, Millrock, USA) to obtain a stable off-white cake.

Example 2

0.32 g paclitaxel (CAS: 33069-62-4, Yunnan Hande Bio-Tech Co., Ltd) was dissolved into 15 ml chloroform/ethanol (11:1, v/v), and added into which 500 ml human serum albumin solution (4% w/v) (CAS: 70024-90-7, Guangdong Shuanglin Biopharmaceutical. Co., Ltd.). The mixture was emulsified for 2 min using a high shear disperser (Model F22E, Fluko Co., Ltd., Shanghai) to obtain a primary emulsion. The primary emulsion was then homogenized using a high pressure homogenizer (Model M110-EH30K, MFIC Company, USA) under a pressure of 10000-20000 psi to obtain a nano-emulsion. Subsequently, the nano-emulsion was transferred to a rotatory evaporator (Model R-210, Buchi Company, Switzerland) to remove the organic solvent in the solution by vacuum evaporation at 40 mbar and at 40° C. in a water-bath. The paclitaxel-albumin nanoparticles were thus generated with an average diameter of 145 nm, and the suspension was translucent.

The suspension can be smoothly filtered through a 0.22 µm sterile filter (Sartorius AG, Germany). There was no significant variation of the particle size after filtration, and no significant change was observed after storage for 48 h at room temperature. The suspension was aliquoted and lyophilized for 24 h in a lyophilizer (Model LD-85S, Millrock, USA) to obtain a stable off-white cake.

Example 3

0.63 g paclitaxel (CAS: 33069-62-4, Yunnan Hande Bio-Tech Co., Ltd) was dissolved into 15 ml chloroform/ethanol (11:1, v/v), and added into 500 ml human serum albumin solution (4% w/v) (CAS: 70024-90-7, Guangdong Shuanglin Biopharmaceutical. Co., Ltd.). The mixture was emulsified for 2 min using a high shear disperser (Fluko FZ-20) to obtain a primary emulsion. The primary emulsion was then homogenized using a high pressure homogenizer (Model M110-EH30K, MFIC Company, USA) under a pressure of 10000-20000 psi to obtain a nano-emulsion. Subsequently, the nano-emulsion was transferred to a rotatory evaporator (Model R-210, Buchi Company, Switzerland) to remove the organic solvent in the solution by vacuum evaporation at 40 mbar and at 40° C. in a water-bath. The paclitaxel-albumin nanoparticles were thus generated with an average diameter of 141 nm, and the suspension was translucent.

The suspension can be smoothly filtered through a 0.22 µm sterile filter (Sartorius AG, Germany). There was no significant variation of the particle size after filtration, and no significant change was observed after storage for 48 h at room temperature. The suspension was aliquoted and lyophilized for 24 h in a lyophilizer (Model LD-85S, Millrock, USA) to obtain a stable off-white cake.

Example 4

1.25 g paclitaxel (CAS: 33069-62-4, Yunnan Hande Bio-Tech Co., Ltd) was dissolved into 15 ml chloroform/ethanol (11:1, v/v), and added into which 500 ml human serum albumin solution (4% w/v) (CAS: 70024-90-7, Guangdong Shuanglin Biopharmaceutical. Co., Ltd.). The mixture was emulsified for 2 min using a high shear disperser (Model F22Z, Fluko Co., Ltd., Shanghai) to obtain a primary emulsion. The primary emulsion was then homogenized using a high pressure homogenizer (Model M110-EH30K, MFIC Company, USA) under a pressure of 10000-20000 psi to obtain a nano-emulsion. Subsequently, the nano-emulsion was transferred to a rotatory evaporator (Model R-210, Buchi Company, Switzerland) to remove the organic solvent in the solution by vacuum evaporation at 40 mbar and at 40° C. in a water-bath. The paclitaxel-albumin nanoparticles were thus generated with an average diameter of 138 nm, and the suspension was translucent.

The suspension can be smoothly filtered through a 0.22 µm sterile filter (Sartorius AG, Germany). There was no significant variation of the particle size after filtration, and no significant change was observed after storage for 48 h at room temperature. The suspension was aliquoted and lyophilized for 24 h in a lyophilizer (Model LD-85S, Millrock, USA) to obtain a stable off-white cake.

Example 5

1.88 g paclitaxel (CAS: 33069-62-4, Yunnan Hande Bio-Tech Co., Ltd) was dissolved into 15 ml chloroform/ethanol (11:1, v/v), and added into which 500 ml human serum albumin solution (4% w/v) (CAS: 70024-90-7, Guangdong Shuanglin Biopharmaceutical. Co., Ltd.). The mixture was emulsified for 2 min using a high shear disperser (Fluko FZ-20) to obtain a primary emulsion. The primary emulsion was then homogenized using a high pressure homogenizer (Model M110-EH30K, MFIC Company, USA) under a pressure of 10000-20000 psi to obtain a nano-emulsion. Subsequently, the nano-emulsion was transferred to a rotatory evaporator (Model R-210, Buchi Company, Switzerland) to remove the organic solvent in the solution by vacuum evaporation at 40 mbar and at 40° C. in a waterbath. The paclitaxel-albumin nanoparticles were thus generated with an average diameter of 133 nm, and the suspension was translucent.

The suspension can be smoothly filtered through a 0.22 µm sterile filter (Sartorius AG, Germany). There was no significant variation of the particle size after filtration, and no significant change was observed after storage for 48 h at room temperature. The suspension was aliquoted and lyophilized for 24 h in a lyophilizer (Model LD-85S, Millrock, USA) to obtain a stable off-white cake.

Example 6

2.5 g paclitaxel (CAS: 33069-62-4, Yunnan Hande Bio-Tech Co., Ltd) was dissolved into 15 ml chloroform/ethanol (11:1, v/v), and added into which 500 ml human serum albumin solution (4% w/v) (CAS: 70024-90-7, Guangdong Shuanglin Biopharmaceutical. Co., Ltd.). The mixture was emulsified for 2 min using a high shear disperser (Fluko FZ-20) to obtain a primary emulsion. The primary emulsion was then homogenized using a high pressure homogenizer (Model M110-EH30K, MFIC Company, USA) under a pressure of 10000-20000 psi to obtain a nano-emulsion. Subsequently, the nano-emulsion was transferred to a rotatory evaporator (Model R-210, Buchi Company, Switzerland) to remove the organic solvent in the solution by vacuum evaporation at 40 mbar and at 40° C. in a waterbath. The paclitaxel-albumin nanoparticles were thus generated with an average diameter of 125 nm, and the suspension was translucent.

The suspension can be smoothly filtered through a 0.22 µm sterile filter (Sartorius AG, Germany). There was no significant variation of the particle size after filtration, and no significant change was observed after storage for 48 h at room temperature. The suspension was aliquoted and lyophilized for 24 h in a lyophilizer (Model LD-85S, Millrock, USA) to obtain a stable off-white cake.

Example 7

5 g paclitaxel (CAS: 33069-62-4, Yunnan Hande Bio-Tech Co., Ltd) was dissolved into 15 ml chloroform/ethanol (11:1, v/v), and added into which 500 ml human serum albumin solution (4% w/v) (CAS: 70024-90-7, Guangdong Shuanglin Biopharmaceutical. Co., Ltd.). The mixture was emulsified for 2 min using a high shear disperser (Fluko FZ-20) to obtain a primary emulsion. The primary emulsion was then homogenized using a high pressure homogenizer (Model M110-EH30K, MFIC Company, USA) under a pressure of 10000-20000 psi to obtain a nano-emulsion. Subsequently, the nano-emulsion was transferred to a rotatory evaporator (Model R-210, Buchi Company, Switzerland) to remove the organic solvent in the solution by vacuum evaporation at 40 mbar and at 40° C. in a waterbath. The paclitaxel-albumin nanoparticles were thus generated with an average diameter of 134 nm, and the suspension was translucent.

The suspension can be smoothly filtered through a 0.22 µm sterile filter (Sartorius AG, Germany). There was no significant variation of the particle size after filtration, and no significant change was observed after storage for 48 h at room temperature. The suspension was aliquoted and lyophilized for 24 h in a lyophilizer (Model LD-85S, Millrock, USA) to obtain a stable off-white cake.

Example 8

7.5 g paclitaxel (CAS: 33069-62-4, Yunnan Hande Bio-Tech Co., Ltd) was dissolved into 15 ml chloroform/ethanol (11:1, v/v), and added into which 500 ml human serum albumin solution (4% w/v) (CAS: 70024-90-7, Guangdong Shuanglin Biopharmaceutical. Co., Ltd.). The mixture was emulsified for 2 min using a high shear disperser (Fluko FZ-20) to obtain a primary emulsion. The primary emulsion was then homogenized using a high pressure homogenizer (Model M110-EH30K, MFIC Company, USA) under a pressure of 10000-20000 psi to obtain a nano-emulsion. Subsequently, the nano-emulsion was transferred to a rotatory evaporator (Model R-210, Buchi Company, Switzerland) to remove the organic solvent in the solution by vacuum evaporation at 40 mbar and at 40° C. in a waterbath. The paclitaxel-albumin nanoparticles were thus generated with an average diameter of 140 nm, and the suspension was translucent.

The suspension can be smoothly filtered through a 0.22 µm sterile filter (Sartorius AG, Germany). There was no significant variation of the particle size after filtration, and no significant change was observed after storage for 48 h at room temperature. The suspension was aliquoted and lyophilized for 24 h in a lyophilizer (Model LD-85S, Millrock, USA) to obtain a stable off-white cake.

Example 9

1 g paclitaxel (CAS: 33069-62-4, Yunnan Hande Bio-Tech Co., Ltd) was dissolved into 20 ml chloroform/ethanol (4:1, v/v), and added into which 500 ml human serum albumin solution (2% w/v) (CAS: 70024-90-7, Guangdong Shuanglin Biopharmaceutical. Co., Ltd.). The mixture was emulsified for 2 min using a high shear disperser (Fluko FZ-20) to obtain a primary emulsion. The primary emulsion was then homogenized using a high pressure homogenizer (Model M110-EH30K, MFIC Company, USA) under a pressure of 10000-20000 psi to obtain a nano-emulsion. Subsequently, the nano-emulsion was transferred to a rotatory evaporator (Model R-210, Buchi Company, Switzerland) to remove the organic solvent in the solution by vacuum evaporation at 40 mbar and at 40° C. in a waterbath. The paclitaxel-albumin nanoparticles were thus generated with an average diameter of 136 nm, and the suspension was translucent.

The suspension can be smoothly filtered through a 0.22 µm sterile filter (Sartorius AG, Germany). There was no significant variation of the particle size after filtration, and no significant change was observed after storage for 48 h at room temperature. The suspension was aliquoted and lyophilized for 24 h in a lyophilizer (Model LD-85S, Millrock, USA) to obtain a stable off-white cake.

Example 10. Determination Methods for the Content of Human Serum Albumin and Paclitaxel The content of human serum albumin was determined by HPLC. The human serum albumin was determined at a wavelength of 228 nm in an HPLC equipped with a Tosohaas TSK G3000 SWXL gel column and a UV-detector (1260VWD G1314B, Agilent technologies), with a mobile phase of 0.1 mol/L dipotassium hydrogen phosphate solution and an injection volume of 10 µl. The albumin content was calculated using the external standard method.

Preparation of the test solutions: the test solutions were prepared by diluting the solution for determination using 0.9% sodium chloride solution to an albumin concentration lower than 3 mg/ml.

The content of paclitaxel was determined by HPLC. The paclitaxel was determined at a wavelength of 228 nm in an HPLC equipped with a C18 reverse phase column and a UV-detector (1260VWD G1314B, Agilent technologies), with a mobile phase of acetonitrile-water (1:1, v/v) and an injection volume of 10 µl. The paclitaxel content was calculated using the external standard method.

Preparation of the test solutions: the test solutions were prepared by diluting the solution for determination using acetonitrile until full dissolution of paclitaxel, with the concentration of 20-200 µg/ml.

Example 11

The product obtained in Example 1 was reconstituted in a 0.9% sodium chloride solution to obtain sample 1, with the paclitaxel content of 5 mg/ml. Subsequently, sample 1 was diluted using simulated blood plasma containing 5% albumin, so that the paclitaxel content may reach 20 µg/ml to obtain sample 2 (particles were completely disintegrated under such condition, and no paclitaxel-human serum albumin bound particles exist). 1 ml sample 1 and 1 ml sample 2 were centrifuged at 21000×g for various durations, respectively. The concentrations of paclitaxel and albumin in the supernatant were determined using the methods mentioned in Example 10, and the results are listed in table 1.

TABLE 1

The concentrations of paclitaxel and albumin in the supernatant under different centrifugation durations

| Centrifugation duration (min) | Sample 1 5 mg/ml solution | | | | Sample 2 20 µg/ml solution | | | |
|---|---|---|---|---|---|---|---|---|
| | Albumin (mg/ml) | % | Paclitaxel (mg/ml) | % | Albumin (mg/ml) | % | Paclitaxel (mg/ml) | % |
| 0 | 42.8 | 100.0* | 5.01 | 100.0* | 52.7 | 100.0* | 0.0217 | 100.0* |
| 20 | 44.2 | 103.2 | 0.78 | 15.6 | 53.1 | 100.8 | 0.0218 | 99.5 |
| 40 | 45.2 | 105.6 | 0.38 | 7.7 | 52.2 | 99.0 | 0.0220 | 101.3 |
| 80 | 44.9 | 104.9 | 0.11 | 2.1 | 53.5 | 101.6 | 0.0218 | 100.6 |
| 80 | 45.3** | 105.8 | 0.11 | 2.1 | 53.5 | 101.5 | 0.0219 | 100.9 |

Note*:
the percentage contents of albumin and paclitaxel in supernatant were both calculated based on the concentration at 0 min (100%).
Note**:
After reconstitution, the concentration of albumin increased since the solution volume was reduced to 90% of its initial volume due to precipitation after centrifugation of the suspension.

It was suggested that no precipitation was generated after centrifugation for the sample fully disintegrated (Sample 2). No significant variations of the paclitaxel and albumin concentrations in supernatant were observed for different centrifugation durations, i.e., there was no paclitaxel crystal or heavy particle in the solution.

Precipitate occurred at the bottom after centrifugation for the non-disintegrated sample (Sample 1). The paclitaxel concentration in supernatant decreased with centrifugation time, and finally reached equilibrium. The albumin concentration slightly increased with time, and finally reached equilibrium (the volume of the supernatant was about 90% of the total volume). In conclusion, the nanoparticles in the sample can be isolated and purified by centrifugation.

After centrifugation for 60 min, the paclitaxel concentration in supernatant reached equilibrium. Thus, paclitaxel-albumin particles can be isolated at 21000×g for 60 min.

Example 12. Preparation of the Nanoparticles

Using the centrifugation method mentioned in Example 11, particles were isolated from the samples obtained in Example 1-9. After centrifugation, the supernatants were discarded, and the precipitates thus obtained were the paclitaxel-albumin nanoparticles, which were referred as particle 1, 2, 3, 4, 5, 6, 7, 8, and 9, corresponding to Example 1-9.

Figure 2:
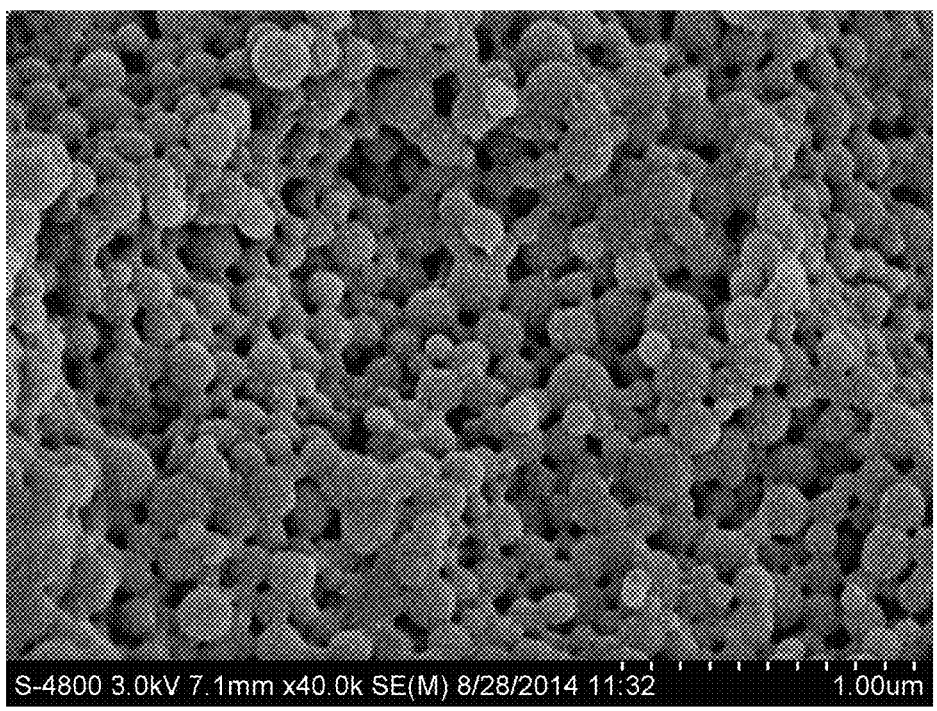
FIG. 2. Scanning electron microscopic image of the nanoparticles prepared using purified from the sample of Example 5.

Example 13. Scanning Electron Microscopic Observation on Morphology of the Particles Before and after Separation Lyophilized powder of the sample obtained in Example 5, and the precipitate from Example 5 obtained in Example 12 (particle 5) were observed under a scanning electron microscope (S-4800, Hitachi). It can be seen from the result in FIG. 1 that a small amount of particles in the sample from Example 5 were embedded in the support agent formed by a great amount of albumin. While for Particle 5, these particles existed independently (See FIG. 2). It can thus be confirmed that the precipitate obtained using the separation method in Example 11 was pure or substantially pure nanoparticles.

Example 14. The Ratio Between Albumin and Paclitaxel in the Particle

The paclitaxel-albumin nanoparticles (corresponding to Example 1-9) obtained in Example 12 were re-suspended respectively in 1 ml 0.9% sodium chloride solution. The contents of paclitaxel and albumin in the samples were each determined using the method in Example 10, and the results are as follows:

TABLE 2

The ratio between albumin and paclitaxel in various purified nanoparticles obtained after centrifugation

| | Concentration in oil phase (mg/ml) | Albumin content (mg/ml) | Paclitaxel content (mg/ml) | Albumin:Paclitaxel |
|---|---|---|---|---|
| Example 8 | 500 | 0.24 | 5.58 | 0.043:1 |
| Example 7 | 333 | 0.38 | 5.34 | 0.071:1 |
| Example 6 | 167 | 0.65 | 5.03 | 0.13:1 |
| Example 1 | 150 | 0.76 | 5.04 | 0.15:1 |
| Example 5 | 125 | 0.83 | 5.16 | 0.16:1 |
| Example 9 | 50 | 0.86 | 5.03 | 0.17:1 |
| Example 4 | 83 | 0.82 | 4.56 | 0.18:1 |
| Example 3 | 42 | 1.11 | 4.63 | 0.24:1 |
| Example 2 | 21 | 2.10 | 3.69 | 0.57:1 |

It has been suggested by the results above that the ratios between albumin and paclitaxel in the purified nanoparticles from the products obtained using different formulation process were different, and they have certain regularity. It also can be seen that increased concentration of paclitaxel in oil phase was inversely proportional to the albumin content.

Example 15. Preparation of Purified Nanoparticles Using Dialysis

Dialysis was conducted in equal volume to the samples prepared in Example 2, Example 5, and Example 8 after reconstituted by water for injection against the dialysis solution of 5% mannitol using a regenerated cellulose ultrafiltration membrane (PXC300C50, Millipore) with the cut-off molecular weight of 300K, and the dialysis fold was 5. The contents of paclitaxel and albumin in the samples were determined after dialysis using the method in Example 10, and the results are as follows:

TABLE 3

The ratios between albumin and paclitaxel in the purified nanoparticles from various formulations obtained by dialysis

|  | Albumin content (mg/ml) | Paclitaxel content (mg/ml) | Albumin:Paclitaxel |
|---|---|---|---|
| Example 8 | 0.25 | 5.12 | 0.048:1 |
| Example 5 | 0.73 | 4.85 | 0.15:1 |
| Example 2 | 2.19 | 3.71 | 0.59:1 |

The above results have indicated a substantially similar weight ratio between albumin and paclitaxel in the particles obtained by dialysis using an ultrafiltration membrane, as compared to the particles obtained by centrifugation. As a result, dialysis using an ultrafiltration membrane also can be used for isolating the particles in the suspension from excessive albumin, and for replacement of the solution surrounding the particles.

Example 16. Preparation of Purified Nanoparticles on Chromatographic Column 20 ml Sepharose 4B gel was packed in a glass column with diameter of 10 mm (Φ10 mm*230 mm, Beijing Mancang Technology Ltd.). The column was equilibrated with 0.9% sodium chloride solution to 3 times of the column volumes. 1 ml samples prepared in Example 2, Example 5, and Example 8 were loaded on the top of the gel column, and eluted using 0.9% sodium chloride solution, respectively. The effluent was on-line monitored using a UV-detector at the wavelength of 280 nm. The effluent corresponding to the first peak on the chromatogram was a slightly cloudy suspension, which was collected for determination of paclitaxel and albumin. Recording was continued until the second peak was finished. Both peaks were well separated, indicating that the particles and free albumin can be effectively separated using the Sepharose 4B gel column. The contents of paclitaxel and albumin in the particles were determined using the method in Example 10, and the results are as follows:

TABLE 4

The ratios between albumin and paclitaxel in the purified nanoparticles from various formulations obtained by separation on a chromatographic column

|  | Albumin content (mg/ml) | Paclitaxel content (mg/ml) | Albumin:Paclitaxel |
|---|---|---|---|
| Example 8 | 0.10 | 2.51 | 0.041:1 |
| Example 5 | 0.33 | 2.33 | 0.14:1 |
| Example 2 | 0.68 | 1.23 | 0.55:1 |

The above results indicated a substantially similar weight ratio between albumin and paclitaxel in the particles obtained by separation on a gel column, as compared to the particles obtained by centrifugation and dialysis. As a result, gel column separation also can be used for isolating the particles in the suspension from excessive albumin.

Example 17. Determination of the Free Albumin Content in the Purified Nanoparticles Prepared by Dialysis Using Centrifugation The particle suspension obtained by dialysis in Example 15 was further isolated by centrifugation under the conditions of Example 11. After all particles were precipitated at the bottom of the centrifuge tube, the albumin concentration in the supernatant was determined, and the results are listed in Table 5.

TABLE 5

The variation of albumin concentration in the purified nanoparticles from various formulations obtained by dialysis before and after centrifugation

|  | Concentration before centrifugation (mg/ml) | Concentration in the supernatant after centrifugation (mg/ml) |
|---|---|---|
| Example 2 | 2.19 | 0.02 |
| Example 5 | 0.73 | 0.01 |
| Example 8 | 0.25 | ND |

ND stands for lower than the limit of determination, i.e., not detected.

It can be seen from the above results that in the paclitaxel-albumin nanoparticle suspension obtained by dialysis, the proportion of free albumin was quite low, and most albumin was bound to paclitaxel to form nanoparticles.

Example 18. Determination of the Free Albumin Content in the Purified Nanoparticles Prepared by Chromatographic Column Separation Using Centrifugation The particle suspension obtained by chromatographic column separation in Example 16 was further subjected to centrifugation under the conditions of Example 11. After all particles were precipitated at the bottom of the centrifuge tube, the albumin concentration in the supernatant was determined, and the results are listed in Table 6.

TABLE 6

The variation of albumin concentration in the purified
nanoparticles from various formulations obtained by
chromatographic column separation before and after centrifugation

|  | Concentration before centrifugation (mg/ml) | Concentration in the supernatant after centrifugation (mg/ml) |
| --- | --- | --- |
| Example 2 | 0.68 | ND |
| Example 5 | 0.33 | ND |
| Example 8 | 0.10 | ND |

ND stands for lower than the limit of determination, i.e., not detected.

It can be seen from the above results that in the paclitaxel-albumin nanoparticle suspension obtained by chromatographic column separation, there was almost no free albumin, and most albumin was bound to paclitaxel to form nanoparticles.

Example 19. Determination of the Free Albumin Content in the Purified Nanoparticles Prepared by Centrifugation Using Chromatographic Column Separation A particle suspension was obtained by re-suspending the paclitaxel-albumin nanoparticles obtained in Example 12 in 0.9% sodium chloride solution, and the purified nanoparticles and free albumin (if any) were separated from each other using Sepharose 4B column as mentioned in Example 16. During elution, the UV absorbance curve was monitored. After the particles were completely eluted, the following eluent was collected, in which the albumin concentration was determined. The results are listed in Table 7.

TABLE 7

The variation of albumin concentration in the purified
nanoparticles from various formulations obtained by
centrifugation before and after chromatographic column separation

|  | Concentration before column separation (mg/ml) | Albumin concentration after column separation (mg/ml) |
| --- | --- | --- |
| Example 2 | 0.57 | ND |
| Example 5 | 0.16 | ND |
| Example 8 | 0.043 | ND |

ND stands for lower than the limit of determination, i.e., not detected.

It can be seen from the above results that in the paclitaxel-albumin nanoparticle suspension obtained by centrifugation, there was almost no free albumin, and most albumin was bound to paclitaxel to form nanoparticles. In Example 17, 18, and 19, it can be demonstrated by the evidences observed in three isolation measures that purified nanoparticles can be obtained by all three measures with almost no free albumin.

Example 20. Determination of Particle Size and Potential

Paclitaxel-albumin nanoparticles obtained in Example 12 (corresponding to Example 1-9) were each re-suspended in purified water. The particle size and the zeta potential of the purified nanoparticles were detected using Malven NANO-ZS laser particle sizer, and the results are listed below:

TABLE 8

The particle size and the potential of the purified nanoparticles
after centrifugation

|  | Initial average particle size (nm) | Average particle size of the pure particle (nm) | Zeta potential of the pure particle (mV) |
| --- | --- | --- | --- |
| Example 6 | 125 | 126.6 | −28.7 |
| Example 5 | 133 | 132 | −27.1 |
| Example 7 | 134 | 127.5 | −37 |
| Example 1 | 136 | 137 | −28.1 |
| Example 9 | 136 | 137.4 | −33.6 |
| Example 4 | 138 | 138.7 | −34.2 |
| Example 8 | 140 | 139 | −39.4 |
| Example 3 | 141 | 151.2 | −27.5 |
| Example 2 | 145 | 145 | −33 |

It can be seen from the results that the average particle size of the purified nanoparticles obtained after centrifugation was substantially the same as its initial average particle size, and the zeta potential was still relatively high, so that the charge can be employed to stabilize the particle suspension.

Example 21. X Diffraction Pattern

Figure 3:
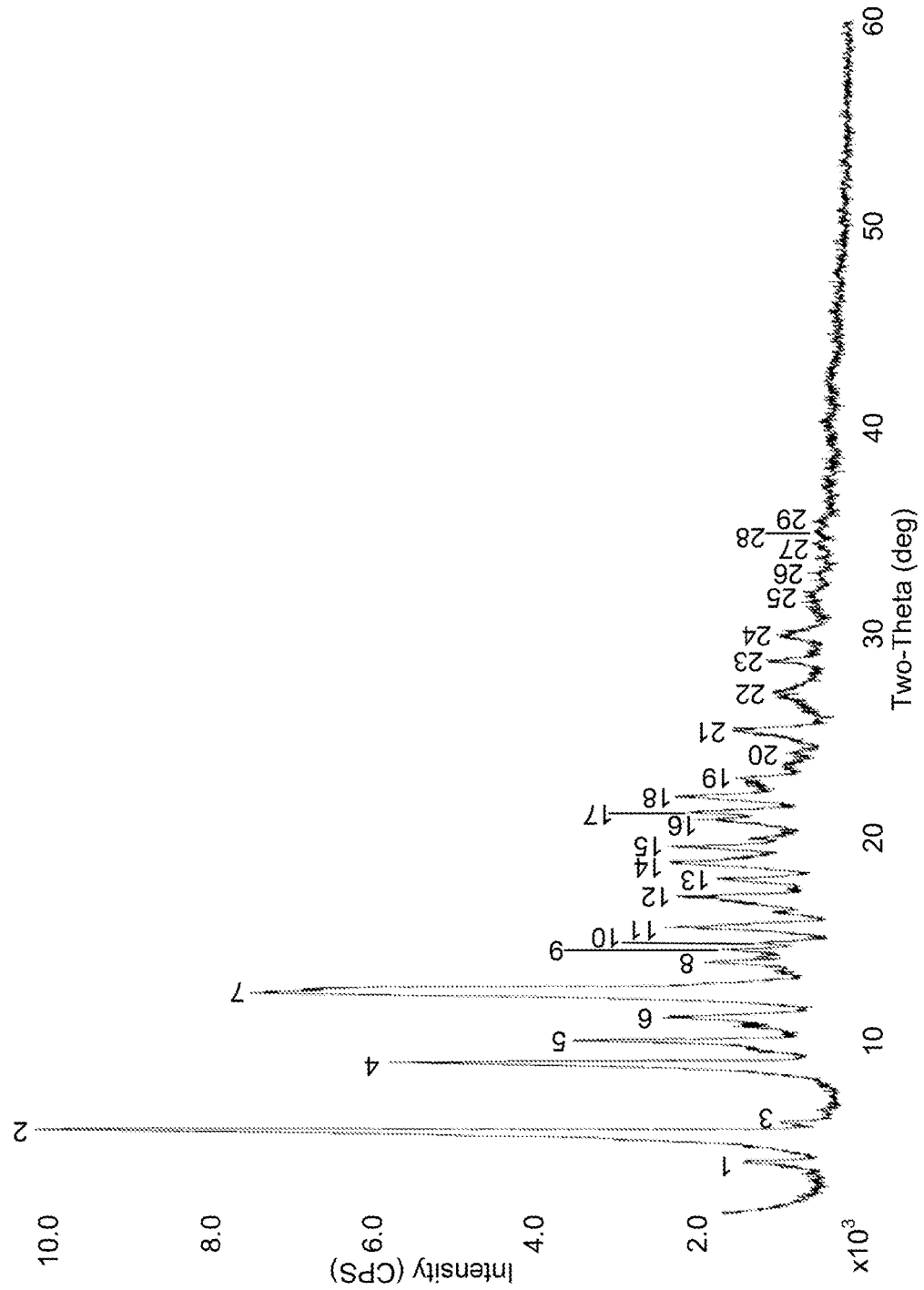
FIG. 3. X diffraction pattern of paclitaxel.
Figure 4:
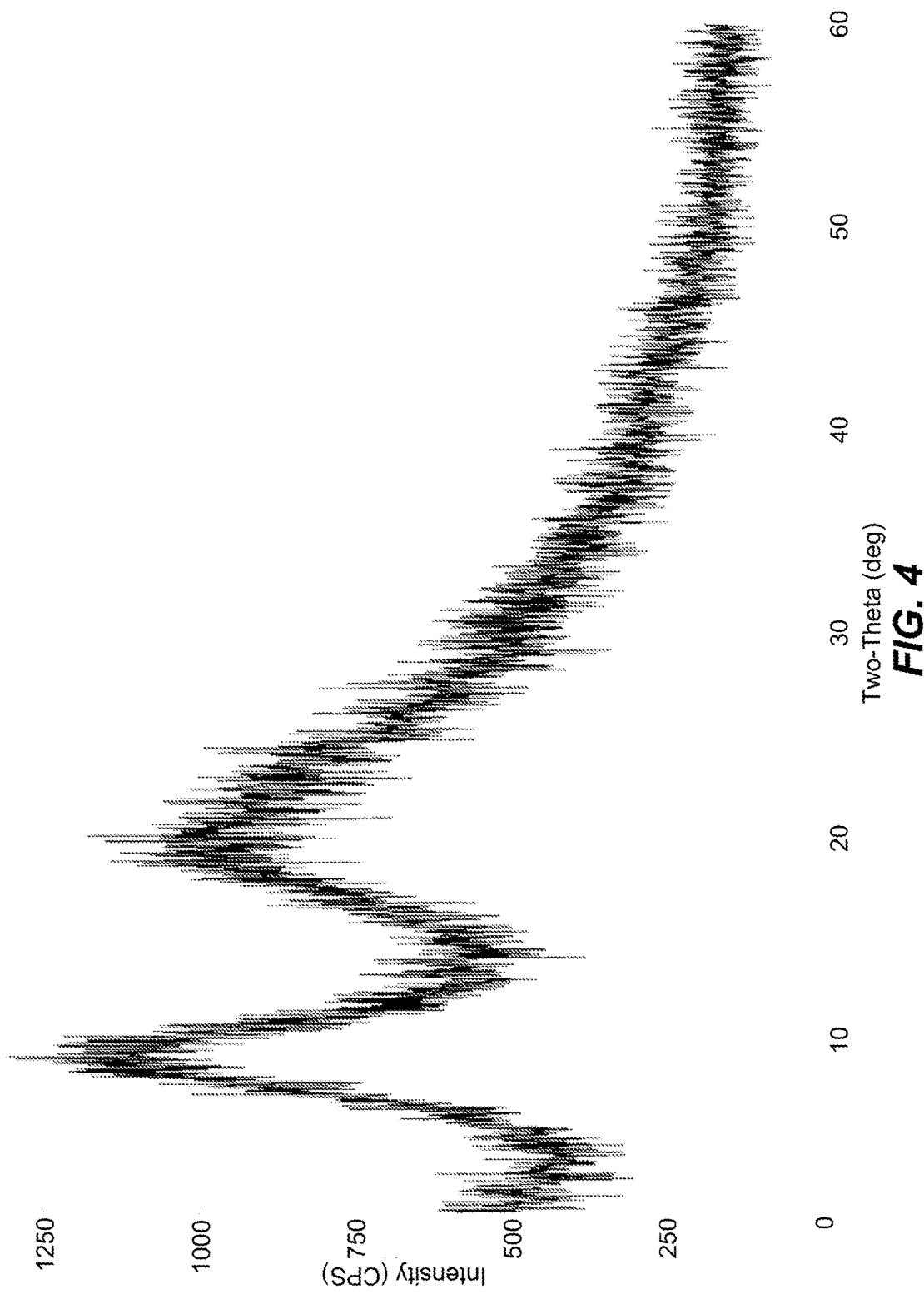
FIG. 4. X diffraction pattern of lyophilized powder of albumin.
Figure 5:
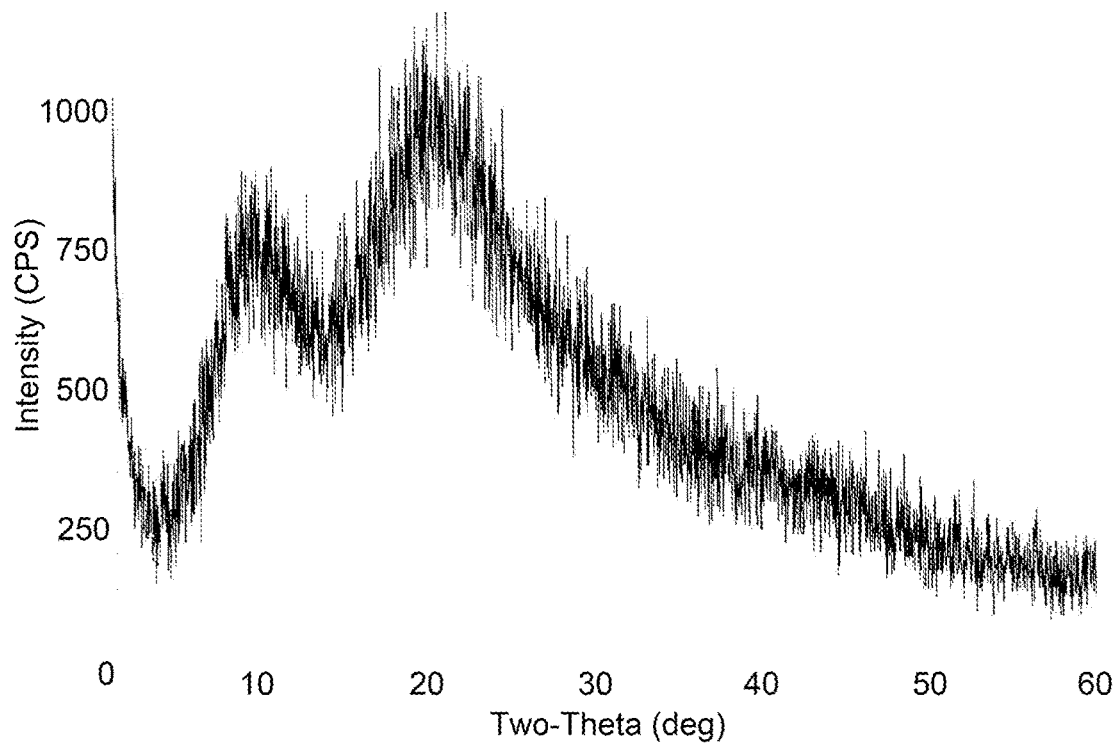
FIG. 5. X diffraction pattern of the paclitaxel-albumin nanoparticles corresponding to Example 2.
Figure 6:
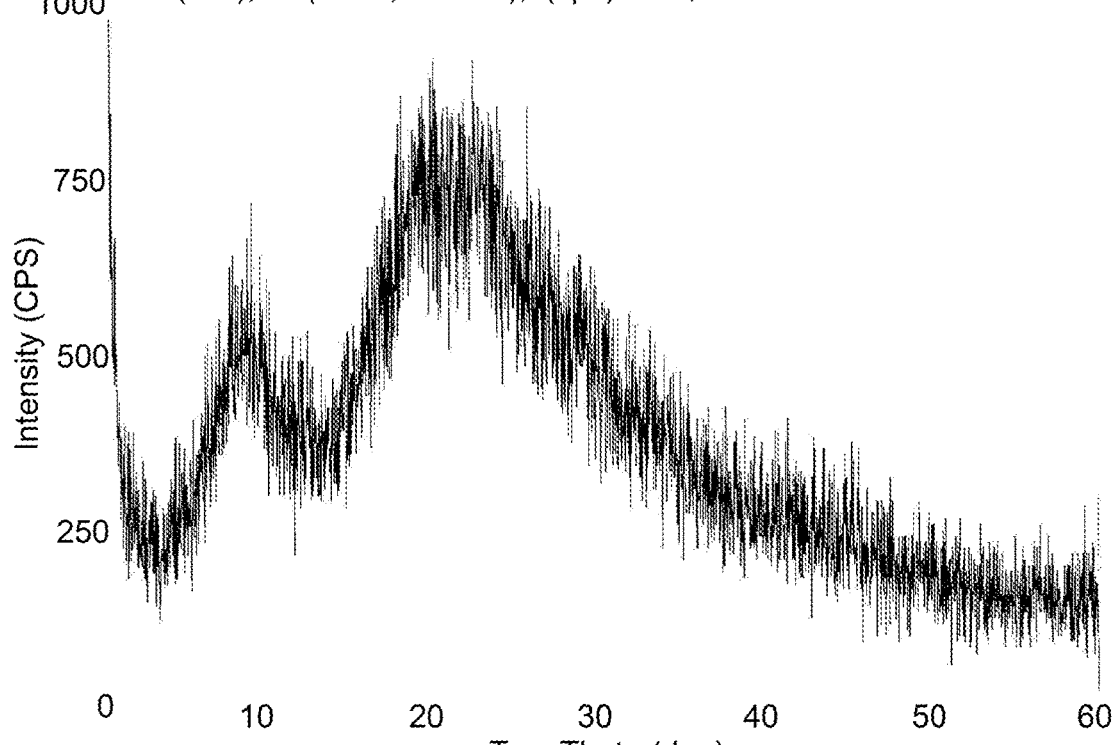
FIG. 6. X diffraction pattern of the paclitaxel-albumin nanoparticles corresponding to Example 4.
Figure 7:
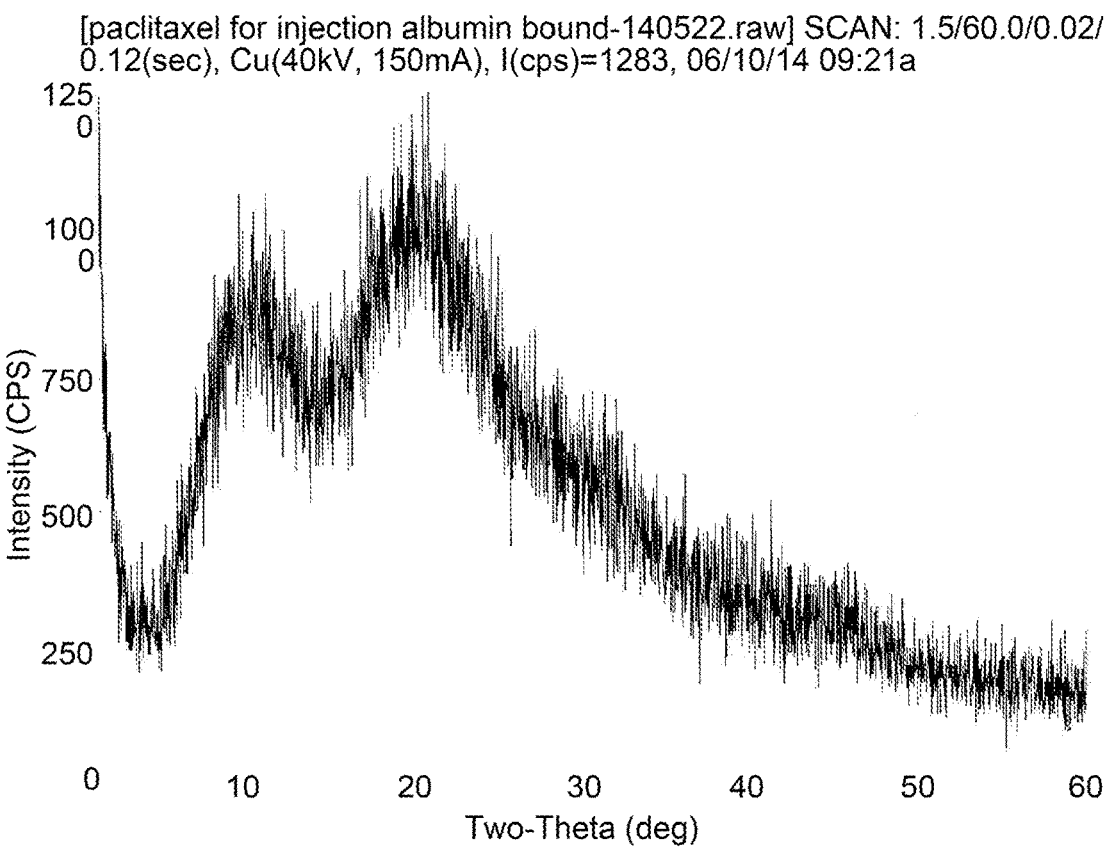
FIG. 7. X diffraction pattern of the paclitaxel-albumin nanoparticles corresponding to Example 6.
Figure 8:
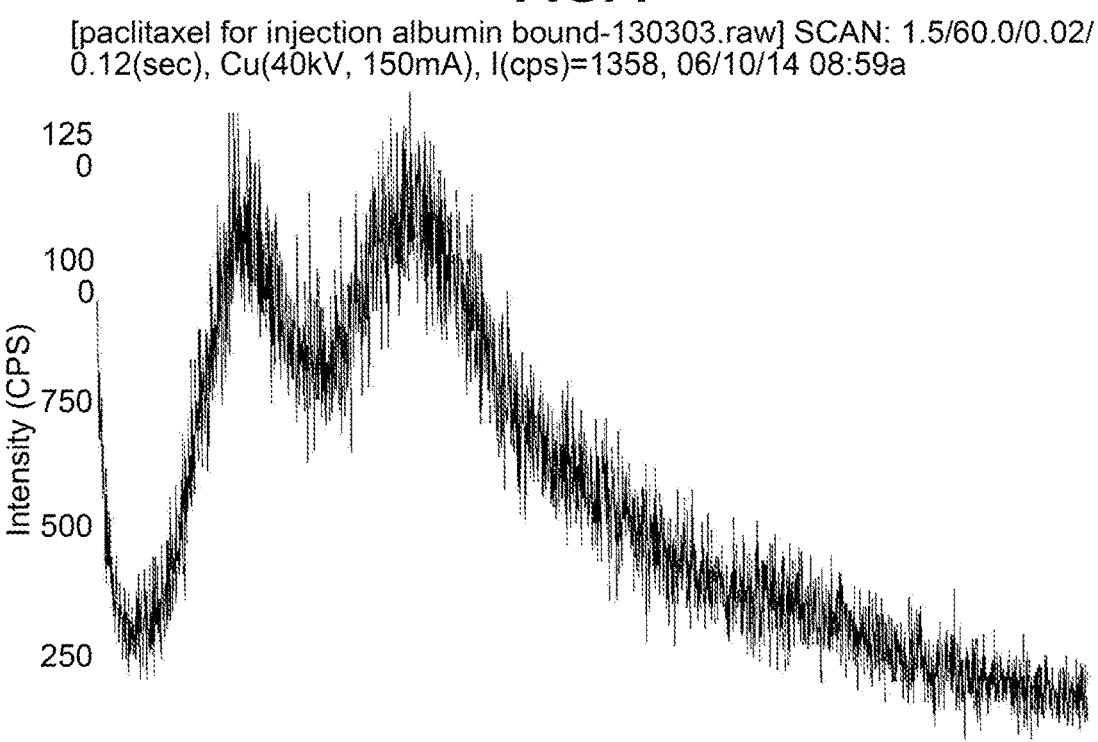
FIG. 8. X diffraction pattern of the paclitaxel-albumin nanoparticles corresponding to Example 8.

The crystal form was determined in an X-ray diffraction instrument for the drug substance of paclitaxel and lyophilized albumin powder, and the results are shown in FIG. 3 and FIG. 4. As shown, the drug substance of paclitaxel was crystalline powder, and the lyophilized albumin powder was amorphous powder. Representative purified nanoparticles obtained in Example 12 (corresponding to Example 2, 4, 6, and 8) were lyophilized in a lyophilizer to obtain solid powder, the crystal form of which was detected in an X-ray diffraction instrument, and the results are shown in FIGS. 5, 6, 7, and 8. It can be seen from the X diffraction pattern that the ratio of albumin to paclitaxel in the particles was in the range from 0.043:1 to 0.57:1, and both albumin and paclitaxel were in amorphous form, which was significantly different from the drug substance of paclitaxel, and slightly different from the lyophilized albumin powder.

Example 22. Release of Paclitaxel from the Particles

Using the separation method for particles established in Example 11, free component can be effectively separated from the component in nanoparticle form. As a consequence, the release of paclitaxel from particles can be detected at different concentrations using such a method, and specific procedure was shown below:

For the paclitaxel-albumin nanoparticles obtained in Example 12 (corresponding to Example 1-9, respectively), representative purified nanoparticles (corresponding to Example 2, 4, 6, and 8, and referred as Particle 2, 4, 6, and 8) were selected and 0.9% sodium chloride solution was added based on the ratio between albumin and paclitaxel, to form a stock solution with paclitaxel concentration of 5 mg/ml. The stock solution and simulated blood plasma solution were kept in 37° C. The stock solution was diluted using simulated blood plasma solution to obtain a series of paclitaxel solutions with concentrations of 5000, 1000, 200, 150, 100, 80, 50, 30, and 10 µg/ml.

Figure 9:
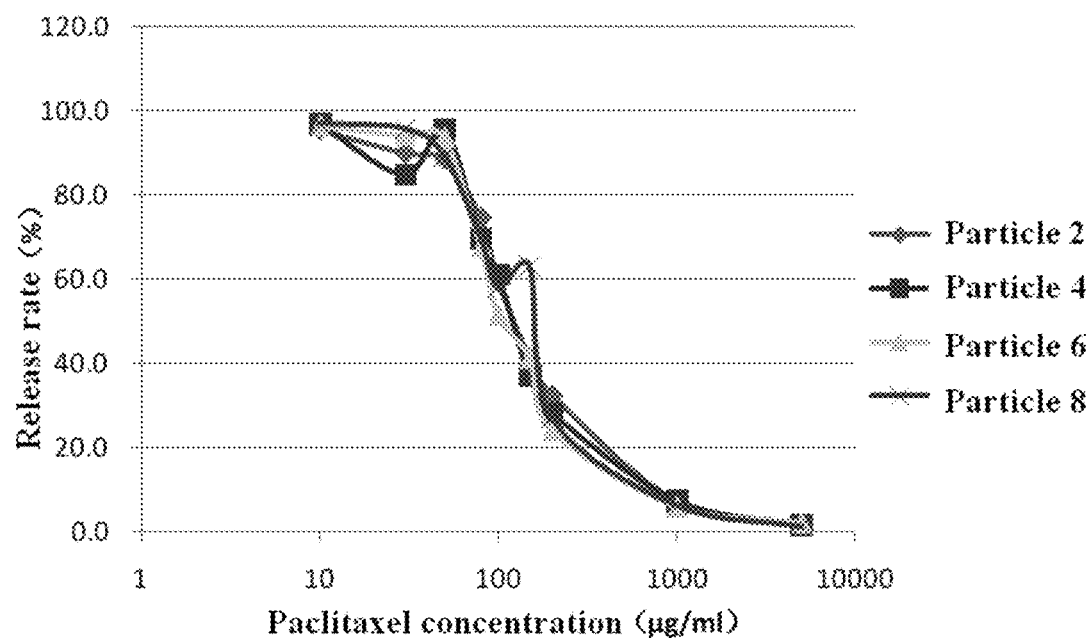
FIG. 9. In vitro release profiles of purified nanoparticles of various formulations.
Figure 10:
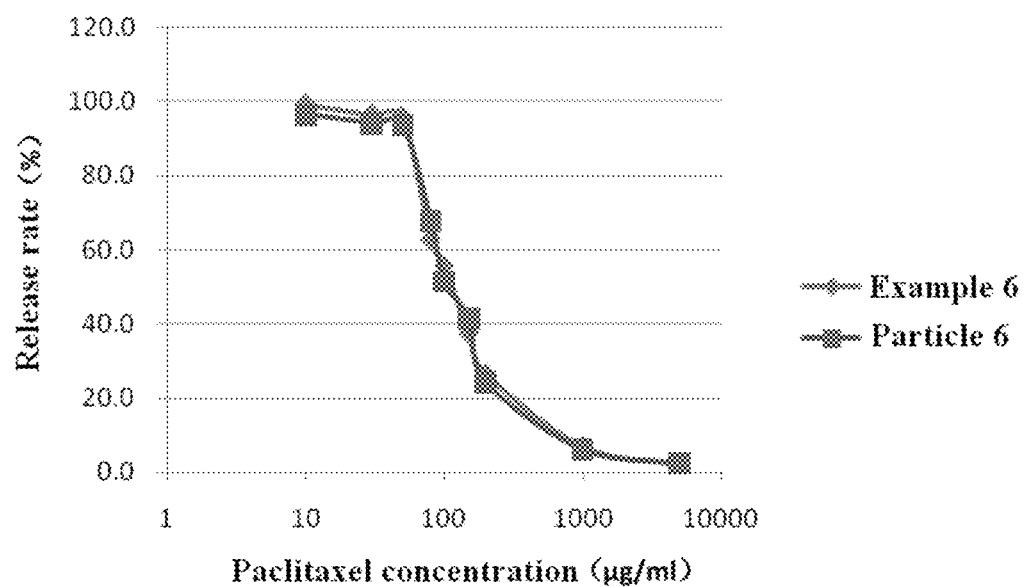
FIG. 10. In vitro release profiles of purified nanoparticles and traditional formulations.

Determination of release rate: the paclitaxel concentrations of the prepared sample solutions were determined, and at the same time, the paclitaxel concentrations of the supernatants were also determined after centrifugation at 21000×g for 60 min using 1 ml of each sample. The release ratio of paclitaxel at each concentration was calculated by dividing the paclitaxel concentration in the supernatant by the concentration before centrifugation, and the release curves were plotted and shown in FIG. 9 and FIG. 10. It can be seen from the release curve that the ratio of albumin to paclitaxel in the particles was in the range from 0.043:1 to 0.057:1, and the release behaviors of paclitaxel for the particles were substantially the same, all of which were correlated to the concentration.

Example 23. Preparation of Compositions Containing Therapeutic Nanoparticles Method 1 (Centrifugation-Re-suspension): therapeutic nanoparticles obtained in Example 12 corresponding to Example 1-9 (referred as Particle 1, 2, 3, 4, 5, 6, 7, 8, and 9) were re-suspended in 5% mannitol solution, 10% sucrose solution, 5% dextran solution, 10% lactose solution, 10% trehalose solution, 10% maltose solution, 10% human serum albumin solution, respectively, to establish paclitaxel concentrations of 5 mg/ml. The re-suspensions were filtered through a 0.22 μm sterile filter, and no significant variation of particle size was observed for the particles in the filtrate. The suspensions were lyophilized in a lyophilizer respectively to obtain the compositions containing the pharmaceutical nanoparticles.

Method 2 (Dialysis): the samples obtained in Example 1-9 were each reconstituted to prepare suspensions with the paclitaxel concentration of 5 mg/ml. Subsequently, the suspensions were dialyzed using a 300 kDa ultrafiltration membrane respectively by 5% mannitol solution, 10% sucrose solution, 5% dextran solution, 10% lactose solution, 10% maltose solution, 10% trehalose solution, and 10% human serum albumin solution. After dialyzing to 5-time of the initial volume, free human serum albumin in the suspensions was all replaced. The suspensions were filtered through a 0.22 μm sterile filter, and no significant variation of particle size was observed for the particles in the filtrate. The suspensions were lyophilized in a lyophilizer respectively to obtain the compositions containing the therapeutic nanoparticles.

Example 24

The compositions containing the therapeutic nanoparticles obtained in Method 1 (Centrifugation-Re-suspension) and Method 2 (Dialysis) in Example 23 were each reconstituted in water for injection to establish a paclitaxel concentration of 5 mg/ml. Stability for each solution was observed, and 12 h stability at room temperature was determined. As shown, conventional lyoprotectants can play a protective role for purified paclitaxel-albumin nanoparticles. The results are shown in Table 9 and Table 10:

TABLE 9

Stability of the compositions obtained by Centrifugation-Re-suspension

| | Particles contained in the composition | | | | | | | | |
|---|---|---|---|---|---|---|---|---|---|
| | Particle 1 | Particle 2 | Particle 3 | Particle 4 | Particle 5 | Particle 6 | Particle 7 | Particle 8 | Particle 9 |
| 5% mannitol solution | √ | √ | √ | √ | √ | √ | √ | √ | √ |
| 10% sucrose solution | √ | √ | √ | √ | √ | √ | √ | √ | √ |
| 5% dextran solution | √ | √ | √ | √ | √ | √ | √ | √ | √ |
| 10% lactose solution | √ | √ | √ | √ | √ | √ | √ | √ | √ |
| 10% trehalose solution | √ | √ | √ | √ | √ | √ | √ | √ | √ |
| 10% maltose solution | √ | √ | √ | √ | √ | √ | √ | √ | √ |
| 10% human serum albumin solution | √ | √ | √ | √ | √ | √ | √ | √ | √ |

Note:
√ stands for a clear solution, with no obvious precipitate, and no variation of particle size as compared to its initial result.

TABLE 10

Stability of the compositions obtained by Dialysis

| | Particles contained in the composition | | | | | | | | |
|---|---|---|---|---|---|---|---|---|---|
| | Particle 1 | Particle 2 | Particle 3 | Particle 4 | Particle 5 | Particle 6 | Particle 7 | Particle 8 | Particle 9 |
| 5% mannitol solution | √ | √ | √ | √ | √ | √ | √ | √ | √ |
| 10% sucrose solution | √ | √ | √ | √ | √ | √ | √ | √ | √ |
| 5% dextran solution | √ | √ | √ | √ | √ | √ | √ | √ | √ |
| 10% lactose solution | √ | √ | √ | √ | √ | √ | √ | √ | √ |
| 10% maltose solution | √ | √ | √ | √ | √ | √ | √ | √ | √ |
| 10% trehalose solution | √ | √ | √ | √ | √ | √ | √ | √ | √ |
| 10% human serum albumin solution | √ | √ | √ | √ | √ | √ | √ | √ | √ |

Note:
√ stands for a clear solution, with no obvious precipitate, and no variation of particle size as compared to its initial result.

As shown, the stability of particles can be maintained by replacing the albumin surrounding the particles using Centrifugation-Re-suspension (Method 1) and Dialysis (Method 2).

Example 25. Sensitization Study in Guinea Pig

In this experiment, the product from Example 6 and 5% mannitol formulation comprising Particle 6 from Example 24 were selected as the test drug, wherein the paclitaxel concentrations in the formulations are listed in the table below. The sensitization dosages were selected as 3 mg per guinea pig and 1.25 mg per guinea pig. Sensitization was conducted by intraperitoneal injection once every other day, for a total of 3 injections. At the same time, a positive control group (0.2% ovalbumin) and a negative control group (0.9% sodium chloride injection) were also established. Detailed dosage regimen is listed in the table below.

TABLE 11

Protocol for sensitization study in guinea pig

| Group | Number of the animal | Concentration of the drug (mg/ml) | Sensitization Administration volume (ml/guinea pig) | Sensitization Administration dosage (ml/guinea pig) | Excitation Administration volume (ml/guinea pig) | Excitation Administration dosage (ml/guinea pig) |
|---|---|---|---|---|---|---|
| Negative control group | 6 | — | 0.5 | — | 1 | — |
| Positive control group | 6 | 2 | 0.5 | 1 | 1 | 2 |
| Low dosage of product from Example 6 | 6 | 2.5 | 0.5 | 1.25 | 1 | 2.5 |
| High dosage of product from Example 6 | 6 | 6 | 0.5 | 3 | 1 | 6 |
| Low dosage of Particle 6 | 6 | 2.5 | 0.5 | 1.25 | 1 | 2.5 |
| High dosage of Particle 6 | 6 | 6 | 0.5 | 3 | 1 | 6 |

Administration method for sensitization: the back of guinea pig was firmly held by cup-shape left hand, allowing the abdominal skin stretched when the guinea pig was fixed. The abdomen of the guinea pig was lifted, and the head was lowered down. After disinfecting of the injection site by an alcohol wipe, the needle of a 2 ml disposable syringe held by the right hand was punctured into the skin of the guinea pig. The needle was inserted at the site 1 mm left to the midline of lower abdomen. When arriving at the subcutaneous part, the needle was inserted forward for further 5 mm to 10 mm, and subsequently punctured into the abdominal cavity at an angle of 45°. After fixing the needle, the pharmaceutical solution was injected slowly. After the injection, a dry cotton wipe was pressed on the pinprick in order to prevent the outflow of the pharmaceutical. After 3 times of sensitization, the guinea pigs in the group of the formulation from Example 6 (3 mg/guinea pig) became emaciated, and died. No abnormality was observed in other groups.

Allergy excitation: excitation was conducted by intravenous injection, and the excitation was performed 10 d after the last sensitization with the dosages of 6 mg/animal and 2.5 mg/animal.

Administration method for excitation: injection was performed to the lateral metatarsal vein of the guinea pig fixed by an assistant. The stifles were grasped by the operator to fix the body of the animal. Its vein was compressed, and the legs were in a stretched state. The hair at the injection site was shaved (or the skin at the injection site was cut). After sterilization by alcohol wipes, thick lateral metatarsal vein can be seen. The needle of a 1 ml disposable syringe was punctured into the blood vessel along the direction to the heart by the right hand. After the injection, a dry cotton wipe was pressed on the pinprick in order to prevent bleeding.

The reaction of each animal and the time when allergy symptoms appeared or disappeared were observed immediately after the excitation for 30 min. Maximal observation duration was 3 h. The results of allergic reaction are listed in Table 14.

TABLE 12

Symptoms of allergic reaction

| | |
|---|---|
| 0 | Normal |
| 1 | Dysphoria |
| 2 | Piloerection |
| 3 | Trembling |
| 4 | Nose scratching |
| 5 | Sneezing |
| 6 | Coughing |
| 7 | Tachypnea |
| 8 | Urination |
| 9 | Defecation |
| 10 | Lacrimation |
| 11 | Dyspnea |
| 12 | Wheezing |
| 13 | Peliosis |
| 14 | Gait disturbance |
| 15 | Jumping |
| 16 | Panting |
| 17 | Convulsion |
| 18 | Rotation |

TABLE 12-continued

Symptoms of allergic reaction

| | |
|---|---|
| 19 | Cheyne-stokes respiration |
| 20 | Death |

TABLE 13

Evaluation criteria for systemic allergic reaction

| Symptom | Degree | Result |
|---|---|---|
| 0 | − | Negative allergic reaction |
| 1-4 | + | Weakly positive allergic reaction |
| 5-10 | ++ | Positive allergic reaction |
| 11-19 | +++ | Strongly positive allergic reaction |
| 20 | ++++ | Extremely positive allergic reaction |

TABLE 14

Results for active anaphylaxis of guinea pig

| Group | Number of the animal | Reaction level | | | | | | Positive rate |
|---|---|---|---|---|---|---|---|---|
| | | 1 | 2 | 3 | 4 | 5 | 6 | |
| Negative control group | 6 | − | − | − | − | − | − | − |
| Positive control group | 6 | ++++ | ++++ | ++++ | ++++ | ++++ | ++++ | ++++ |
| Low dosage of product from Example 6 | 6 | + | +++ | +++ | ++++ | ++ | ++ | +++ |
| High dosage of product from Example 6 | 6 | / | / | / | / | / | / | NA* |
| Low dosage of Particle 6 | 6 | − | − | − | − | − | − | − |
| High dosage of Particle 6 | 6 | + | − | − | + | − | + | + |

*stands for the fact that the animal became emaciated and dead after sensitization.

It has been suggested by the results of active anaphylaxis in guinea pigs that the nanoparticle formulation containing excessive albumin has stronger sensitization, whereas the formulation containing purified nanoparticles can significantly decrease the allergic reaction.

Example 26. Pharmacokinetic Study in Dogs

Figure 11:
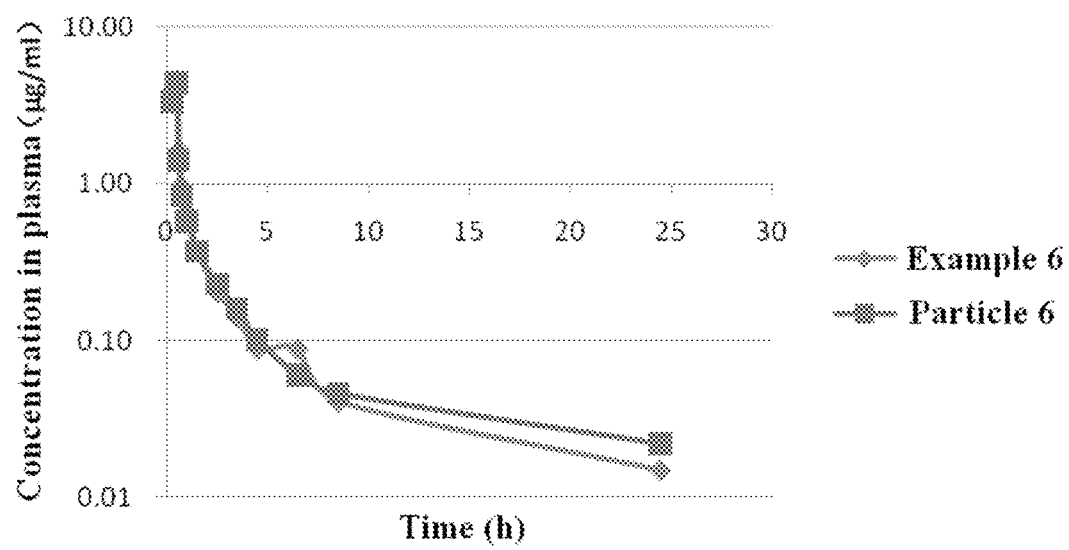
FIG. 11. Pharmacokinetic profiles of purified nanoparticles and traditional formulations in dogs.

In this experiment, the product from Example 6 and 5% mannitol formulation comprising Particle 6 from Example 24 were selected as the test drug, wherein the paclitaxel concentration in the formulations was 5 mg/ml. Beagle dog was employed for the in vivo pharmacokinetic studies of both formulations. In each group, 3 beagle dogs were tested with administration dosage of 5 mg/kg, and administration time length of 30 min. 2 ml blood was collected from the cephalic vein of the forelimb of beagle dogs immediately before administration (0 h), 15 min in the infusion process (0.25 h since administration), the time point of needle withdrawal (0.5 h since administration), and 0.58, 0.75, 1.0, 1.5, 2.5, 3.5, 4.5, 6.5, 8.5, 24.5 h post administration, and each blood samples were placed into a heparin tube, shaken until homogenous, and centrifuged at 3000 rpm for 10 min to obtain the plasma. The paclitaxel concentration in plasma was determined by HPLC/MS/MS, and the drug concentration was plotted versus time (See FIG. 11). It can be seen from the drug concentration-time plot that both formulations had almost the same in vivo behaviors, so that there was no impact by excessive albumin on the in vivo behaviors of the particles.

Example 27. Allergic Symptoms During the Pharmacokinetic Study in Dogs

In the pharmacokinetic study in dogs conducted in Example 26, adverse reactions were observed during the administration of both formulations. In the sample group of Example 6, various degrees of obvious allergic reactions appeared in 3 dogs, mainly including violently struggling, excessive salivation, erythema around mouth, and in individual experimental animals, vomiting and urinary incontinence occurred during administration. While for the sample group of Particle 6, only slightly struggling, salivation, and erythema around mouth appeared in part of the animals and the symptoms are mild. Consequently, the formulation of purified nanoparticles was capable of significantly alleviating the allergic reactions of the drug.

Example 28

The following samples were investigated for the maximum tolerated dose, the samples including the composition comprising the therapeutic nanoparticles using mannitol as the lyoprotectant (obtained from Method 1 of Example 24, corresponding to the nanoparticles of Example 2, 6, and 8, and referred as Particle 2, Particle 6, and Particle 8 below), product from Example 6, and Taxol® prepared with Cremophor.

Based on the recommendation of NCI of USA, modifications were made to the experimental method for determining the maximum tolerated dose of acute toxicity by single dose administration. For Particle 2, Particle 6 and Particle 8, and lyophilized powder from Example 6, 400 mg/kg was selected as the maximum administration dose, and the administration dose was reduced in a ratio of 1.2, i.e., a series of doses of 400, 333, 278, 231 and 193 mg/kg. For TAXOL®, 48 mg/kg was selected as the maximum administration dose, and the administration dose was also reduced in a ratio of 1.2, i.e., a series of doses of 48, 40, 33.3, 27.8, 23.1 and 19.3 mg/kg. In each dose group, 3 KM male mice were assigned. The general conditions and variations of body weight of the animals were observed for 10 days after administration. If no animal died, no irreversible toxic response occurred, or no more than 15% of body weight loss appeared for 3 continuous days as compared to that of before experiment during observation, the maximum administration dose was considered as the maximum tolerated dose for the single administration.

The results indicated that the maximum tolerated dose of TAXOL® was 33.3 mg/kg. In all administration groups, during administration of TAXOL®, the mice struggled violently, and coma and accelerated breathing occurred after administration. In the dose groups of 40 mg/kg and 48 mg/kg, cases of death occurred. In the rest dose groups, mice recovered gradually after administration. The severity of toxicity symptoms and the time demanded for recovery were correlated to the administration dose. The maximum tolerated doses for Example 6 and Particle 2, Particle 6 and Particle 8 were all 193 mg/kg. Adverse symptoms of the mice in the groups of doses above 193 mg/kg mainly included body weight loss, dirt around anus, rear limb weakness/paralysis, and death. The severity of adverse product from Example 6 on H22 tumor. The tumor inhibitory rate of Particle 2, Particle 8 and the product from Example 6 was significantly higher than TAXOL®.

TABLE 15

Effect on the body weight of mice bearing H22 tumor(n = 10, $\bar{x} \pm sd$)

| Group | Dosage (mg/kg) | Initial weight (g) | Final weight (g) | Growth of body weight (%) | Tumor weight (g) | Tumor inhibitory rate (%) |
|---|---|---|---|---|---|---|
| Particle 2 | 193 | 22.8 ± 1.6 | 29.3 ± 2.7**▲▲ | 28.9 | 0.7168 ± 0.5081**▲ | 70.9 |
| Particle 6 | 193 | 23.9 ± 1.5 | 29.6 ± 2.1**▲▲ | 24.0 | 0.9965 ± 0.6347** | 59.6 |
| Particle 8 | 193 | 23.8 ± 1.4 | 29.0 ± 4.3**▲▲ | 22.1 | 0.6090 ± 0.4129**▲▲ | 75.3 |
| The product from Example 6 | 193 | 23.7 ± 1.4 | 27.4 ± 2.3**▲▲ | 15.8 | 0.7213 ± 0.4604**▲ | 70.7 |
| Taxol ® | 33.3 | 23.2 ± 2.2 | 35.1 ± 2.8* | 51.4 | 1.2789 ± 0.5556* | 48.1 |
| Control | — | 22.0 ± 2.7 | 38.3 ± 2.8 | 74.1 | 2.4644 ± 1.1753 | |

**$p < 0.01$,
*$p < 0.05$, as compared to the blank control group;
▲▲$p < 0.01$,
▲$p < 0.05$, as compared to Taxol ® symptoms was enhanced with increased administration dose. There was no obvious difference among the toxicities to the mice by Particle 2, Particle 6, Particle 8 and the product from Example 6. However, all the above toxicities were lower than that of TAXOL® prepared with Cremophor.

Example 29. Inhibitory Effect on H22 Tumour of Liver Cancer in Mice

Particle 2, Particle 6, Particle 8, the product from Example 6, and Taxol® prepared with Cremophor were studied for liver cancer H22 tumor inhibitory effect in mice.

The animals were divided based on body weight. Ascitic cells of H22 liver cancer were subcutaneously inoculated to the subcutaneous tissue in the axillary region of the forelimbs of male KM mice with the inoculation volume of 0.2 ml, which contained about $1.0 \times 10^6$ cells. The animals were equally divided into 6 groups according to the inoculation time.

Single intravenous administrations of Particle 2, Particle 6, Particle 8, the product from Example 6 and Taxol® were performed at the maximum tolerated dose of mice 24 h after inoculation, i.e., the administration doses of Particle 2, Particle 6, Particle 8, and the product from Example 6 were 193 mg/kg, and the administration dose of Taxol® was 33.3 mg/kg. In the blank control group, 0.9% sodium chloride injection was used for the single-intravenous administration. On the 12$^{th}$ day after administration, the mice were sacrificed by $CO_2$ asphyxia, and the tumor mass was taken out and weighed. The tumor inhibitory rate (%) can be calculated according to the following equation: Tumor inhibitory rate=(1−average tumor weight in the test groups/average tumor weight in the control group)×100%. The experimental results were statistically analyzed by One-way ANOVA using statistical software of SPSS 19.0.

The experimental results are listed in Table 15. For single intravenous administration at the maximum tolerated dose of mice, the growth of H22 tumor was significantly inhibited in all groups. There was no inter-group difference in the tumor inhibitory effect of Particle 2, Particle 6, Particle 8 and the Example 30. Inhibitory Effect on the Prostatic Cancer RM-1 Tumour of Mice Particle 2, Particle 6, Particle 8, the product from Example 6, and TAXOL® prepared with Cremophor were studied for prostatic cancer RM-1 tumor inhibitory effect in mice.

The RM-1 tumor cells at logarithmic growth phase were collected, and the cell number was adjusted to $2.5 \times 10^6$ cells/ml. The suspension of tumor cells was inoculated to the subcutaneous tissue in the axillary region of the forelimbs of 7 to 8-week-old C75 male mice with the inoculation volume of 0.2 ml, which contained about $5 \times 10^5$ cells. After inoculation, the remained suspension of tumor cells was counted under an optical microscope, with the number of live tumor cells >95%. The mice were divided into 6 groups based on inoculation time.

Single intravenous administrations of Particle 2, Particle 6, Particle 8, the product from Example 6 and Taxol® were performed at the maximum tolerated dose of mice 72 h after inoculation, i.e., the administration doses of Particle 2, Particle 6, Particle 8, and the product from Example 6 were 193 mg/kg, and the administration dose of Taxol® was 33.3 mg/kg. In the blank control group, 0.9% sodium chloride injection was used for the single-intravenous administration. After the outgrowth of tumor, the diameter was measured using a vernier caliper, and the anti-tumor effect of the pharmaceutical was observed dynamically. The tumor volume (TV) can be calculated as follows: $V=\frac{1}{2} \times a \times b^2$, wherein a and b refer to the length and width of tumor, respectively. The tumor volume can be calculated based on the results. The tumor volume inhibitory rate (%) can be calculated according to the following equation: Tumor inhibitory rate= (1−average tumor volume in the administration groups/ average tumor volume in the control group)×100%. The experimental results were analyzed by statistical software SPSS 19.0. The inter-measure tumor volume variation with time was analyzed by Repeated Measure Analysis, and the inter-group tumor volume variation among each measure was analyzed by Multivariate.

The experimental results are listed in Table 16. Single intravenous administrations were performed at the maximum tolerated dose 3 days after inoculation of prostatic cancer RM-1 tumor cells. As compared to the blank control group, significant inhibitory effect on the growth of the prostatic cancer RM-1 tumor of mice was observed for Particle 2, Particle 6, Particle 8 and the product from Example 6, and no inhibitory effect on the tumor was seen for Taxol® prepared with Cremophor. No significant difference in the inhibitory effect of Particle 2, Particle 6, Particle 8 and the product from Example 6 was observed on RM-1 tumor of mice. However, as compared to Taxol®, all the above formulations had significant inhibitory effect on the growth of tumor.

cells/ml. The suspension of tumor cells was inoculated to the subcutaneous tissue in the axillary region of the forelimbs of 7 to 8-week-old C57 male mice with the inoculation volume of 0.2 ml, which contained about $5 \times 10^5$ cells.

The grouping, administration, indicator observation and statistical method were the same as those in Example 18.

The experimental results are listed in Table 17. Single intravenous administrations were performed at the maximum tolerated dose 3 days after inoculation of tumor cells of Lewis lung cancer mice. As compared to the blank control group, significant inhibitory effect on the growth of the tumor of the Lewis lung cancer mice was observed for

TABLE 16

Inhibitory effect on prostatic cancer RM-1 tumor of mice(n = 10, x̄ ± sd)

|  | Dosage (mg/kg) | Initial weight (g) | Final weight (g) | Growth of body weight | 7 d after inoculation | 10 d after inoculation | 12 d after inoculation | 14 d after inoculation |
|---|---|---|---|---|---|---|---|---|
|  |  |  |  |  | Tumor volume (mm³)/Tumor inhibitory rate % | | | |
| Particle 2 | 193 | 27.6 ± 1.8 | 32.3 ± 2.3 | 17.0% | 107.9 ± 25.8**▲ 59.7% | 210.6 ± 128.6*▲ 49.9% | 471.6 ± 305.0 28.9% | 715.5 ± 367.1▲ 40.7% |
| Particle 6 | 193 | 29.4 ± 2.0 | 34.2 ± 3.9* | −6.3% | 96.2 ± 23.3**▲▲ 64.1% | 122.6 ± 45.9**▲▲ 70.8% | 331.7 ± 142.2*▲ 50.0% | 600.3 ± 302.2*▲▲ 50.2% |
| Particle 8 | 193 | 28.2 ± 2.1 | 326 ± 3.2 | 15.8% | 107.1 ± 28.7**▲ 60.0% | 148.7 ± 56.6**▲▲ 64.6% | 385.1 ± 138.4* 41.9% | 736.4 ± 472.9 38.9% |
| The product from Example 6 | 193 | 28.1 ± 2.0 | 33.7 ± 2.6**▲ | −9.9% | 110.6 ± 18.2**▲ 58.7% | 187.1 ± 60.0**▲ 55.5% | 395.9 ± 147.8* 40.3% | 590.0 ± 171.2*▲▲ 51.1% |
| Taxol ® | 33.3 | 26.8 ± 1.9 | 31.1 ± 2.7 | 16.2% | 198.6 ± 103.9 25.8% | 430.3 ± 272.7 −2.5% | 563.7 ± 311.3 15.0% | 1113.2 ± 460.0 7.7% |
| Control |  | 26.6 ± 1.5 | 30.5 ± 2.3 | 14.6% | 267.6 ± 169.1 | 420.0 ± 217.7 | 663.2 ± 338.4 | 1205.7 ± 735.1 |

**$p < 0.01$,
*$p < 0.05$, as compared to the blank control group;
▲▲$p < 0.01$,
▲$p < 0.05$, as compared to Taxol ®

Example 31. Inhibitory Effect on the Tumor of the Lewis Lung Cancer Mice

Particle 2, Particle 6, Particle 8, the product from Example 6, and TAXOL® prepared with Cremophor were studied for the inhibitory effect on tumor in Lewis lung cancer mice.

The Lewis tumor cells at logarithmic growth phase were collected, and the cell number was adjusted to $2.5 \times 10^6$ Particle 2, Particle 6, Particle 8 and the product from Example 6, and no inhibitory effect on the tumor was seen for Taxol® prepared with Cremophor. No significant difference in the inhibitory effect of Particle 2, Particle 6, Particle 8 and the product from Example 6 was observed on the tumor of the Lewis lung cancer mice. However, as compared to Taxol®, all the above formulations had significant inhibitory effect on the growth of tumor.

TABLE 17

Inhibitory effect on the tumor of the Lewis lung cancer mice(n = 10, x̄ ± sd)

| Group | Dosage mg/kg | Initial weight g / Final weight g | Growth of body weight | 7 d after inoculation | 10 d after inoculation | 12 d after inoculation | 14 d after inoculation | 17 d after inoculation | 19 d after inoculation | 21 d after inoculation |
|---|---|---|---|---|---|---|---|---|---|---|
|  |  |  |  | Tumor volume (mm³)/Tumor inhibitory rate % | | | | | | |
| Particle 2 | 193 | 25.7 ± 1.7 / 29.9 ± 2.3 | 16.4% | 45.5 ± 33.4**▲▲ 67.7% | 172.4 ± 37.4**▲ 32.9% | 166.0 ± 39.9**▲▲ 48.1% | 239.2 ± 88.8**▲▲ 52.6% | 566.6 ± 273.9*▲ 48.5% | 856.9 ± 436.5* 45.9% | 1608.1 ± 714.4 34.7% |
| Particle 6 | 193 | 26.4 ± 1.2 / 30.1 ± 1.8▲ | 13.7% | 11.7 ± 25.1**▲▲ 91.7% | 153.8 ± 70.1**▲ 40.1% | 177.7 ± 119.0*▲▲ 44.5% | 282.8 ± 278.3▲ 44.0% | 640.1 ± 701.1 41.9% | 940.0 ± 788.6 40.6% | 1536.4 ± 1288.9 37.6% |

TABLE 17-continued

Inhibitory effect on the tumor of the Lewis lung cancer mice(n = 10, $\bar{x} \pm sd$)

| Group | Dosage mg/kg | Initial weight g Final weight g | Growth of body weight | Tumor volume (mm³)/Tumor inhibitory rate % | | | | | | |
|---|---|---|---|---|---|---|---|---|---|---|
| | | | | 7 d after inoculation | 10 d after inoculation | 12 d after inoculation | 14 d after inoculation | 17 d after inoculation | 19 d after inoculation | 21 d after inoculation |
| Particle 8 | 193 | 26.7 ± 1.5 31.1 ± 2.0▲▲ | 16.6% | 0.0 ± 0.0**▲▲ 100.0% | 161.1 ± 41.0**▲ 37.3% | 157.4 ± 61.7**▲▲ 50.8% | 256.7 ± 146.3*▲▲ 49.2% | 461.6 ± 244.3**▲ 58.1% | 850.7 ± 1475.8* 46.3% | 1278.3 ± 507.3*▲▲ 48.1% |
| The product from Example 6 | 193 | 26.1 ± 1.5 31.6 ± 2.0▲▲ | 21.2% | 98.9 ± 41.2*▲ 29.7% | 196.5 ± 46.8 23.5% | 210.7 ± 72.8▲▲ 34.1% | 360.9 ± 271.4 28.6% | 671.7 ± 521.0 39% | 1030.0 ± 863.5 34.9% | 1539.8 ± 1342.5 37.5% |
| Taxol ® | 33.3 | 25.6 ± 1.8 28.0 ± 2.2 | 9.6% | 137.1 ± 35.3 2.5% | 254.2 ± 108.6 1.0% | 373.8 ± 139.5 −16.9% | 616.0 ± 303.1 −21.9% | 1111.5 ± 698.4 −0.9% | 1373.7 ± 839.7 13.2% | 2486.8 ± 1148.3 −1.0% |
| Control | | 26.2 ± 2.2 30.0 ± 3.2 | 14.3% | 140.6 ± 39.1 | 256.8 ± 83.1 | 319.9 ± 149.3 | 505.2 ± 251.2 | 1101.2 ± 555.6 | 1582.7 ± 833.5 | 2462.8 ± 1275.3 |

**$p < 0.01$,
*$p < 0.05$, as compared to the blank control group:
▲▲$p < 0.01$,
▲$p < 0.05$, as compared to Taxol ®

Example 32

As a commercially available pharmaceutical product, human serum albumin should contain no more than 5% of the polymer according to its quality standard, since the albumin polymer may induce allergic reaction. The determination method for albumin in Example 10 can distinguish albumin monomer from the polymer. The albumin polymer and paclitaxel content were detected in the compositions from Example 1-9 (referred as initial formulation) and the compositions obtained from Method 1 of Example 24, respectively using mannitol and human serum albumin as a lyoprotectant (corresponding to Example 1-9), based on the determination method for albumin and paclitaxel in Example 10, and the albumin polymer content was calculated per 1 mg paclitaxel. The results are listed in Table 18.

TABLE 18

Relative amount of albumin polymer and paclitaxel in various formulations

| | Initial formulation (mg/mg) | Mannitol as lyoprotectant (mg/mg) | Albumin as lyoprotectant (mg/mg) |
|---|---|---|---|
| Example 1 | 1.7 | 0.03 | 0.18 |
| Example 2 | 12.5 | 0.11 | 0.20 |
| Example 3 | 6.3 | 0.05 | 0.19 |
| Example 4 | 3.2 | 0.04 | 0.17 |
| Example 5 | 2.1 | 0.03 | 0.18 |
| Example 6 | 1.6 | 0.03 | 0.18 |
| Example 7 | 0.8 | ND | 0.17 |
| Example 8 | 0.9 | ND | 0.16 |
| Example 9 | 2.0 | 0.03 | 0.17 |

Note:
ND stands for lower than the limit of determination, i.e., not detected

It has been suggested by the results that the content of albumin polymer in the product prepared directly using the method of prior art (Homogenization) was significantly higher than the content in the post-added albumin of the composition by the preparation method of the present disclosure. This was resulted from albumin polymer newly generated in the homogenization process or evaporation process of the prior art. However, the content of albumin polymer in the formulation comprising mannitol protectant was lower, since only very small amount of albumin was comprised in the formulation, so that the total amount was lower than the amount of the polymer in initial formulation.

Example 33. Recovering Albumin for Preparation of the Nanoparticles

The dialysate resulted from the dialysis in Example 15 was collected, and concentrated to an albumin content of about 4% using a regenerated cellulose ultrafiltration membrane with a cut-off molecular weight of 10K. The concentrate was dialyzed in equal volume by purified water. After dialyzed to a 5-time volume, 4% albumin solution can be recovered.

According to the method in Example 5, paclitaxel-albumin nanoparticles were prepared using recovered albumin solution. Consequently, the average diameter of the prepared paclitaxel-albumin nanoparticles was 134 nm, and the suspension was translucent, which was similar to the product obtained in Example 5.

The suspension can be smoothly filtered through a 0.22 μm sterile filter. There was no significant variation of the particle size after filtration, and no significant change was observed for the suspension after storage for 48 h at room temperature. The suspension was aliquoted and lyophilized for 24 h in a lyophilizer to obtain a stable off-white cake.

Example 34. Preparation of Purified Docetaxel-Albumin Particles 3 g docetaxel was dissolved into 15 ml chloroform/ethanol (1:1, v/v), and added into 500 ml human serum albumin solution (4% w/v). The mixture was emulsified for 2 min using a high shear disperser (Fluko FZ-20) to obtain a primary emulsion. The primary emulsion was then homogenized using a high pressure homogenizer under a pressure of 10000-20000 psi to obtain a nano-emulsion. Subsequently, the nano-emulsion was transferred to a rotatory evaporator to remove the organic solvent in the solution by vacuum evaporation at 40 mbar and at 40° C. in a water-bath. The docetaxel-albumin nanoparticles were thus generated with an average diameter of 110-150 nm, and the suspension was translucent.

The nanoparticles were isolated from the resultant docetaxel-albumin nanoparticle suspension by centrifugation method referred in Example 11 at 21000×g for 60 min. The supernatant was discarded, and the purified nanoparticles were collected. Purified nanoparticles were re-suspended in 5% mannitol solution. The re-suspension was filtered through a 0.22 μm sterile filter, and there was no significant variation of the particle size in the filtrate. The content of docetaxel in the solution was determined using HPLC. Based on the content, the solution was subsequently aliquoted into vials at an amount of 50 mg per vial. The vials were placed in a lyophilizer and lyophilized for 48 h.

When the lyophilized product was reconstituted in water for injection, the resultant cake was dissolved rapidly, the suspension was translucent, and no significant variation of the particle size was observed. After determination of the human serum albumin and docetaxel content in the product, the ratio between albumin and docetaxel can be calculated as 0.1:1.

Example 35. Preparation of Purified 2'-O-Hexanoyldocetaxel Albumin Particles 695 mg 2'-O-hexanoyldocetaxel was dissolved into 6 ml chloroform/ethanol (10:1, v/v), and added into 102 ml human serum albumin solution (10% w/v). The mixture was emulsified for 2 min using a high shear disperser (Fluko FZ-20) to obtain a primary emulsion. The primary emulsion was then homogenized using a high pressure homogenizer under a pressure of 10000-20000 psi to obtain a nano-emulsion. Subsequently, the nano-emulsion was transferred to a rotatory evaporator to remove the organic solvent in the solution by vacuum evaporation at 40 mbar and at 40° C. in a water-bath. The 2'-O-hexanoyldocetaxel albumin nanoparticles were thus generated with an average diameter of 75-100 nm, and the suspension was translucent.

The nanoparticles were isolated from the resultant 2'-O-hexanoyldocetaxel albumin nanoparticle suspension by dialysis method against 5% mannitol solution referred in Example 15. The obtained purified nanoparticles suspension was filtered through a 0.22 μm sterile filter, and there was no significant variation of the particle size in the filtrate. The content of 2'-O-hexanoyldocetaxel in the solution was determined using HPLC. Based on the content, the solution was subsequently aliquoted into vials at an amount of 50 mg per vial. The vials were placed in a lyophilizer and lyophilized for 48 h.

When the lyophilized product was reconstituted in water for injection, the resultant cake was dissolved rapidly, the suspension was translucent, and no significant variation of the particle size was observed. After determination of the human serum albumin and 2'-O-hexanoyldocetaxel content in the product, the ratio between albumin and 2'-O-hexanoyldocetaxel can be calculated as 0.27:1.

Example 36. Preparation of Purified 2'-Benzoyl Docetaxel Albumin Particles 226 mg 2'-benzoyl docetaxel was dissolved into 2 ml chloroform/ethanol (9:1, v/v), and added into 35 ml human serum albumin solution (5% w/v). The mixture was emulsified for 2 min using a high shear disperser (Fluko FZ-20) to obtain a primary emulsion. The primary emulsion was then homogenized using a high pressure homogenizer under a pressure of 18000-20000 psi to obtain a nano-emulsion. Subsequently, the nano-emulsion was transferred to a rotatory evaporator to remove the organic solvent in the solution by vacuum evaporation at 40 mbar and at 40° C. in a water-bath. The 2'-benzoyl docetaxel albumin nanoparticles were thus generated with an average diameter of 30-60 nm, and the suspension was translucent.

The nanoparticles were isolated from the resultant 2'-benzoyl docetaxel albumin nanoparticle suspension by chromatographic column separation method referred in Example 16. 10% lactose solution was used as dialysate. The obtained purified nanoparticles suspension was filtered through a 0.22 μm sterile filter, and there was no significant variation of the particle size in the filtrate. The content of 2'-benzoyl docetaxel in the solution was determined using HPLC. Based on the content, the solution was subsequently aliquoted into vials at an amount of 50 mg per vial. The vials were placed in a lyophilizer and lyophilized for 65 h.

When the lyophilized product was reconstituted in water for injection, the resultant cake was dissolved rapidly, the suspension was translucent, and no significant variation of the particle size was observed. After determination of the human serum albumin and 2'-benzoyl docetaxel content in the product, the ratio between albumin and 2'-benzoyl docetaxel can be calculated as 0.95:1.

Example 37. Preparation of Purified Rapamycin Albumin Particles 166 mg rapamycin was dissolved into 1 ml chloroform/ethanol (11:1, v/v), and added into 37 ml human serum albumin solution (5% w/v). The mixture was emulsified for 2 min using a high shear disperser (Fluko FZ-20) to obtain a primary emulsion. The primary emulsion was then homogenized using a high pressure homogenizer under a pressure of 10000-20000 psi to obtain a nano-emulsion. Subsequently, the nano-emulsion was transferred to a rotatory evaporator to remove the organic solvent in the solution by vacuum evaporation at 40 mbar and at 40° C. in a water-bath. The rapamycin nanoparticles were thus generated with an average diameter of 50-85 nm, and the suspension was translucent.

The nanoparticles were isolated from the resultant rapamycin albumin nanoparticle suspension by chromatographic column separation method referred in Example 16. 5% dextrane solution was used as dialysate. The obtained purified nanoparticles suspension was filtered through a 0.22 μm sterile filter, and there was no significant variation of the particle size in the filtrate. The content of rapamycin in the solution was determined using HPLC. Based on the content, the solution was subsequently aliquoted into vials at an amount of 10 mg per vial. The vials were placed in a lyophilizer and lyophilized for 48 h.

When the lyophilized product was reconstituted in water for injection, the resultant cake was dissolved rapidly, the suspension was translucent, and no significant variation of the particle size was observed. After determination of the human serum albumin and rapamycin content in the product, the ratio between albumin and rapamycin can be calculated as 0.63:1.

Example 38. Preparation of Purified Temsirolimus Albumin Particles 101 mg temsirolimus was dissolved into 0.5 ml chloroform/ethanol (7:1, v/v), and added into 19.5 ml human serum albumin solution (5% w/v). The mixture was emulsified for 2 min using a high shear disperser (Fluko FZ-20) to obtain a primary emulsion. The primary emulsion was then homogenized using a high pressure homogenizer under a pressure of 10000-20000 psi to obtain a nano-emulsion. Subsequently, the nano-emulsion was transferred to a rotatory evaporator to remove the organic solvent in the solution by vacuum evaporation at 40 mbar and at 40° C. in a water-bath. The temsirolimus nanoparticles were thus generated with an average diameter of 80-115 nm, and the suspension was translucent.

The nanoparticles were isolated from the resultant temsirolimus albumin nanoparticles by centrifugation method referred in Example 11 at 21000×g for 60 min. The supernatant was discarded, and the purified nanoparticles were collected. Purified nanoparticles were re-suspended in 5% mannitol solution. The re-suspension was filtered through a 0.22 μm sterile filter, and there was no significant variation of the particle size in the filtrate. The content of temsirolimus in the solution was determined using HPLC. Based on the content, the solution was subsequently aliquoted into vials at an amount of 10 mg per vial. The vials were placed in a lyophilizer and lyophilized for 48 h.

When the lyophilized product was reconstituted in water for injection, the resultant cake was dissolved rapidly, the suspension was translucent, and no significant variation of the particle size was observed. After determination of the human serum albumin and temsirolimus content in the product, the ratio between albumin and temsirolimus can be calculated as 0.16:1.

Example 39. Preparation of Purified Everolimus Albumin Particles 78 mg everolimus was dissolved into 1 ml chloroform/ethanol (9:1, v/v), and added into 22 ml human serum albumin solution (8% w/v). The mixture was emulsified for 2 min using a high shear disperser (Fluko FZ-20) to obtain a primary emulsion. The primary emulsion was then homogenized using a high pressure homogenizer under a pressure of 10000-20000 psi to obtain a nano-emulsion. Subsequently, the nano-emulsion was transferred to a rotatory evaporator to remove the organic solvent in the solution by vacuum evaporation at 40 mbar and at 40° C. in a water-bath. The everolimus nanoparticles were thus generated with an average diameter of 80-110 nm, and the suspension was translucent.

The nanoparticles were isolated from the resultant everolimus albumin nanoparticle suspension by dialysis method referred in Example 15 against 5% dextrane. The obtained purified nanoparticles suspension was filtered through a 0.22 μm sterile filter, and there was no significant variation of the particle size in the filtrate. The content of everolimus in the solution was determined using HPLC. Based on the content, the solution was subsequently aliquoted into vials at an amount of 10 mg per vial. The vials were placed in a lyophilizer and lyophilized for 60 h.

When the lyophilized product was reconstituted in water for injection, the resultant cake was dissolved rapidly, the suspension was translucent, and no significant variation of the particle size was observed. After determination of the human serum albumin and everolimus content in the product, the ratio between albumin and everolimus can be calculated as 0.32:1.

Example 40. Preparation of Purified Romidepsin Albumin Particles 113 mg romidepsin was dissolved into 2 ml chloroform/ethanol (8:1, v/v), and added into 35 ml human serum albumin solution (10% w/v). The mixture was emulsified for 2 min using a high shear disperser (Fluko FZ-20) to obtain a primary emulsion. The primary emulsion was then homogenized using a high pressure homogenizer under a pressure of 10000-20000 psi to obtain a nano-emulsion. Subsequently, the nano-emulsion was transferred to a rotatory evaporator to remove the organic solvent in the solution by vacuum evaporation at 40 mbar and at 40° C. in a water-bath. The 2 romidepsin nanoparticles were thus generated with an average diameter of 120-150 nm, and the suspension was translucent.

The nanoparticles were isolated from the resultant romidepsin albumin nanoparticle suspension by chromatographic column separation method referred in Example 16. 10% sucrose solution was used as dialysate. The obtained purified nanoparticles suspension was filtered through a 0.22 μm sterile filter, and there was no significant variation of the particle size in the filtrate. The content of romidepsin in the solution was determined using HPLC. Based on the content, the solution was subsequently aliquoted into vials at an amount of 50 mg per vial. The vials were placed in a lyophilizer and lyophilized for 48 h.

When the lyophilized product was reconstituted in water for injection, the resultant cake was dissolved rapidly, the suspension was translucent, and no significant variation of the particle size was observed. After determination of the human serum albumin and romidepsin content in the product, the ratio between albumin and romidepsin can be calculated as 0.25:1.

Example 41. Preparation of Purified Pirarubicin Albumin Particles 147 mg pirarubicin was dissolved into 0.75 ml chloroform/ethanol (5:1, v/v), and added into 19.5 ml human serum albumin solution (5% w/v). The mixture was emulsified for 2 min using a high shear disperser (Fluko FZ-20) to obtain a primary emulsion. The primary emulsion was then homogenized using a high pressure homogenizer under a pressure of 10000-20000 psi to obtain a nano-emulsion. Subsequently, the nano-emulsion was transferred to a rotatory evaporator to remove the organic solvent in the solution by vacuum evaporation at 40 mbar and at 40° C. in a water-bath. The 2 pirarubicin nanoparticles were thus generated with an average diameter of 100-120 nm, and the suspension was translucent.

The nanoparticles were isolated from the resultant pirarubicin albumin nanoparticle suspension by dialysis method against 5% mannitol solution referred in Example 15. The obtained purified nanoparticles were filtered through a 0.22 μm sterile filter, and there was no significant variation of the particle size in the filtrate. The content of pirarubicin in the solution was determined using HPLC. Based on the content, the solution was subsequently aliquoted into vials at an amount of 10 mg per vial. The vials were placed in a lyophilizer and lyophilized for 48 h.

When the lyophilized product was reconstituted in water for injection, the resultant cake was dissolved rapidly, the suspension was translucent, and no significant variation of the particle size was observed. After determination of the human serum albumin and pirarubicin content in the product, the ratio between albumin and pirarubicin can be calculated as 0.47:1.

Example 42. Preparation of Purified Aclacinomycin Albumin Particles 135 mg aclacinomycin was dissolved into 2 ml chloroform/ethanol (8:1, v/v), and added into 25 ml human serum albumin solution (8% w/v). The mixture was emulsified for 2 min using a high shear disperser (Fluko FZ-20) to obtain a primary emulsion. The primary emulsion was then homogenized using a high pressure homogenizer under a pressure of 10000-20000 psi to obtain a nano-emulsion. Subsequently, the nano-emulsion was transferred to a rotatory evaporator to remove the organic solvent in the solution by vacuum evaporation at 40 mbar and at 40° C. in a water-bath. The aclacinomycin nanoparticles were thus generated with an average diameter of 80-150 nm, and the suspension was translucent.

The nanoparticles were isolated from the resultant aclacinomycin albumin nanoparticle suspension by chromatographic column separation method referred in Example 16. 5% mannitol solution was used as dialysate. The re-suspension was filtered through a 0.22 μm sterile filter, and there was no significant variation of the particle size in the filtrate. The content of aclacinomycin in the solution was determined using HPLC. Based on the content, the solution was subsequently aliquoted into vials at an amount of 10 mg per vial. The vials were placed in a lyophilizer and lyophilized for 48 h.

When the lyophilized product was reconstituted in water for injection, the resultant cake was dissolved rapidly, the suspension was translucent, and no significant variation of the particle size was observed. After determination of the human serum albumin and aclacinomycin content in the product, the ratio between albumin and aclacinomycin can be calculated as 0.13:1.

Example 43. Preparation of Purified Cabazitaxel Albumin Particles 289 mg cabazitaxel was dissolved into 3 ml chloroform/ethanol (10:1, v/v), and added into 67 ml human serum albumin solution (5% w/v). The mixture was emulsified for 2 min using a high shear disperser (Fluko FZ-20) to obtain a primary emulsion. The primary emulsion was then homogenized using a high pressure homogenizer under a pressure of 10000-20000 psi to obtain a nano-emulsion. Subsequently, the nano-emulsion was transferred to a rotatory evaporator to remove the organic solvent in the solution by vacuum evaporation at 40 mbar and at 40° C. in a water-bath. The cabazitaxel nanoparticles were thus generated with an average diameter of 65-85 nm, and the suspension was translucent.

The nanoparticles were isolated from the resultant cabazitaxel albumin nanoparticle suspension by equal volume dialysis referred in Example 15 against 5% mannitol. The purified nanoparticles suspension obtained were filtered through a 0.22 μm sterile filter, and there was no significant variation of the particle size in the filtrate. The content of cabazitaxel in the solution was determined using HPLC. Based on the content, the solution was subsequently aliquoted into vials at an amount of 50 mg per vial. The vials were placed in a lyophilizer and lyophilized for 55 h.

When the lyophilized product was reconstituted in water for injection, the resultant cake was dissolved rapidly, the suspension was translucent, and no significant variation of the particle size was observed. After determination of the human serum albumin and cabazitaxel content in the product, the ratio between albumin and cabazitaxel can be calculated as 0.27:1.

Example 44. Preparation of Purified Amiodardone Albumin Particles 90 mg amiodardone was dissolved into 2 ml chloroform/ethanol (11:1, v/v), and added into 58 ml human serum albumin solution (8% w/v). The mixture was emulsified for 2 min using a high shear disperser (Fluko FZ-20) to obtain a primary emulsion. The primary emulsion was then homogenized using a high pressure homogenizer under a pressure of 10000-20000 psi to obtain a nano-emulsion. Subsequently, the nano-emulsion was transferred to a rotatory evaporator to remove the organic solvent in the solution by vacuum evaporation at 40 mbar and at 40° C. in a water-bath. The 2 amiodardone nanoparticles were thus generated with an average diameter of 70-105 nm, and the suspension was translucent.

The nanoparticles were isolated from the resultant amiodardone albumin nanoparticle suspension by centrifugation method referred in Example 11 at 21000×g for 60 min. The supernatant was discarded, and the purified nanoparticles were collected. Purified nanoparticles were re-suspended in 5% dextran solution. The re-suspension was filtered through a 0.22 μm sterile filter, and there was no significant variation of the particle size in the filtrate. The content of amiodardone in the solution was determined using HPLC. Based on the content, the solution was subsequently aliquoted into vials at an amount of 10 mg per vial. The vials were placed in a lyophilizer and lyophilized for 57 h.

When the lyophilized product was reconstituted in water for injection, the resultant cake was dissolved rapidly, the suspension was translucent, and no significant variation of the particle size was observed. After determination of the human serum albumin and amiodardone content in the product, the ratio between albumin and amiodardone can be calculated as 0.43:1.

Example 45. Preparation of Purified Liothyronine Albumin Particles 93 mg liothyronine was dissolved into 2 ml chloroform/ethanol (9:1, v/v), and added into 46 ml human serum albumin solution (8% w/v). The mixture was emulsified for 2 min using a high shear disperser (Fluko FZ-20) to obtain a primary emulsion. The primary emulsion was then homogenized using a high pressure homogenizer under a pressure of 10000-20000 psi to obtain a nano-emulsion. Subsequently, the nano-emulsion was transferred to a rotatory evaporator to remove the organic solvent in the solution by vacuum evaporation at 40 mbar and at 40° C. in a water-bath. The 2 liothyronine nanoparticles were thus generated with an average diameter of 85-125 nm, and the suspension was translucent.

The nanoparticles were isolated from the resultant liothyronine albumin nanoparticle suspension by centrifugation method referred in Example 11 at 21000×g for 60 min. The supernatant was discarded, and the purified nanoparticles were collected. Purified nanoparticles were re-suspended in 5% mannitol solution. The re-suspension was filtered through a 0.22 μm sterile filter, and there was no significant variation of the particle size in the filtrate. The content of liothyronine in the solution was determined using HPLC. Based on the content, the solution was subsequently aliquoted into vials at an amount of 10 mg per vial. The vials were placed in a lyophilizer and lyophilized for 50 h.

When the lyophilized product was reconstituted in water for injection, the resultant cake was dissolved rapidly, the suspension was translucent, and no significant variation of the particle size was observed. After determination of the human serum albumin and liothyronine content in the product, the ratio between albumin and liothyronine can be calculated as 0.39:1.

Example 46. Preparation of Purified Epothilone B Albumin Particles 127 mg Epothilone B was dissolved into 2 ml chloroform/ethanol (10:1, v/v), and added into 52 ml human serum albumin solution (5% w/v). The mixture was emulsified for 2 min using a high shear disperser (Fluko FZ-20) to obtain a primary emulsion. The primary emulsion was then homogenized using a high pressure homogenizer under a pressure of 10000-20000 psi to obtain a nano-emulsion. Subsequently, the nano-emulsion was transferred to a rotatory evaporator to remove the organic solvent in the solution by vacuum evaporation at 40 mbar and at 40° C. in a water-bath. The Epothilone B nanoparticles were thus generated with an average diameter of 80-115 nm, and the suspension was translucent.

The nanoparticles were isolated from the resultant Epothilone B albumin nanoparticle suspension by equal volume dialysis against 5% mannitol. The purified nanoparticles suspension obtained was filtered through a 0.22 µm sterile filter, and there was no significant variation of the particle size in the filtrate. The content of Epothilone B in the solution was determined using HPLC. Based on the content, the solution was subsequently aliquoted into vials at an amount of 10 mg per vial. The vials were placed in a lyophilizer and lyophilized for 65 h.

When the lyophilized product was reconstituted in water for injection, the resultant cake was dissolved rapidly, the suspension was translucent, and no significant variation of the particle size was observed. After determination of the human serum albumin and Epothilone B content in the product, the ratio between albumin and Epothilone B can be calculated as 0.14:1.

Example 47. Preparation of Purified 10-Hydroxy Camptothecin Albumin Particles 93 mg 10-hydroxy camptothecin was dissolved into 2 ml chloroform/ethanol (10:1, v/v), and added into 48 ml human serum albumin solution (5% w/v). The mixture was emulsified for 2 min using a high shear disperser (Fluko FZ-20) to obtain a primary emulsion. The primary emulsion was then homogenized using a high pressure homogenizer under a pressure of 10000-20000 psi to obtain a nano-emulsion. Subsequently, the nano-emulsion was transferred to a rotatory evaporator to remove the organic solvent in the solution by vacuum evaporation at 40 mbar and at 40° C. in a water-bath. The 10-hydroxy camptothecin nanoparticles were thus generated with an average diameter of 100-135 nm, and the suspension was translucent.

The nanoparticles were isolated from the resultant 10-hydroxy camptothecin albumin nanoparticle suspension by centrifugation method referred in Example 11 at 21000×g for 60 min. The supernatant was discarded, and the purified nanoparticles were collected. Purified nanoparticles were re-suspended in 5% mannitol solution. The re-suspension was filtered through a 0.22 µm sterile filter, and there was no significant variation of the particle size in the filtrate. The content of 10-hydroxy camptothecin in the solution was determined using HPLC. Based on the content, the solution was subsequently aliquoted into vials at an amount of 20 mg per vial. The vials were placed in a lyophilizer and lyophilized for 72 h.

When the lyophilized product was reconstituted in water for injection, the resultant cake was dissolved rapidly, the suspension was translucent, and no significant variation of the particle size was observed. After determination of the human serum albumin and 10-hydroxy camptothecin content in the product, the ratio between albumin and 10-hydroxy camptothecin can be calculated as 0.26:1.

Example 48. Preparation of Purified Cyclosporine Albumin Particles 148 mg cyclosporine was dissolved into 1.5 ml chloroform/ethanol (11:1, v/v), and added into 18.5 ml human serum albumin solution (4% w/v). The mixture was emulsified for 2 min using a high shear disperser (Fluko FZ-20) to obtain a primary emulsion. The primary emulsion was then homogenized using a high pressure homogenizer under a pressure of 10000-20000 psi to obtain a nano-emulsion. Subsequently, the nano-emulsion was transferred to a rotatory evaporator to remove the organic solvent in the solution by vacuum evaporation at 40 mbar and at 40° C. in a water-bath. The cyclosporine nanoparticles were thus generated with an average diameter of 100-135 nm, and the suspension was translucent.

The nanoparticles were isolated from the resultant cyclosporine albumin nanoparticle suspension by chromatographic column separation method referred in Example 16. 10% lactose was use as the dialysate. The purified nanoparticles suspension obtained was filtered through a 0.22 µm sterile filter, and there was no significant variation of the particle size in the filtrate. The content of cyclosporine in the solution was determined using HPLC. Based on the content, the solution was subsequently aliquoted into vials at an amount of 50 mg per vial. The vials were placed in a lyophilizer and lyophilized for 72 h.

When the lyophilized product was reconstituted in water for injection, the resultant cake was dissolved rapidly, the suspension was translucent, and no significant variation of the particle size was observed. After determination of the human serum albumin and cyclosporine content in the product, the ratio between albumin and cyclosporine can be calculated as 0.26:1.

Example 49. Preparation of Purified Tanespimycin Albumin Particles 88 mg tanespimycin was dissolved into 2 ml chloroform/ethanol (8:1, v/v), and added into 18.5 ml human serum albumin solution (10% w/v). The mixture was emulsified for 2 min using a high shear disperser (Fluko FZ-20) to obtain a primary emulsion. The primary emulsion was then homogenized using a high pressure homogenizer under a pressure of 10000-20000 psi to obtain a nano-emulsion. Subsequently, the nano-emulsion was transferred to a rotatory evaporator to remove the organic solvent in the solution by vacuum evaporation at 40 mbar and at 40° C. in a water-bath. The tanespimycin nanoparticles were thus generated with an average diameter of 85-105 nm, and the suspension was translucent.

The nanoparticles were isolated from the resultant tanespimycin albumin nanoparticle suspension by chromatographic column separation method referred in Example 16. 5% mannitol was use as the dialysate. The purified nanoparticles suspension was filtered through a 0.22 µm sterile filter, and there was no significant variation of the particle size in the filtrate. The content of tanespimycin in the solution was determined using HPLC. Based on the content, the solution was subsequently aliquoted into vials at an amount of 50 mg per vial. The vials were placed in a lyophilizer and lyophilized for 72 h.

When the lyophilized product was reconstituted in water for injection, the resultant cake was dissolved rapidly, the suspension was translucent, and no significant variation of the particle size was observed. After determination of the human serum albumin and tanespimycin content in the product, the ratio between albumin and tanespimycin can be calculated as 0.62:1.

Example 50. Preparation of Purified Propofol Albumin Particles 603 mg propofol was dissolved into 6 ml chloroform, and added into 73 ml human serum albumin solution (10% w/v). The mixture was emulsified for 2 min using a high shear disperser (Fluko FZ-20) to obtain a primary emulsion. The primary emulsion was then homogenized using a high pressure homogenizer under a pressure of 10000-20000 psi to obtain a nano-emulsion. Subsequently, the nano-emulsion was transferred to a rotatory evaporator to remove the organic solvent in the solution by vacuum evaporation at 40 mbar and at 40° C. in a water-bath. The propofol nanoparticles were thus generated with an average diameter of 70-115 nm, and the suspension was translucent.

The nanoparticles were isolated from the resultant propofol albumin nanoparticle suspension by centrifugation method referred in Example 11 at 21000×g for 60 min. The supernatant was discarded, and the purified nanoparticles were collected. Purified nanoparticles were re-suspended in 10% lactose solution. The re-suspension was filtered through a 0.22 µm sterile filter, and there was no significant variation of the particle size in the filtrate. The content of propofol in the solution was determined using HPLC. Based on the content, the solution was subsequently aliquoted into vials at an amount of 50 mg per vial. The vials were placed in a lyophilizer and lyophilized for 72 h.

When the lyophilized product was reconstituted in water for injection, the resultant cake was dissolved rapidly, the suspension was translucent, and no significant variation of the particle size was observed. After determination of the human serum albumin and propofol content in the product, the ratio between albumin and propofol can be calculated as 0.58:1.

Example 51. Preparation of Purified Vinblastine Sulfate Albumin Particles 1.25 g vinblastine sulfate was dissolved into 10 ml chloroform/isopropanol (10:1, v/v), and added into 202 ml human serum albumin solution (5% w/v). The mixture was emulsified for 2 min using a high shear disperser (Fluko FZ-20) to obtain a primary emulsion. The primary emulsion was then homogenized using a high pressure homogenizer under a pressure of 10000-20000 psi to obtain a nano-emulsion. Subsequently, the nano-emulsion was transferred to a rotatory evaporator to remove the organic solvent in the solution by vacuum evaporation at 40 mbar and at 40° C. in a water-bath. The vinblastine sulfate nanoparticles were thus generated with an average diameter of 90-130 nm, and the suspension was translucent.

The nanoparticles were isolated from the resultant vinblastine sulfate albumin nanoparticle suspension by equal volume dialysis against 5% mannitol. The purified nanoparticles suspension obtained was filtered through a 0.22 µm sterile filter, and there was no significant variation of the particle size in the filtrate. The content of vinblastine sulfate in the solution was determined using HPLC. Based on the content, the solution was subsequently aliquoted into vials at an amount of 50 mg per vial. The vials were placed in a lyophilizer and lyophilized for 72 h.

When the lyophilized product was reconstituted in water for injection, the resultant cake was dissolved rapidly, the suspension was translucent, and no significant variation of the particle size was observed. After determination of the human serum albumin and vinblastine sulfate content in the product, the ratio between albumin and vinblastine sulfate can be calculated as 0.23:1.

Example 52. Preparation of Purified Exemestane Albumin Particles 155 mg exemestane was dissolved into 3 ml chloroform/ethanol (6:1, v/v), and added into 27 ml human serum albumin solution (5% w/v). The mixture was emulsified for 2 min using a high shear disperser (Fluko FZ-20) to obtain a primary emulsion. The primary emulsion was then homogenized using a high pressure homogenizer under a pressure of 10000-20000 psi to obtain a nano-emulsion. Subsequently, the nano-emulsion was transferred to a rotatory evaporator to remove the organic solvent in the solution by vacuum evaporation at 40 mbar and at 40° C. in a water-bath. The exemestane nanoparticles were thus generated with an average diameter of 70-100 nm, and the suspension was translucent.

The nanoparticles were isolated from the resultant exemestane albumin nanoparticle suspension by equal volume dialysis against 5% mannitol. The purified nanoparticles suspension obtained was filtered through a 0.22 µm sterile filter, and there was no significant variation of the particle size in the filtrate. The content of exemestane in the solution was determined using HPLC. Based on the content, the solution was subsequently aliquoted into vials at an amount of 50 mg per vial. The vials were placed in a lyophilizer and lyophilized for 72 h.

When the lyophilized product was reconstituted in water for injection, the resultant cake was dissolved rapidly, the suspension was translucent, and no significant variation of the particle size was observed. After determination of the human serum albumin and exemestane content in the product, the ratio between albumin and exemestane can be calculated as 0.19:1.

Example 53. Preparation of Purified Flutamide Albumin Particles 189 mg flutamide was dissolved into 2 ml chloroform/tert-butanol (6:1, v/v), and added into 38 ml human serum albumin solution (8% w/v). The mixture was emulsified for 2 min using a high shear disperser (Fluko FZ-20) to obtain a primary emulsion. The primary emulsion was then homogenized using a high pressure homogenizer under a pressure of 10000-20000 psi to obtain a nano-emulsion. Subsequently, the nano-emulsion was transferred to a rotatory evaporator to remove the organic solvent in the solution by vacuum evaporation at 40 mbar and at 40° C. in a water-bath. The flutamide nanoparticles were thus generated with an average diameter of 100-120 nm, and the suspension was translucent.

The nanoparticles were isolated from the resultant flutamide albumin nanoparticle suspension by chromatographic column separation method referred in Example 16. 5% dextran solution was used as dialysate. The purified nanoparticles suspension obtained was filtered through a 0.22 µm sterile filter, and there was no significant variation of the particle size in the filtrate. The content of flutamide in the solution was determined using HPLC. Based on the content, the solution was subsequently aliquoted into vials at an amount of 50 mg per vial. The vials were placed in a lyophilizer and lyophilized for 60 h.

When the lyophilized product was reconstituted in water for injection, the resultant cake was dissolved rapidly, the suspension was translucent, and no significant variation of the particle size was observed. After determination of the human serum albumin and flutamide content in the product, the ratio between albumin and flutamide can be calculated as 0.35:1.

Example 54. Preparation of Purified Fulvestrant Albumin Particles 350 mg fulvestrant was dissolved into 3 ml dichloromethane/ethanol (6:1, v/v), and added into 67 ml human serum albumin solution (5% w/v). The mixture was emulsified for 2 min using a high shear disperser (Fluko FZ-20) to obtain a primary emulsion. The primary emulsion was then homogenized using a high pressure homogenizer under a pressure of 10000-20000 psi to obtain a nano-emulsion. Subsequently, the nano-emulsion was transferred to a rotatory evaporator to remove the organic solvent in the solution by vacuum evaporation at 40 mbar and at 40° C. in a water-bath. The fulvestrant nanoparticles were thus generated with an average diameter of 105-150 nm, and the suspension was translucent.

The nanoparticles were isolated from the resultant fulvestrant albumin nanoparticle suspension by chromatographic column separation method referred in Example 16. 10% lactose was used as dialysate. The purified nanoparticles suspension obtained was filtered through a 0.22 μm sterile filter, and there was no significant variation of the particle size in the filtrate. The content of fulvestrant in the solution was determined using HPLC. Based on the content, the solution was subsequently aliquoted into vials at an amount of 20 mg per vial. The vials were placed in a lyophilizer and lyophilized for 60 h.

When the lyophilized product was reconstituted in water for injection, the resultant cake was dissolved rapidly, the suspension was translucent, and no significant variation of the particle size was observed. After determination of the human serum albumin and fulvestrant content in the product, the ratio between albumin and fulvestrant can be calculated as 0.29:1.

Example 55. Preparation of Purified Semustine Albumin Particles 650 mg semustine was dissolved into 5 ml chloroform/ethanol (6:1, v/v), and added into 89 ml human serum albumin solution (4% w/v). The mixture was emulsified for 2 min using a high shear disperser (Fluko FZ-20) to obtain a primary emulsion. The primary emulsion was then homogenized using a high pressure homogenizer under a pressure of 10000-20000 psi to obtain a nano-emulsion. Subsequently, the nano-emulsion was transferred to a rotatory evaporator to remove the organic solvent in the solution by vacuum evaporation at 40 mbar and at 40° C. in a water-bath. The semustine nanoparticles were thus generated with an average diameter of 85-120 nm, and the suspension was translucent.

The nanoparticles were isolated from the resultant semustine albumin nanoparticle suspension by centrifugation method referred in Example 11 at 21000×g for 60 min. The supernatant was discarded, and the purified nanoparticles were collected. Purified nanoparticles were re-suspended in 5% mannitol solution. The re-suspension was filtered through a 0.22 μm sterile filter, and there was no significant variation of the particle size in the filtrate. The content of semustine in the solution was determined using HPLC. Based on the content, the solution was subsequently aliquoted into vials at an amount of 20 mg per vial. The vials were placed in a lyophilizer and lyophilized for 70 h.

When the lyophilized product was reconstituted in water for injection, the resultant cake was dissolved rapidly, the suspension was translucent, and no significant variation of the particle size was observed. After determination of the human serum albumin and semustine content in the product, the ratio between albumin and semustine can be calculated as 0.58:1.

Example 56. Preparation of Purified Thiocolchicine Dimer Albumin Particles 456 mg thiocolchicine dimer was dissolved into 5 ml chloroform/ethanol (9:1, v/v), and added into 58 ml human serum albumin solution (8% w/v). The mixture was emulsified for 2 min using a high shear disperser (Fluko FZ-20) to obtain a primary emulsion. The primary emulsion was then homogenized using a high pressure homogenizer under a pressure of 10000-20000 psi to obtain a nano-emulsion. Subsequently, the nano-emulsion was transferred to a rotatory evaporator to remove the organic solvent in the solution by vacuum evaporation at 40 mbar and at 40° C. in a water-bath. The thiocolchicine dimer nanoparticles were thus generated with an average diameter of 65-90 nm, and the suspension was translucent.

The nanoparticles were isolated from the resultant thiocolchicine dimer albumin nanoparticle suspension by chromatographic column separation method referred in Example 16. 10% lactose was used as dialysate. The purified nanoparticles suspension obtained was filtered through a 0.22 μm sterile filter, and there was no significant variation of the particle size in the filtrate. The content of thiocolchicine dimer in the solution was determined using HPLC. Based on the content, the solution was subsequently aliquoted into vials at an amount of 20 mg per vial. The vials were placed in a lyophilizer and lyophilized for 70 h.

When the lyophilized product was reconstituted in water for injection, the resultant cake was dissolved rapidly, the suspension was translucent, and no significant variation of the particle size was observed. After determination of the human serum albumin and thiocolchicine dimer content in the product, the ratio between albumin and thiocolchicine dimer can be calculated as 0.37:1.

Example 57. Preparation of Purified Ibuprofen Dimer Albumin Particles 348 mg ibuprofen was dissolved into 3 ml dichloromethane/ethanol (11:1, v/v), and added into 62 ml human serum albumin solution (5% w/v). The mixture was emulsified for 2 min using a high shear disperser (Fluko FZ-20) to obtain a primary emulsion. The primary emulsion was then homogenized using a high pressure homogenizer under a pressure of 10000-20000 psi to obtain a nano-emulsion. Subsequently, the nano-emulsion was transferred to a rotatory evaporator to remove the organic solvent in the solution by vacuum evaporation at 40 mbar and at 40° C. in a water-bath. The ibuprofen nanoparticles were thus generated with an average diameter of 65-95 nm, and the suspension was translucent.

The nanoparticles were isolated from the resultant ibuprofen albumin nanoparticle suspension by chromatographic column separation method referred in Example 16. 5% dextran was used as dialysate. The purified nanoparticles suspension obtained was filtered through a 0.22 μm sterile filter, and there was no significant variation of the particle size in the filtrate. The content of ibuprofen in the solution was determined using HPLC. Based on the content, the solution was subsequently aliquoted into vials at an amount of 20 mg per vial. The vials were placed in a lyophilizer and lyophilized for 50 h.

When the lyophilized product was reconstituted in water for injection, the resultant cake was dissolved rapidly, the suspension was translucent, and no significant variation of the particle size was observed. After determination of the human serum albumin and ibuprofen content in the product, the ratio between albumin and ibuprofen can be calculated as 0.19:1.

Figure 12:
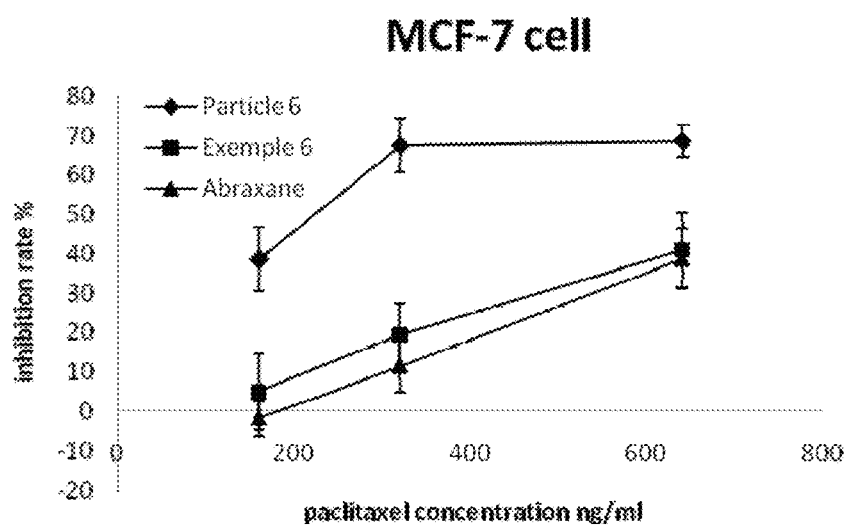
FIG. 12. Albumin concentration influences inhibition effect of drugs on MCF-7 cells.
Figure 13:
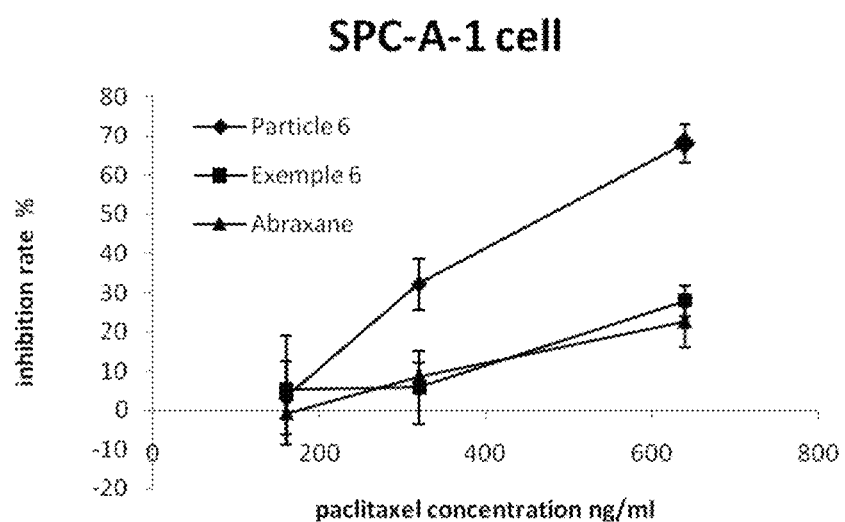
FIG. 13. Albumin concentration influences inhibition effect of drugs on SPC-A-1 cells.

Example 58. Albumin Concentration Influences Inhibition Effect of Drugs on Human Tumor Cells Human lung cancer cell SPC-A-1 and breast cancer cell MCF-7 were seeded to 96-well plate, cultured overnight and made them adherent to the wells. Then, the medium was changed to serum-free medium in order to starve the cells. Example 6, particle 6 and Abraxane were added to the cells at final concentrations of 160, 320, and 640 μg/ml (paclitaxel concentration) for 24 hours at 37° C. Cell inhibition rate of different dosing groups was compared by using MTT method, and the results were shown in the following table and FIGS. 12 and 13. Moreover, inhibition rate-drug concentration curve were drew too. As showing in the inhibition rate-drug concentration curve, the inhibition rate of particle 6 was significantly higher than other two groups, and no significant difference between Example 6 and Abaxane. That means redundant albumin will reduce the inhibition effect of paclitaxel on tumor cells.

Figure 14:
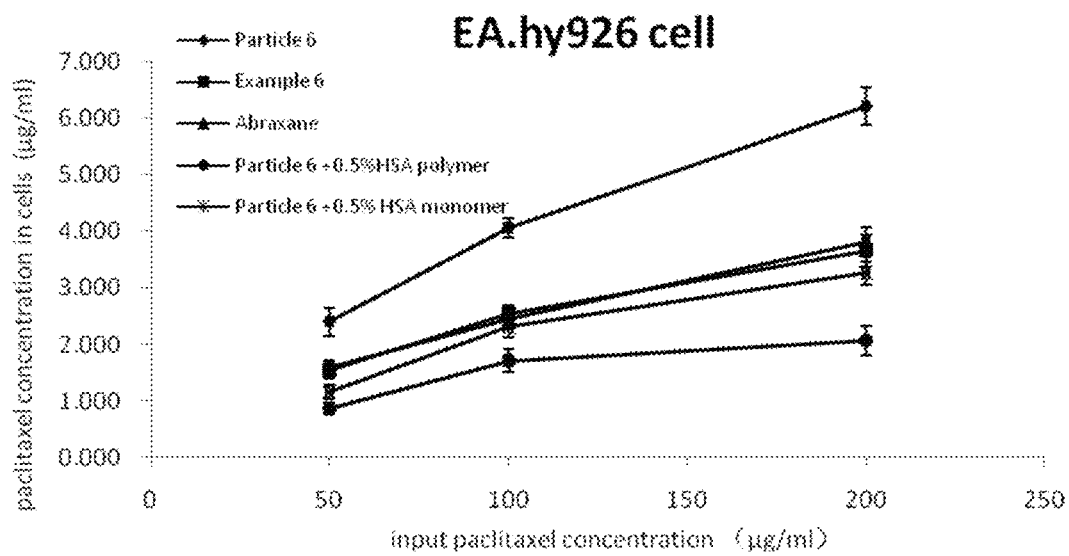
FIG. 14. Albumin concentration influences uptake of drugs by human vascular endothelial cell EA.hy 926.

Example 59. Albumin Concentration Influences Uptake of Drugs by Human Vascular Endothelial Cells Human umbilical vascular endothelial cells EA.hy 926 were seeded at $8 \times 10^5$ to 6-well plate. Before adding drugs, the medium was changed into serum-free medium. Drugs was divided into 5 groups, group A was particle 6, B was Example 6, C was Abraxane, D was particle 6+0.5% HSA monomer, E was particle 6+0.5% HSA polymer. Different groups of drug were added to the cells at final concentrations of 50, 100, and 200 μg/ml (paclitaxel concentration) for 2 hours at 37° C. After 2 hours, the cells were washed by PBS for 3 times, then 500 ul 5% TritonX-100 was added to each wells to lyse the cells. The paclitaxel concentration in cell lysis was detected by the method mentioned in example 10, and the results were shown in the following table and FIG. 14. The results show that cellular uptake of paclitaxel of group A was higher than group B and group C, and of group B and C had no significant difference. Furthermore, group D was higher than group E. That means higher HSA concentration hindered drug uptake to vascular endothelial cells, and compared to monomer, the HSA polymer would be more impede the cellular uptake.

TABLE 20

Drug concentration in cells of different treatment

| | | μg/ml | | |
|---|---|---|---|---|
| | | 50 | 100 | 200 |
| Particle 6 | concentration | 2.367 | 4.102 | 5.864 |
| | value | 2.165 | 3.873 | 6.227 |
| | | 2.668 | 4.217 | 6.531 |
| | mean | 2.400 | 4.064 | 6.207 |
| | SD | 0.253 | 0.175 | 0.334 |
| Exemple 6 | concentration | 1.362 | 2.415 | 3.374 |
| | value | 1.626 | 2.517 | 3.668 |
| | | 1.654 | 2.688 | 3.941 |
| | mean | 1.547 | 2.540 | 3.661 |
| | SD | 0.161 | 0.138 | 0.284 |

TABLE 19

Cells inhibition rate of different treatment

| Inhibition rate % | Particle 6 | | | Exemple 6 | | | Abraxane | | |
|---|---|---|---|---|---|---|---|---|---|
| | 640 μg/ml | 320 μg/ml | 160 μg/ml | 640 μg/ml | 320 μg/ml | 160 μg/ml | 640 μg/ml | 320 μg/ml | 160 μg/ml |
| MCF-7 cells | | | | | | | | | |
| No. 1 | 60.12 | 74.97 | 24.00 | 43.23 | 22.50 | -3.81 | 25.90 | 10.70 | 6.20 |
| No. 2 | 69.59 | 71.12 | 36.91 | 30.74 | 11.14 | 1.71 | 42.30 | 15.78 | -8.14 |
| No. 3 | 68.46 | 58.84 | 37.87 | 46.65 | 6.63 | 20.53 | 39.88 | 11.30 | -1.85 |
| No. 4 | 69.78 | 70.09 | 38.65 | 52.02 | 23.66 | 5.73 | 45.50 | 2.42 | -0.08 |
| No. 5 | 71.69 | 72.93 | 43.91 | 46.87 | 22.18 | 13.55 | 47.26 | 5.39 | -4.86 |
| No. 6 | 71.97 | 57.52 | 50.47 | 25.65 | 30.17 | -7.71 | 31.19 | 22.88 | -1.64 |
| mean | 68.60 | 67.58 | 38.63 | 40.86 | 19.38 | 5.00 | 38.67 | 11.41 | -1.73 |
| SD | 3.98 | 6.83 | 8.02 | 9.43 | 7.99 | 9.70 | 7.68 | 6.69 | 4.41 |
| SPC-A-1 cells | | | | | | | | | |
| No. 1 | 66.49 | 25.07 | 16.29 | 30.99 | 5.24 | 9.25 | 31.75 | 11.40 | -3.20 |
| No. 2 | 62.32 | 31.29 | -3.14 | 20.50 | -11.75 | -3.19 | 24.09 | 7.84 | -12.89 |
| No. 3 | 64.18 | 25.75 | 0.91 | 29.13 | 3.97 | -11.90 | 13.08 | 9.58 | 4.11 |
| No. 4 | 70.26 | 32.73 | -12.03 | 32.69 | 7.03 | -5.39 | 18.25 | 2.98 | -4.37 |
| No. 5 | 67.98 | 33.58 | 9.87 | 25.88 | 19.83 | 12.75 | 30.02 | 6.42 | -1.04 |
| No. 6 | 77.24 | 44.83 | 7.26 | 28.46 | 10.29 | 29.57 | 18.94 | 14.17 | 12.62 |
| mean | 68.08 | 32.21 | 3.19 | 27.94 | 5.77 | 5.18 | 22.69 | 8.73 | -0.80 |
| SD | 4.82 | 6.52 | 9.22 | 3.94 | 9.40 | 13.80 | 6.63 | 3.57 | 7.84 |

TABLE 20-continued

Drug concentration in cells of different treatment

| | | μg/ml | | |
|---|---|---|---|---|
| | | 50 | 100 | 200 |
| Abraxane | concentration value | 1.462 1.623 1.711 | 2.246 2.522 2.613 | 3.861 3.521 4.031 |
| | mean | 1.599 | 2.460 | 3.804 |
| | SD | 0.126 | 0.191 | 0.260 |
| Particle 6 + 0.5% HSA monomer | concentration value | 1.221 1.254 1.021 | 2.168 2.517 2.231 | 3.055 3.251 3.461 |
| | mean | 1.165 | 2.305 | 3.256 |
| | SD | 0.126 | 0.186 | 0.203 |
| Particle 6 + 0.5% HSA polymer | concentration value | 0.764 0.966 0.878 | 1.533 1.687 1.921 | 1.988 1.845 2.356 |
| | mean | 0.869 | 1.714 | 2.063 |
| | SD | 0.101 | 0.195 | 0.264 |

Example 60

The contents of albumin and paclitaxel (PTX) and the ratio of polymer in the human serum albumin used, product obtained in Example 6, and the corresponding nanoparticle 6 were determined using the method in Example 10. The results are listed in the following table.

TABLE 21

Contents of albumin polymer (Poly-HSA)

| | Monomer (%) | Polymer (%) | Albumin/palictaxel (mg/mg) | PolyHSA/PTX (mg/mg) |
|---|---|---|---|---|
| HSA | 95.8 | 4.2 | — | — |
| Example 6 | 80.7 | 19.3 | 8.8 | 1.7 |
| Particle 6 | 73.5 | 26.5 | 0.13 | 0.034 |

It has been revealed by the results that the ratio of poly-HSA was significantly increased during the preparation process of paclitaxel albumin nanoparticles. However, in the product prepared by the preparation method of the present disclosure, the amount of poly-HSA in unit weight is significantly reduced because of the decrease of total albumin content.

The amount of polymer in an albumin solution was increased by dialysis using a regenerated cellulose ultrafiltration membrane (PXC100C50, Millipore) with the cut-off molecular weight of 100K. The ratio of albumin polymer was detected using the method in Example 10, and the content of albumin was determined by Kjeldahl method to avoid the deviation produced by the different responses to potential polymers of HPLC method.

TABLE 22

The content of albumin polymer in HSA before and after dialysis

| | Monomer (%) | Polymer (%) |
|---|---|---|
| HSA before dialysis | 95.8 | 4.2 |
| HSA after dialysis | 25.1 | 74.9 |

It can be seen from the result that the albumin solution with a majority amount of polymer can be obtained by dialysis process.

Example 61. Sensitization Study of Poly-HSA in Guinea Pigs

In this experiment, the HSA and poly-HSA obtained from Example 60 were selected as the test drug. The dosages were selected as 1 mg per guinea pig and 0.3 mg per guinea pig. Sensitization was conducted by intraperitoneal injection once every other day, for a total of 3 injections. At the same time, a positive control group (0.2% ovalbumin) and a negative control group (0.9% sodium chloride injection) were also established. Detailed dosage regimen is listed in the table below.

TABLE 23

Protocol for sensitization study in guinea pig

| | | | sensitization | | Excitation | |
|---|---|---|---|---|---|---|
| Group | Number of animals | Concentration of the drug (mg/ml) | Administration volume (ml/animal) | Administration dosage (mg/animal) | Administration volume (ml/animal) | Administration dosage (mg/animal) |
| Negative control group | 6 | — | 0.5 | — | 1 | — |
| Positive control group | 6 | 2 | 0.5 | 1 | 1 | 2 |
| Low dosage of HSA | 6 | 0.6 | 0.5 | 0.3 | 1 | 0.6 |
| High dosage of HSA | 6 | 2 | 0.5 | 1 | 1 | 2 |
| Low dosage of Poly-HSA | 6 | 0.6 | 0.5 | 1.3 | 1 | 0.6 |
| High dosage of Poly-HSA | 6 | 2 | 0.5 | 1 | 1 | 2 |

Administration method for sensitization: the back of guinea pig was firmly held by cup-shape left hand, allowing the abdominal skin stretched when the guinea pig was fixed. The abdomen of the guinea pig was lifted, and the head was lowered down. After disinfecting of the injection site by an alcohol wipe, the needle of a 2 ml disposable syringe held by the right hand was punctured into the skin of the guinea pig. The needle was inserted at the site 1 mm left to the midline of lower abdomen. When arriving at the subcutaneous part, the needle was inserted forward for further 5 mm to 10 mm, and subsequently punctured into the abdominal cavity at an angle of 45°. After fixing the needle, the pharmaceutical solution was injected slowly. After the injection, a dry cotton wipe was pressed on the pinprick in order to prevent the outflow of the pharmaceutical.

Allergy excitation: excitation was conducted by intravenous injection, and the excitation was performed 10 d after the last sensitization with the dosages of 2 mg/animal and 0.6 mg/animal.

Administration method for excitation: injection was performed to the lateral metatarsal vein of the guinea pig fixed by an assistant. The stifles were grasped by the operator to fix the body of the animal. Its vein was compressed, and the legs were in a stretched state. The hair at the injection site was shaved (or the skin at the injection site was cut). After sterilization by alcohol wipes, thick lateral metatarsal vein can be seen. The needle of a 1 ml disposable syringe was punctured into the blood vessel along the direction to the heart by the right hand. After the injection, a dry cotton wipe was pressed on the pinprick in order to prevent bleeding.

The reaction of each animal and the time when allergy symptoms appeared or disappeared were observed immediately after the excitation for 30 min. Maximal observation duration was 3 h. The results of allergic reaction are listed in the following table.

TABLE 24

Symptoms of allergic reaction

| | |
|---|---|
| 0 | Normal |
| 1 | Dysphoria |
| 2 | Piloerection |
| 3 | Trembling |
| 4 | Nose scratching |
| 5 | Sneezing |
| 6 | Coughing |
| 7 | Tachypnea |
| 8 | Urination |
| 9 | Defecation |
| 10 | Lacrimation |
| 11 | Dyspnea |
| 12 | Wheezing |
| 13 | Peliosis |
| 14 | Gait disturbance |
| 15 | Jumping |
| 16 | Panting |
| 17 | Convulsion |
| 18 | Rotation |
| 19 | Cheyne-stokes respiration |
| 20 | Death |

TABLE 25

Evaluation criteria for systemic allergic reaction

| Symptom | Degree | Result |
|---|---|---|
| 0 | − | Negative allergic reaction |
| 1-4 | + | Weakly positive allergic reaction |
| 5-10 | ++ | Positive allergic reaction |
| 11-19 | +++ | Strongly positive allergic reaction |
| 20 | ++++ | Extremely positive allergic reaction |

TABLE 26

Results for active anaphylaxis of guinea pig

| Group | Number of the animal | Reaction level 1 | 2 | 3 | 4 | 5 | 6 | Positive rate |
|---|---|---|---|---|---|---|---|---|
| Negative control group | 6 | − | − | − | − | − | − | − |
| Positive control group | 6 | ++++ | ++++ | ++++ | ++++ | ++++ | ++++ | ++++ |
| Low dosage of HSA | 6 | + | − | − | − | + | − | + |
| High dosage of HSA | 6 | + | + | ++ | ++ | + | + | ++ |
| Low dosage of Poly-HSA | 6 | +++ | ++++ | +++ | ++ | +++ | +++ | +++ |
| High dosage of Poly-HSA | 6 | ++++ | ++++ | ++++ | ++++ | ++++ | ++++ | ++++ |

The results show that the samples containing more poly-HSA had stronger sensitization at same level of total HSA content.

Example 62

2.5 g paclitaxel (CAS: 33069-62-4, Yunnan Hande Bio-Tech Co., Ltd) was dissolved into 15 ml chloroform/ethanol (11:1, v/v), and added into which 500 ml human serum albumin solution (4% w/v) (CAS: 70024-90-7, Guangdong Shuanglin Biopharmaceutical. Co., Ltd.). The mixture was emulsified for 2 min using a high shear disperser (Fluko FZ-20) to obtain a primary emulsion. The primary emulsion was then homogenized using a high pressure homogenizer (Model M110-EH30K, MFIC Company, USA) under a pressure of 10000-20000 psi to obtain a nano-emulsion. Subsequently, the nano-emulsion was transferred to a rotatory evaporator (Model R-210, Buchi Company, Switzerland) to remove the organic solvent in the solution by vacuum evaporation at 40 mbar and at 40° C. in a water-bath. The paclitaxel-albumin nanoparticles were thus generated with an average diameter of 129 nm, and the suspension was translucent. The suspension can be smoothly filtered through a 0.22 µm sterile filter (Sartorius AG, Germany). There was no significant variation of the particle size after filtration, and no significant change was observed after storage for 48 h at room temperature.

The purified nanoparticles were isolated respectively by centrifugation in Example 11, by dialysis in Example 15 and by chromatographic column separation in Example 16. The results showed that the suspension became turbid and precipitated during dialysis. Thus purified nanoparticles couldn't be obtained though this method. While the purified nanoparticles obtained by centrifugation and chromatographic column separation were turbid and precipitated in 60 min.

Example 63

2.5 g paclitaxel (CAS: 33069-62-4, Yunnan Hande Bio-Tech Co., Ltd) was dissolved into 15 ml chloroform/ethanol (11:1, v/v), and added into which 500 ml human serum albumin solution (4% w/v) (CAS: 70024-90-7, Guangdong Shuanglin Biopharmaceutical. Co., Ltd.). The mixture was emulsified for 2 min using a high shear disperser (Fluko FZ-20) to obtain a primary emulsion. The primary emulsion was then homogenized using a high pressure homogenizer (Model M110-EH30K, MFIC Company, USA) under a pressure of 10000-20000 psi to obtain a nano-emulsion. Subsequently, the nano-emulsion was transferred to a rotatory evaporator (Model R-210, Buchi Company, Switzerland) to remove the organic solvent in the solution by vacuum evaporation at 40 mbar and at 40° C. in a water-bath. The paclitaxel-albumin nanoparticles were thus generated with an average diameter of 128 nm, and the suspension was translucent. The suspension can be smoothly filtered through a 0.22 μm sterile filter (Sartorius AG, Germany). There was no significant variation of the particle size after filtration, and no significant change was observed after storage for 48 h at room temperature.

Dialysis was conducted in equal volume to the samples prepared against purified water using a regenerated cellulose ultrafiltration membrane (PXC300C50, Millipore) with the cut-off molecular weight of 30K, and the dialysis fold was 5.

The purified nanoparticles were isolated respectively by centrifugation in Example 11, by dialysis in Example 15 and by chromatographic column separation in Example 16. The resulted translucent suspensions from all the 3 methods were stable and can be smoothly filtered through a 0.22 μm sterile filter (Sartorius AG, Germany). There was no significant variation of the particle size after filtration, and no significant change was observed after storage for 48 h at room temperature Comparing Examples 62 and 63, an extra process of equal volume dialysis against purified water was conducted in Example 63 to remove the residual solvents. The removal of the residual solvents improved stability of suspension of purified nanoparticles.

Discussion:

Prior art formulations have a high ratio of albumin to an active ingredient (for example, 9:1). It has been unexpectedly discovered by the present inventors that in such a formulation, most albumin acts only as a protective or support agent in the lyophilized product. Most drug molecules (for example, paclitaxel) are encapsulated in the nanoparticles, and albumin that does not form particles is substantially free of drug molecules. In prior art formulations, most human serum albumin molecules are not bound to the drug molecules.

After administration, particles in prior art formulations are disintegrated rapidly, and complexes are formed between the drug molecules and the endogenous human serum albumin. Consequently, excessive human serum albumin in the prior art formulations does not contribute to the efficacy of the formulations (see Example 26), but instead causes safety risks due to its aggregation and immunogenicity (see Examples 32, 25 and 27). Furthermore, extra albumin may compete with the drug-albumin complex to bind to the gp60 receptor, thus decrease the drug uptake by the vascular endothelial cells (see Example 59). Moreover, after binding to the poly-HSA formed in preparation process, the gp60 receptor may be unable to be transcytosed effectively, thus preventing the receptor from being released. This may further inhibit the drug uptake by the endothelial cells, and thus decrease the effective concentration of drugs.

Based on the discoveries above, purified nanoparticles of the present disclosure have a lower albumin: active ingredient ratio. It has been confirmed by the present inventors that only a small amount of human serum albumin was required for forming stable nanoparticles with drug molecules. The reduction in human serum albumin in purified nanoparticles and compositions thereof provided herein reduces adverse reactions associated with aggregation and immunogenicity of human serum albumin.

After administration, purified nanoparticles provided herein were able to be disintegrated rapidly, and bound to endogenous albumin for circulation in vivo. There were no significantly difference observed in terms of safety and efficacy in animal studies compared with prior art formulation. However, purified nanoparticles and compositions thereof provided herein improved uptake by human vascular endothelial cells as well as delivery and effectiveness of active ingredients in the nanoparticles to or in human target cells.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. Purified therapeutic nanoparticles, consisting essentially of paclitaxel and human serum albumin (HSA), wherein the weight ratio of HSA to paclitaxel in the therapeutic nanoparticles is from 0.03:1 to 0.95:1, wherein less than 10% HSA in the therapeutic nanoparticles is free HSA that is not incorporated into the nanoparticles, wherein the therapeutic nanoparticles contain less than 0.05 mg/ml organic solvent(s), and wherein when suspended in 0.9% sodium chloride or 5% mannitol, the resulting suspension is stable for 48 hours at room temperature.

2. A pharmaceutical composition, comprising the purified therapeutic nanoparticles of claim 1, wherein less than 10% of HSA in the composition is free HSA that is not incorporated in the nanoparticles.

3. The pharmaceutical composition of claim 2, wherein the weight ratio of HSA to paclitaxel of the therapeutic nanoparticles is from 0.03:1 to 0.7:1, and wherein the average particle size of the therapeutic nanoparticles is from 50 nm to 190 nm.

4. The pharmaceutical composition according to claim 2, wherein the pharmaceutical composition is in the form of liquid or lyophilized powder.

5. The pharmaceutical composition according to claim 2, wherein the pharmaceutical composition also comprises lyophilization excipient when the pharmaceutical composition is in the form of lyophilized powder.

6. The pharmaceutical composition according to claim 5, wherein the lyophilization excipient is selected from one or more of mannitol, sucrose, lactose, maltose, trehalose, and dextran.

7. The pharmaceutical composition according to claim 2, wherein at most 5% of the HSA in the composition is free HSA (by weight) that is not incorporated in the nanoparticles.

8. The pharmaceutical composition according to claim 2, wherein the weight ratio of HSA to paclitaxel of the therapeutic particles is from 0.03:1 to 0.7:1.

9. The pharmaceutical composition according to claim 2, wherein the therapeutic nanoparticles contain less than 5 ug/ml organic solvent(s).

10. The pharmaceutical composition according to claim 2, wherein less than 1% of the HSA in the composition is free HSA (by weight) that is not incorporated in the nanoparticles.

11. The pharmaceutical composition according to claim 2, wherein the average particle size of the therapeutic nanoparticles is from 100 nm to 160 nm.

12. The pharmaceutical composition of claim 2, wherein the weight ratio of HSA to paclitaxel is from 0.10:1 to 0.6:1.

13. The pharmaceutical composition according to claim 2, wherein the organic solvent(s) is a pure solvent having low water-solubility and a low boiling point or a mixture of a solvent having low water-solubility and a low boiling point with a small molecular alcohol.

14. The pharmaceutical composition according to claim 2, wherein the weight ratio of HSA to paclitaxel in therapeutic nanoparticles is from 0.04:1 to 0.75:1.

15. The pharmaceutical composition according to claim 2, wherein the average particle size of the therapeutic nanoparticles is from 30 to 200 nm.

16. A method for preparing the purified therapeutic nanoparticles of claim 1, comprising:
   1) dissolving paclitaxel in organic solvent to form an oil phase, and dissolving human serum albumin in water to form an aqueous phase;
   2) forming an oil-in-water emulsion using the oil phase and aqueous phase of step 1);
   3) removing the organic solvent in the emulsion to obtain a suspension containing the therapeutic nanoparticles; and
   4) removing free HSA that is not incorporated in the nanoparticles from the suspension to obtain purified therapeutic nanoparticles.

17. The method according to claim 16, wherein the organic solvent is selected from one or more of chloroform and ethanol.

18. The method according to claim 16, further comprising: between steps 3) and 4), a step of dialyzing the suspension of step 3) with an aqueous solution to remove remaining organic solvent from the suspension.

19. The method according to claim 18, wherein the aqueous solution is water.

20. The method according to claim 16, wherein said separating in step 4) is conducted using a method selected from: centrifugation, dialysis, and exclusion chromatography.

21. A method for preparing the pharmaceutical composition according to claim 2, comprising:
   1) dissolving paclitaxel in organic solvent to form an oil phase, and dissolving human serum albumin in water to form an aqueous phase;
   2) forming an oil-in-water emulsion using the oil phase and aqueous phase of step 1);
   3) removing the organic solvent in the emulsion to obtain a suspension containing the therapeutic nanoparticles;
   4) removing free HSA that is not incorporated in the nanoparticles to obtain purified therapeutic nanoparticles;
   5) re-suspending the purified therapeutic nanoparticles in an excipient-containing solution; and
   6) optionally lyophilizing the re-suspension of the purified therapeutic nanoparticles to obtain the pharmaceutical composition.

22. The method of claim 21, further comprising: between steps 3) and 4), a step of dialyzing the suspension of step 3) with an aqueous solution to remove remaining organic solvent from the suspension.

23. The method according to claim 22, wherein the aqueous solution is water.

24. A method for preparing the pharmaceutical composition according to claim 2, comprising:
   1) dissolving paclitaxel in organic solvent to form an oil phase, and dissolving human serum albumin in water to form an aqueous phase;
   2) forming an oil-in-water emulsion using the oil phase and aqueous phase of step 1);
   3) removing the organic solvent in the emulsion to obtain a suspension containing the therapeutic nanoparticles;
   4) dialyzing the suspension obtained after removal of the organic solvent by an excipient-containing solution to remove free HSA that is not incorporated in the nanoparticles; and
   5) optionally lyophilizing the dialyzed suspension to obtain the pharmaceutical composition.

25. The method of claim 24, further comprising: between steps 3) and 4), a step of dialyzing the suspension of step 3) with an aqueous solution to remove remaining organic solvent from the suspension.

26. The method of claim 25, wherein the aqueous solution is water.

27. A method for treating cancer, comprising:
   administering a therapeutically effective amount of the pharmaceutical composition according to claim 2 to a subject in need thereof.

28. A method for treating cancer, comprising:
   administering a therapeutically effective amount of the pharmaceutical composition according to claim 3 to a subject in need thereof.

* * * * *